United States Patent
Receveur et al.

(10) Patent No.: US 8,173,680 B2
(45) Date of Patent: May 8, 2012

(54) CANNABINOID RECEPTOR MODULATORS

(75) Inventors: Jean-Marie Receveur, Hoersholm (DK); Emelie Bjurling, Hoersholm (DK); Anthony Murray, Hoersholm (DK); Thomas Hoegberg, Hoersholm (DK); Peter Aadal Nielsen, Hoersholm (DK); Jean-Michel Linget, Hoersholm (DK); Pia Karina Noerregaard, Hoersholm (DE); Dorthe Almholt, Hoersholm (DK)

(73) Assignee: 7TM Pharma A/S, Hoersholm (DK)

( * ) Notice: Subject to any disclaimer, the term of this patent is extended or adjusted under 35 U.S.C. 154(b) by 0 days.

(21) Appl. No.: 12/745,708

(22) PCT Filed: Dec. 8, 2008

(86) PCT No.: PCT/GB2008/004051
§ 371 (c)(1),
(2), (4) Date: Aug. 5, 2010

(87) PCT Pub. No.: WO2009/074782
PCT Pub. Date: Jun. 18, 2009

(65) Prior Publication Data
US 2010/0292273 A1   Nov. 18, 2010

(30) Foreign Application Priority Data
Dec. 10, 2007 (GB) .................................. 0724096.3
Jul. 21, 2008 (GB) .................................. 0813350.6

(51) Int. Cl.
| A61K 31/445 | (2006.01) |
| A61K 31/41 | (2006.01) |
| A61K 31/415 | (2006.01) |
| C07D 401/02 | (2006.01) |
| C07D 271/06 | (2006.01) |
| C07D 231/00 | (2006.01) |

(52) U.S. Cl. ........ 514/326; 514/364; 514/406; 546/209; 546/132; 546/374.1

(58) Field of Classification Search .................. 514/326, 514/364, 406; 546/209; 548/132, 374.1
See application file for complete search history.

(56) References Cited

U.S. PATENT DOCUMENTS
2006/0135776 A1   6/2006 Barth et al.
2007/0213302 A1   9/2007 McElroy FOREIGN PATENT DOCUMENTS
| WO | 2006133926 A | 12/2006 |
| WO | 2008059207 A | 5/2008 |
| WO | 2008075012 A | 6/2008 |
| WO | 2008075013 A | 6/2008 |
| WO | 2008075019 A | 6/2008 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Camille G. Wermuth: "Molecular variants based on isosteric replacements" The Practice of Medicinal Chemistry Elsevier, Jan. 1, 2003, pp. 189-214, XP009112544.
Hogenauer E K: "Latest advances in the cannabinoids" Expert Opinion on Therapeutic Patents 200712 GB, vol. 17, No. 12, Dec. 2007, pp. 1457-1476, XP002517654.
International Search Report for PCT/GB2008/004051 dated Mar. 4, 2009.

* cited by examiner

*Primary Examiner* — Rebecca Anderson
*Assistant Examiner* — Samantha Shterengarts
(74) *Attorney, Agent, or Firm* — Banner & Witcoff, Ltd.

(57) ABSTRACT

Compounds of formula (I) are modulators of cannabinoid receptor CB1, useful inter alia for treatment of obesity: Formula (I). Wherein: X is a bond, or a divalent radical selected from $-C(R_{10})(R_{11})-*$, $-C(R_{10})(R_{11})-O-*$, $-C(R_{10})(R_{11})CH_2-*$, $-C(R_{10})(R_{11})CH_2-O-*$, $-CH_2C(R_{10})(R_{11})-*$, $-CH_2C(R_{10})(R_{11})-O-*$, and $-CH_2-O-C(R_{10})(R_{11})-*$, wherein the bond indicated by an asterisk is attached to the pyrazole ring; Z is a carboxyl isostere radical selected from the group specified; $R_3$ is hydrogen, $(C_1-C)$alkyl or $(C_1C_3)$fluoroalkyl; $R_4$ is a radical of formula $-(Alk_1)_p-(Q_1)_r-(L)_s-Q_2$ wherein p, r, s, $Alk_1$, L, $Q_1$ and $Q_2$ are as specified; or $R_3$ and $R_4$ taken together with the nitrogen to which they are attached form a cyclic amino ring of 4 to 7 ring atoms which is optionally substituted by a radical of formula $-(L)_s-Q_2$ wherein s, L and $Q_2$ are as defined above, or by an optional substituent selected from hydroxy, methoxy, $-NH_2-$, or mono- or di-$(C_1C_3)$alkylamino; $R_5$, $R_6$, $R_7$ and $R_8$ are each independently selected from hydrogen $-F$, $-Cl$, $-Br$, $-CN$, $(C_1-C_3)$alkyl, $(C_1C_3)$fluoroalkyl, cyclopropyl, and $-OR_9$; $R_{10}$ is hydrogen, $(C_1C_3)$alkyl, hydroxyl or $NH_2$, and $R_{11}$ is hydrogen or $(C_1-C_3)$alkyl; or $R_{10}$ and $R_{11}$ taken together with the carbon atom to which they are attached form a $(C_3-C_5)$cycloalkyl ring.

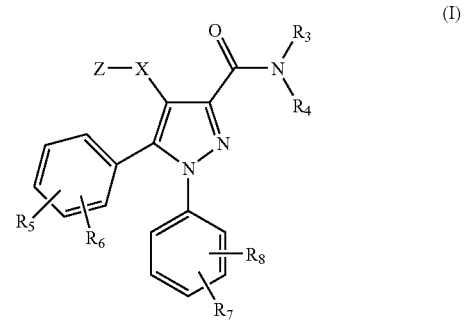

14 Claims, No Drawings

CANNABINOID RECEPTOR MODULATORS

CROSS REFERENCE TO RELATED APPLICATIONS

This application is a National Stage application of co-pending PCT application PCT/GB2008/004051 filed Dec. 8, 2008, which application claims benefit from Great Britain Application No. 0724096.3 filed Dec. 10, 2007 and Great Britain Application No. 0813350.6 filed Jul. 21, 2008. These applications are hereby incorporated by reference in their entireties.

The present invention relates to compounds which are modulators of cannabinoid receptor CB1 and which suppress the normal signalling activity of such receptors. The invention further relates to compositions and methods using said compounds for the treatment of diseases or conditions which are mediated by CB1 receptor signalling activity, such as treatment of obesity and overweight, prevention of weigh gain, treatment of diseases and conditions directly or indirectly associated with obesity and overweight such as metabolic syndrome, type 2 diabetes, cardiovascular disease, metabolic dysfunctions in obese, overweight or normoweight individuals, metabolic diseases or disorders, cancers, liver diseases and other secondary diseases referred to below, as well as for the treatment of some disorders not necessarily related to obesity and overweight, such as eating disorders, addictive disorders, mental disorders, neurological disorders, sexual dysfunctions, reproductive dysfunctions, liver diseases, fibrosis-related diseases and other clinical indications referred to below. The invention also relates to pharmaceutical compositions containing the compounds of the invention, and to the use of the compounds in combination with other treatments for such disorders.

BACKGROUND TO THE INVENTION

The prevalence of obesity in North America and in most European countries has more than doubled in the last 20 years and over half of the adult population are now either overweight or obese. Obesity is now recognized as a chronic disease and a critical global health issue (Fiegal et al, 1998, Int. J. Obesity 22:39-47, Mokdad et al, 1999, JAMA 282: 1519-1522; Halford, 2006, Appetite, 46, 6-10). The "identifiable signs and symptoms" of obesity include an excess accumulation of fat or adipose tissue, an increase in the size or number of fat cells (adipocyte differentiation), insulin resistance, increased glucose levels (hyperglycemia), increased blood pressure, elevated cholesterol and triglyceride levels and decreased levels of high-density lipoprotein. Obesity is associated with a significantly elevated risk for type 2 diabetes, coronary heart disease, stroke, hypertension, various types of cancer and numerous other major illnesses, and overall mortality from all causes (Must et al, 1999, JAMA 282:1523-1529, Calle et al, 1999, N. Engl. J. Med. 341:1097-1105). A cluster of metabolic risk factors for cardiovascular disease and type 2 diabetes is often referred to as metabolic syndrome, syndrome X or insulin resistance syndrome. The major components of metabolic syndrome X include excess abdominal fat (also known as visceral, male-pattern or apple-shaped adiposity), atherogenic dyslipidemia (decreased high-density lipoprotein cholesterol (HDL-C)), elevated triglycerides), hypertension, hyperglycaemia (diabetes mellitus type 2 or impaired fasting glucose, impaired glucose tolerance, or insulin resistance), a proinflammatory state and a prothrombotic state. (cf. AHA/NHLBI/ADA Conference Proceedings, Circulation 2004; 109:551-556). Other abnormalities often associated with the metabolic syndrome include increased apolipoprotein B concentrations, low adiponectin plasma levels, small dense low-density lipoprotein (LDL) particles, hyperuricaemia, non-alcoholic fatty liver disease/hepatic steatosis, elevated liver transaminases, gamma-glutamyl-transferase and microalbuminuria.

Like obesity, the prevalence of obesity-related diseases such as diabetes also continues to rise. Weight reduction is critical for the obese patient as it can improve cardiovascular and metabolic values to reduce obesity-related morbidity and mortality (Blackburn, 1999, Am. J. Clin. Nujtr. 69:347-349, Galuska et al, 1999, JAMA 282:1576). It has been shown that 5-10% loss of body weight can substantially improve metabolic parameters such as levels of fasting and post-prandial blood glucose, HbA1c (glycosylated haemoglobin), insulin, total plasma cholesterol, low density lipoproteins (LDL), triglyceride, uric acid and blood pressure and reduce the risk for development of diabetes, cancer and cardiovascular diseases (Goldstein, 1992, J. Obesity, 6, 397-415).

Thus, a primary aim of treatment for obesity, and obesity-related disorders, is weight loss. Initially, treatments are based on diet and lifestyle changes augmented by therapy with pharmacological therapies. However, while physical exercise and reductions in dietary intake of calories can improve the obese condition, compliance with this treatment is very poor because of sedentary lifestyles and excess food consumption, especially high fat containing food. Additionally, treatment with the available pharmacological therapies to facilitate weight loss fail to provide adequate benefit to many obese patients because of experienced side effects, contraindications, or lack of positive response. Hence, there is impetus for developing new and alternative treatments for management of obesity.

Several potential anti-obesity agents are currently investigated (for a review, see Bays, 2004, Obesity Research, 12, 1197-1211) such as i) central nervous system agents that affect neurotransmitters or neural ion channels (e.g. antidepressants (bupropion), noradrenaline reuptake inhibitors (GW320659), selective 5HT 2c receptor agonists, antiseizure agents (topiramate, zonisamide), some dopamine antagonists, cannabinoid CB-1 receptor antagonists (rimonabant);

ii) leptin/insulin/central nervous system pathway agents (e.g. leptin analogues, leptin transport and/or receptor promoters, CNTF (Axokine), NPY antagonists, AgRP antagonists, POMC promoters, CART promoters, MSH analogues, MC4 receptor agonists, agents that affect insulin metabolism/activity [PTP-1B inhibitors, PPAR receptor antagonists, short-acting D2 agonist (ergoset), somatostatin agonists (octreotide), and adiponectin/Acrp30 (Famoxin or Fatty Acid Metabolic OXidation INducer)]);

iii) gastrointestinal-neural pathway agents (e.g. agents that increase CCK and PYY activity, agents that increase GLP-1 activity (extendin 4, liraglutide, dipeptidyl peptidase IV inhibitor), agents that decrease ghrelin activity, amylin (pramlinitide), neuropeptide Y agonists);

iv) agents that may increase resting metabolic rate (beta-3 agonists, UCP homologues, thyroid receptor agonists); and v) other more diverse agents, such as for example including (MCH) melanin concentrating hormone antagonists, phytostanol analogues, functional oils, P57, amylase inhibitors, growth hormone fragments, synthetic analogues of DHEAS (fluasterone), antagonists of adipocyte 11beta-hydroxysteroid dehydrogenase type 1 activity, CRH agonists, carboxypeptidase inhibitors, inhibitors of fatty acid synthesis (cerulenin and C75), indanones/indanols, aminosterols (trodusquemine), and other gastrointestinal lipase inhibitors (ATL962).

Drugs effective in obesity treatment may act by various mechanisms such as by: a reduction of food intake (e.g. by inducing satiety or satiety signals), altering metabolism (e.g. by modifying the absorption of nutrients e.g. by inhibition of fat absorption), increasing energy expenditure (e.g. increase thermogenesis), inhibition of lipogenesis or stimulation of adipocyte apoptosis. However, only few drugs are available for obesity treatment (for reviews, see Gadde and Allison, 2006, Circulation, 114, 974-984; Weigle, 2003, J Clin Endocrinol Metab., 88, 2462-2469; Schiöth, 2006, CNS Neurol. Disorders Drug Targets, 5, 241-249). Sibutramine is a centrally acting mixed inhibitor of serotonin and norepinephrine presynaptic re-uptake. Orlistat is an inhibitor of gastrointestinal lipases which reduces fat absorption in the gut. Rimonabant (SR141716, Acomplia®) is a centrally and peripherally acting cannabinoid CB1 modulator (antagonist and inverse agonist) that recently has been approved for treatment of obesity (for a review see Pagotto et al, 2006, Endocrine Reviews, 27, 73-100; for reports on phase III clinical trials see Despres et al, 2005, N. Engl. J. Med. 353, 212; van Gaal et al, 2005, Lancet, 16, 1389; Pi-Sunyer et al, 2006, JAMA, 295, 761).

Presently, two cannabinoid receptors have been characterized: CB1, a receptor found in the mammalian brain and in a number of other sites in peripheral tissues; and CB2, a peripheral receptor found principally in cells related to the immune system. For reviews on cannabinoid CB1 and CB2 receptor modulators, see Pertwee, 2000, Exp. Opin. Invest. Drugs, 9, 1553-1571 and Muccioli, 2005, Cur. Med. Chem., 12, 1361-1394. A substantial body of evidence indicates that CB1 antagonists (e.g. rimonabant) are able to modulate energy homeostasis and that CB1 antagonists are able to modulate food intake as well as peripherally block lipogenic processes (Pagotto et al, 2006, Endocrine Reviews, 27, 73-100; Tucci et al, 2006, Curr. Med. Chem. 13, 2669-2680; Lange and Kruse, 2004, Current Opinion in Drug Discovery & Dev., 7, 498-506). The peripheral effects of CB1 antagonists can be mediated by several target organs and mechanisms, e.g. i) liver: block of de novo lipogenesis, ii) muscles: increase in glucose uptake, iii) adipose tissue: stimulation of expression and/or secretion of adiponectin, inhibition of lipogenic enzymes, stimulation of GLUT4, generation of futile cycles, iv) pancreas: insulin regulation and v) gastrointestinal tract: stimulation of satiety signals.

Rimonabant (Acomplia®) is approved as an adjunct to diet and exercise for treatment of obesity. While the effects on body weight and metabolic parameters (plasma triglyceride levels, HDL cholesterol levels, plasma insulin levels, HbA1c [glycosylated haemoglobin] levels, insulin resistance, and adiponectin levels) are very encouraging, there are also undesirable side effects, possibly centrally mediated (psychiatric and nervous system disorders), such as anxiety, depressive disorders, sleep disorders, nausea, and vomiting (cf. http://emc.medicines.org.uk; http://www.emea.europa.eu/humandocs/PDFs/EPAR/acomplia/AcompliaEparScientificDen-.pdf). Accordingly, there still exists a need for alternative CB1 receptor antagonists associated with differing pharmacokinetic, pharmacological, and side-effect profiles.

The CB1 receptor has been invoked in many disease states (cf. review by Pacher et al, 2006, Pharmacol. Rev, 58, 389-462). Modulators of CB1 receptor activity can be useful in the treatment of diseases and conditions associated with CB1 receptor regulation such as obesity and overweight, prevention of weight gain (e.g. induced by medications or smoking cessation), and in the treatment of diseases and conditions directly or indirectly associated with obesity (cf. Bray, 2004, J. Clin. Endocrinol. Metab. 89, 2583-9; Manson, et al, 1995, N. Engl. J. Med. 333, 677-85; Grundy, 2004, J. Clin. Endocrinol. Metab. 89, 2595-600; Esposito et al, 2004, JAMA 291; 2978-84; Ejerblad et al, 2006; J. Am. Soc. Nephrol. 17, 695-702; Whitmer et al, 2005, BMJ 330 (7504), 1360) such as metabolic syndrome, also referred to as syndrome X or insulin resistance syndrome, type 2 diabetes, cardiovascular diseases (e.g. aneurysms, angina, arrhythmia, atherosclerosis, cardiomyopathy, cerebrovascular accident (stroke), cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy and its associated arrhythmias and dizziness, mitral valve prolapse, myocardial infarction (heart attack), venous thromboembolism, varicose veins and pulmonary embolism, proinflammatory state, increased tendency to thrombosis (prothrombotic state), and intracranial hypertension, metabolic dysfunctions in obese, overweight or normoweight individuals (e.g. dyslipidemia, hyperlipidemia, low HDL and/or high LDL cholesterol levels, hypertriglycerideemia, low adiponectin levels, impaired glucose tolerance, insulin resistance, increase in HbA1c [glycosylated haemoglobin] levels, diabetes mellitus, type 2 diabetes, reduced metabolic activity), metabolic diseases or disorders (conditions in which there is a deviation from or caused by an abnormal metabolic process; can be congenital due to inherited enzyme abnormality or acquired due to disease of an endocrine organ or failure of a metabolically important organ such as the liver.), cancers (e.g. colorectal cancer, breast cancer, uterine cancer, colon cancer), liver diseases (e.g. non-alcoholic fatty liver disease, steatohepatitis, steatosis, hepatic fibrosis, hepatic cirrhosis), and other secondary diseases related to obesity and overweight, such as menstrual disorders, gastroesophageal reflux disease, cholelithiasis (gallstones), hernia, urinary incontinence, chronic renal failure, hypogonadism (male), stillbirth, stretch marks, acanthosis nigricans, lymphedema, cellulitis, carbuncles, intertrigo, hyperuricemia, immobility, osteoarthritis, low back pain, meralgia paresthetica, headache, carpal tunnel syndrome, dementia, idiopathic dyspnea, obstructive sleep apnea, hypoventilation syndrome, Pickwickian syndrome, asthma, depression, low self esteem, body dysmorphic disorder, social stigmatization.

The CB1 receptor has been invoked in many disease states diseases not necessarily related to obesity and overweight such as eating disorders, addictive disorders (e.g. addiction to marijuana, psychostimulants, nicotine, alcohol, cocaine, and opiates), mental disorders (e.g. schizophrenia, schizo-affective disorder, bipolar disorders, anxiety, panic disorder), neurological disorders, sexual dysfunctions (e.g. erectile dysfunction), reproductive dysfunctions (e.g. polycystic ovarian syndrome, infertility), liver diseases (e.g., viral hepatitis, liver dysfunction in other infectious diseases, inflammatory liver diseases (e.g. autoimmune hepatitis), alcoholic liver disease, toxic liver disease, liver tumors (such as liver cell carcinoma, hepatocellular carcinoma, hepatoma, cholangiocarcinoma, hepatoblastoma, angiosarcoma of liver, Kupffer cell sarcoma, other sarcomas of liver), steatohepatitis, non-alcoholic fatty liver disease hepatic fibrosis, hepatic cirrhosis, cirrhotic portal hypertension, metabolic liver diseases (such as haemochromatosis, Wilson's disease, Gilbert's syndrome, Crigler-Najjar syndrome, Dubin-Johnson syndrome, Rotor's syndrome)), fibrosis-related diseases (such as cystic fibrosis of the pancreas and lungs, endomyocardial fibrosis, idiopathic myocardiopathy, idiopathic pulmonary fibrosis of the lung, diffuse parenchymal lung disease, mediastinal fibrosis, myelofibrosis, post-vasectomy pain syndrome, retroperitoneal fibrosis, progressive massive fibrosis, proliferative fibrosis, neoplastic fibrosis, sickle-cell anemia may cause enlargement and ultimately fibrosis of the spleen), and other clinical indications such as epilepsy, osteoporosis, rheumatoid arthritis, inflammatory bowel disease (ulcerative colitis (UC) and Crohn disease (CD), congestive obstructive pulmonary disease (COPD), inflammation, inflammatory pain, atherosclerosis, diarrhoea, asthma, constipation, skin diseases, glaucoma and hairloss.

Since obesity leads to, or significantly increases the risk of, co-morbidities involving various body systems (see Bays, 2004, Obesity Research, 12, 1197-1211) including:

i) cardiovascular (hypertension, congestive cardiomyopathy, varicosities, pulmonary embolism, coronary heart disease [CHD], neurological (stroke, idiopathic intracranial hypertension, meralgia parethetica), ii) respiratory (dyspnea, obstructive sleep apnea, hypoventilation syndrome, Pickwickian syndrome, asthma), iii) musculoskeletal (immobility, degenerative osteoarthritis, low back pain), iv) skin (striae distensae or "stretch marks," venous stasis of the lower extremities, lymphedema, cellulitis, intertrigo, carbuncles, acanthosis nigricans, skin tags), v) gastrointestinal (gastro-esophageal reflux disorder, non-alcoholic fatty liver/steatohepatitis, cholelithiasis, hernias, colon cancer), vi) genitourinary (stress incontinence, obesity-related glomerulopathy, breast and uterine cancer), vii) psychological (depression and low self-esteem, impaired quality of life), and viii) endocrine (metabolic syndrome, type 2 diabetes, dyslipidemia, hyperandrogenemia in women, polycystic ovarian syndrome, dysmenorrhea, infertility, pregnancy complications, male hypogonadism)

it is also useful to combine a CB1 modulator with medications used for treatment of such diseases. It is also useful to combine a CB1 modulator with medications used for treatment of diseases which may be unrelated to obesity such as eating disorders, addictive disorders, mental disorders, neurological disorders, sexual dysfunctions, reproductive dysfunctions, liver diseases, fibrosis-related diseases, and other clinical indications which may be unrelated to obesity.

BRIEF DESCRIPTION OF THE INVENTION

The present invention makes available a class of pyrazole compounds which modulate the activity of the cannabinoid receptor CB1. The following publications relate to other pyrazole compounds having CB1 modulatory activity:

WO1997021682, WO1997019063, WO2000046209, WO2001058869, WO200129007, WO2003088968, WO2003020217, WO2004052864, WO2005080343, WO2006067443, WO2006087480, WO 2006133926, EP00576357, EP00658546, US20030199536, US20040119972, US20040192667, US20050261281, US20050624941, US2006028084, US20060509367, J. Med. Chem. 1999 42, 769-776, Biochem. Pharmacol, 2000, 60, 1315-1323, J. Med. Chem. 2003, 46, 642-645, Bioorg & Med. Chem. Lett. 2004, 14, 2393-2395, Current Med. Chem. 2005, 12, 1361-1394.

As described herein, the compounds of the invention are useful for the treatment of obesity and overweight, prevention of weight gain, and in the treatment of diseases and conditions discussed above which benefit from suppression of the normal signalling activity of CB1 receptors. As mentioned, such diseases and conditions include obesity and overweight and those directly or indirectly associated with obesity and overweight (e.g. metabolic syndrome, type 2 diabetes, cardiovascular diseases, metabolic disorders, cancers, liver diseases, and other secondary diseases) as well as some which may be unrelated to obesity (e.g. eating disorders, addictive disorders, mental disorders, neurological disorders, sexual dysfunctions, reproductive dysfunctions, liver diseases, fibrosis-related diseases and other clinical indications). They are useful for modulating body weight and energy consumption in mammals and for modulating plasma parameters involved in the metabolic syndrome such as low HDL and/or high LDL cholesterol levels and/or small dense LDL particles, high triglyceride levels, low adiponectin levels and high HbA1c [glycosylated haemoglobin] levels and for modulating other characteristics of the metabolic syndrome such as impaired glucose tolerance, insulin resistance, excessive fat tissue in and around the abdomen, non-alcoholic fatty liver disease, steatohepatitis, steatosis, hepatic fibrosis, hepatic cirrhosis, liver tumors, metabolic liver diseases and high blood pressure.

The compounds of the invention display varying physicochemical properties and are useful for modulating peripheral CB1 receptors and to varying degree central CB1 receptors. Those compounds of the invention associated with a lowered central action on CB1 receptors may have a reduced propensity to induce psychiatric and nervous system side-effects.

DETAILED DESCRIPTION OF THE INVENTION

According to the invention there is provided a compound of formula (I) or a salt, hydrate, solvate or N-oxide thereof:

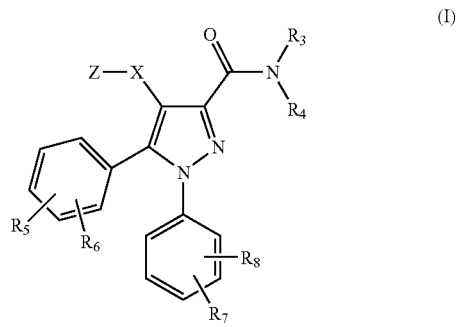

(I)

wherein:

X is a bond, or a divalent radical selected from —C($R_{10}$)($R_{11}$)—*, —C($R_{10}$)($R_{11}$)—O—*, —C($R_{10}$)($R_{11}$)CH$_2$—*, —C(R$_{10}$)(R$_{11}$)CH$_2$—O—*, —CH$_2$C(R$_{10}$)(R$_{11}$)—*, —CH$_2$C(R$_{10}$)(R$_{11}$)—O—*, and —CH$_2$—O—C(R$_{10}$)(R$_{11}$)—*, wherein the bond indicated by an asterisk is attached to the pyrazole ring;
Z is a radical selected from the group consisting of those of formulae (1)-(26) as follows:
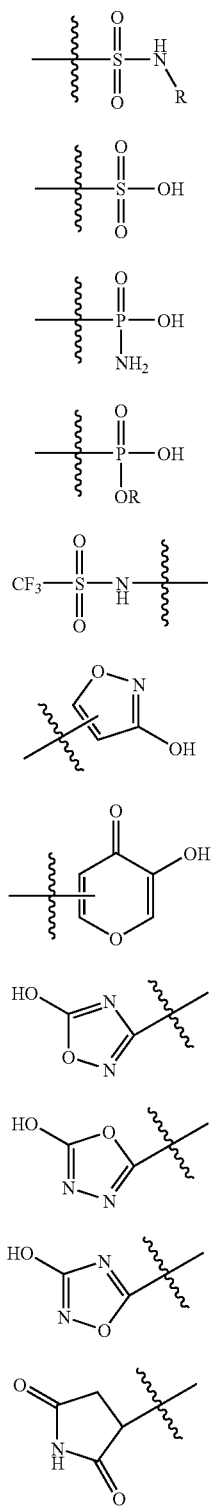
(1)
(2)
(3)
(4)
(5)
(6)
(7)
(8)
(9)
(10)
(11)
-continued
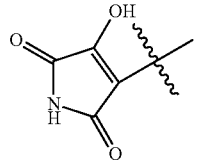
(12)
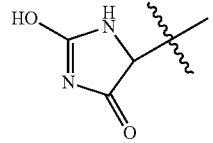
(13)
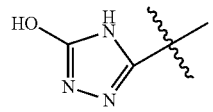
(14)
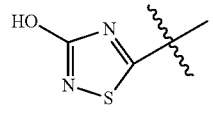
(15)
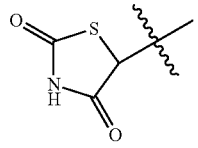
(16)
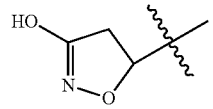
(17)
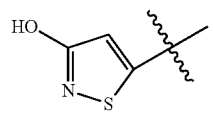
(18)
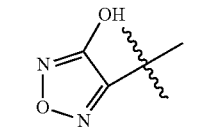
(19)
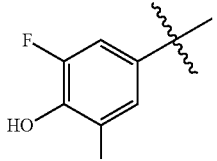
(20)
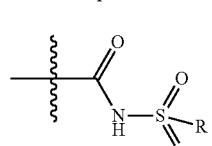
(21)
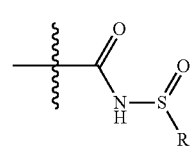
(22)

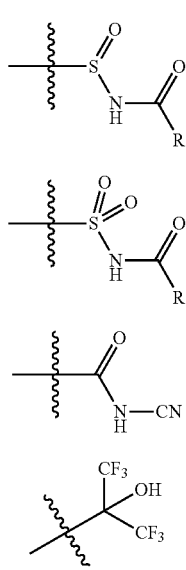

wherein R is $C_1$-$C_6$ alkyl; phenyl or benzyl optionally ring-substituted by $R_5$; or a monocyclic non-aromatic carbocyclic ring of 3 to 6 ring atoms;

$R_3$ is hydrogen, ($C_1$-$C_3$)alkyl or ($C_1$-$C_3$)fluoroalkyl;

$R_4$ is a radical of formula -$(Alk_1)_p$-$(Q_1)_r$-$(L)_s$-$Q_2$ wherein
 p, r and s are independently 0 or 1, provided that at least one of p, r and s is 1;
 $Alk_1$ is a divalent ($C_1$-$C_4$)alkylene radical which (a) is optionally substituted on one carbon by $R_{10}$ and/or $R_{11}$ or by one or two optional substituents, and/or (b) optionally contains a —O—, —S—, —CO—, —SO—, —$SO_2$—, or —$NR_9$— link;
 L is a divalent radical of formula -$(Alk_2)_n$-$(W)_m$—, in either orientation, wherein
  n and m are independently 0 or 1;
  $Alk_2$ is —C($R_{10}$)($R_{11}$)—; and
  W is —CO—, —$SO_2$—, —O—, —$NR_9$— or —SO—; provided that when W and/or $Alk_2$ are linked to a heteroatom W is not —O—, —$NR_9$— or —SO—;
 $Q_1$ is a monocyclic carbocyclic ring of 3 to 6 ring atoms, a bicyclic carbocyclic ring system of 7 to 10 ring atoms, a monocyclic heterocyclic ring of 4 to 6 ring atoms or a bicyclic carbocyclic ring system of 8 to 10 ring atoms, any of which rings or ring systems being optionally substituted;
 $Q_2$ is (a) in the case where s in -$(L)_s$-$Q_2$ is 0 or 1, a monocyclic carbocyclic ring of 3 to 6 ring atoms, a bicyclic carbocyclic ring system of 7 to 10 ring atoms, a monocyclic heterocyclic ring of 4 to 6 ring atoms or a bicyclic carbocyclic ring system of 8 to 10 ring atoms, any of which rings or ring systems being optionally substituted; or (b) only in the case where s in -$(L)_s$-$Q_2$ is 0, hydrogen;

or $R_3$ and $R_4$ taken together with the nitrogen to which they are attached form a cyclic amino ring of 4 to 7 ring atoms which is optionally substituted by a radical of formula -$(L)_s$-$Q_2$ wherein s, L and $Q_2$ are as defined above, or by an optional substituent selected from hydroxy, methoxy, —$NH_2$—, or mono- or di-($C_1$-$C_3$)alkylamino;

$R_5$, $R_6$, $R_7$ and $R_8$ are each independently selected from hydrogen —F, —Cl, —Br, —CN, ($C_1$-$C_3$)alkyl, ($C_1$-$C_3$) fluoroalkyl, cyclopropyl, and —$OR_9$;

$R_9$ is hydrogen, ($C_1$-$C_3$)alkyl, ($C_1$-$C_3$)fluoroalkyl, or ($C_3$-$C_6$) cycloalkyl; and $R_{10}$ is hydrogen, ($C_1$-$C_3$)alkyl, hydroxyl or $NH_2$, and $R_{11}$ is hydrogen or ($C_1$-$C_3$)alkyl; or $R_{10}$ and $R_{11}$ taken together with the carbon atom to which they are attached form a ($C_3$-$C_5$)cycloalkyl ring.

Another aspect of the invention is a pharmaceutical composition comprising a compound of formula (I) or a salt, hydrate, solvate or N-oxide thereof, together with one or more pharmaceutically acceptable carriers or excipients.

The compounds with which the invention is concerned suppress the normal signalling activity of cannabinoid receptor CB1. Therefore, further aspects of the invention are:

(i) The use of a compound of formula (I) or a salt, hydrate, solvate or N-oxide thereof in the preparation of a composition for treatment of diseases or conditions which are mediated by CB1 receptor signalling activity. Examples of such diseases have been listed above.; and (ii) A method for the treatment of diseases or conditions which are mediated by CB1 receptor signalling activity, which method comprises administering to a subject suffering such disease or condition an effective amount of a compound of formula (I) or a salt, hydrate, solvate or N-oxide thereof. Again, examples of such treatments have been listed above.

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "divalent ($C_a$-$C_b$)alkylene radical" wherein a and b are integers refers to a saturated straight or branched hydrocarbon chain having from a to b carbon atoms and two unsatisfied valences.

As used herein the unqualified term "carbocyclic" refers to a mono-, bi- or tricyclic radical having up to 16 ring atoms, all of which are carbon, and includes aryl and cycloalkyl.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, triazinyl, indolyl and indazolyl.

As used herein the unqualified term "heterocyclyl" or "heterocyclic" includes "heteroaryl" as defined above, and in addition means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo (including fluoro, bromo and chloro), fully or partially fluorinated ($C_1$-$C_3$)alkyl, ($C_1$-$C_3$)alkoxy or ($C_1$-$C_3$)alkylthio such as trifluoromethyl, trifluoromethoxy, and trifluoromethylthio, nitro, nitrile (—CN), oxo, phenyl, phenoxy, monocyclic heteroaryl or heteroaryloxy with 5 or 6 ring atoms, tetrazolyl, —COO$R^A$, —CO$R^A$, —OCO$R^A$, —SO$_2R^A$, —CON$R^AR^B$, —SO$_2$N$R^AR^B$, —N$R^AR^B$, OCON$R^AR^B$, —N$R^B$CO$R^A$, —N$R^B$COO$R^A$, —N$R^B$SO$_2$O$R^A$ or —N$R^A$CON$R^AR^B$ wherein $R^A$ and $R^B$ are independently hydrogen or a ($C_1$-$C_6$) alkyl group or, in the case where $R^A$ and $R^B$ are linked to the same N atom, $R^A$ and $R^B$ taken together with that nitrogen may form a cyclic amino ring, such as a morpholine, piperidinyl or piperazinyl ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl, phenoxy, heteroaryl or heteroaryloxy. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomers with R or S stereochemistry at each chiral axis. The invention includes all such enantiomers and diastereoisomers and mixtures thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, $3^{rd}$ Edition, 2002, Taylor and Francis).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985). Such examples could be a prodrug of a carboxyl group (such as —CO—O—CH$_2$—O—CO-tBu as used in the pivampicillin prodrug of ampicillin), an amide (—CO—NH—CH$_2$—NAlk$_2$) or an amidine (—C(=N—O—CH$_3$)—NH$_2$).

Also included within the scope of the invention are metabolites of compounds of formula (I), that is, compounds formed in vivo upon administration of the drug. Some examples of metabolites include (i) where the compound of formula I contains a methyl group, an hydroxymethyl derivative thereof (—CH$_3$->—CH$_2$OH):
(ii) where the compound of formula I contains an alkoxy group, an hydroxy derivative thereof (—OR->—OH);
(iii) where the compound of formula I contains a tertiary amino group, a secondary amino derivative thereof (—NR$^1$R$^2$->—NHR$^1$ or —NHR$^2$);
(iv) where the compound of formula I contains a secondary amino group, a primary derivative thereof (—NHR$^1$->—NH$_2$);
(v) where the compound of formula I contains a phenyl moiety, a phenol derivative thereof (-Ph->-PhOH); and
(vi) where the compound of formula I contains an amide group, a carboxylic acid derivative thereof (—CONH$_2$->COOH).

For use in accordance with the invention, the following structural characteristics are currently contemplated, in any compatible combination, in the compounds (I):

The Variable —X—

The divalent linker radical —X— is a bond, or a divalent radical selected from —C(R$_{10}$)(R$_{11}$)—*, —C(R$_{10}$)(R$_{11}$)—O—*, —C(R$_{10}$)(R$_{11}$)CH$_2$—*, —C(R$_{10}$)(R$_{11}$)CH$_2$—O—*, —CH$_2$C(R$_{10}$)(R$_{11}$)—*, —CH$_2$C(R$_{10}$)(R$_{11}$)—O—*, and —CH$_2$—O—C(R$_{10}$)(R$_{11}$)—*, wherein the bond indicated by an asterisk is attached to the pyrazole ring. R$_{10}$ and R$_{11}$ are independently selected from hydrogen and (C$_1$-C$_3$)alkyl (ie. methyl, ethyl and n- or isopropyl); or R$_{10}$ and R$_{11}$ taken together with the carbon atom to which they are attached form a (C$_3$-C$_5$)cycloalkyl ring such as a cyclopropyl or cyclopentyl ring. Specifically, —X— may be, for example, —CH$_2$—, —CH$_2$O—* or —CH$_2$OCH$_2$—*, wherein the bond indicated by an asterisk is attached to the pyrazole ring.

The Variable Z

Z is a radical selected from the group consisting of those of formulae (1)-(26) set out above, R is $C_1$-$C_6$ alkyl such as methyl or ethyl; a monocyclic carbocyclic ring of 3 to 6 ring atoms such as phenyl, cyclopropyl, cyclobutyl, cyclopentyl or cyclohexyl; or benzyl, The said carbocyclic rings and the phenyl ring of benzyl, may optionally be substituted by hydrogen —F, —Cl, —Br, —CN, ($C_1$-$C_3$)alkyl such as methyl or ethyl, ($C_1$-$C_3$)fluoroalkyl such as trifluoromethyl, cyclopropyl, ($C_1$-$C_3$)alkoxy such as methozy or ethoxy, ($C_1$-$C_3$)fluoroalkoxy such as trifluoromethoxy, or ($C_3$-$C_6$)cycloalkyloxy such as cyclopropyloxy, cyclopentyloxy or cyclohexyloxy. Formulae (1)-(26) form a coherent group in that they may all loosely be regarded as bioisosteres of a carboxylic acid group or of a tetrazolyl group (which itself is regarded as a bioisostere of a carboxyl group). Such bioisosteres are described in the literature, see for example Olessen, P. H. *Current Opinion in Drug Discovery and Development* (2001), 4, 471; Wermuth, C. G. "Molecular Variations Based on Isosteric Replacements"; Practice of Medicinal Chemistry; Wermerth, C., Ed.; Academic Press, (2003), pp 189-214; Ruble, J. et al; "Structure-activity relationships of bioisosteres of a carboxylic acid in a novel class of bacterial translation inhibitors". *Bioorganic & Medicinal Chemistry Letters* (2007), 17 4040-4043; Rönn, R. et al; "Evaluation of a diverse set of potential P1 carboxylic acid bioisosteres in hepatitis C virus NS3 protease inhibitors". *Bioorganic & Medicinal Chemistry* (2007), 15, 4057-4068; Macchiarulo, A.; Pellicciari, R. "Exploring the other side of biologically relevant chemical space: Insights into carboxylic, sulfonic and phosphonic acid bioisosteric relationships". *Journal of Molecular Graphics & Modelling* (2007), 26, 728-739; Lolli, M. L. et al. "Hydroxy-1,2,5-oxadiazolyl Moiety as Bioisostere of the Carboxy Function. Synthesis, Ionization Constants, and Pharmacological Characterization of γ-Aminobutyric Acid (GABA) Related Compounds". *Journal of Medicinal Chemistry* (2006), 49, 4442-4446; Valgeirsson, J. et al. "Bioisosteric Modifications of 2-Arylureidobenzoic Acids: Selective Noncompetitive Antagonists for the Homomeric Kainate Receptor Subtype GluR5". *Journal of Medicinal Chemistry* (2004), 47, 6948-6957; Nicolaou, I. et al. "[1-(3,5-Difluoro-4-hydroxyphenyl)-1H-pyrrol-3-yl]phenylmethanone as a Bioisostere of a Carboxylic Acid Aldose Reductase Inhibitor". *Journal of Medicinal Chemistry* (2004), 47, 2706-2709; Ornstein, P. et al. "Structure-Activity Studies of 6-Substituted Decahydroisoquinoline-3-carboxylic Acid AMPA Receptor Antagonists. 2. Effects of Distal Acid Bioisosteric Substitution, Absolute Stereochemical Preferences, and in Vivo Activity". *Journal of Medicinal Chemistry* (1996), 39, 2232-44; Kohara, Y. Et al. "A new class of angiotensin II receptor antagonists with a novel acidic bioisostere". *Bioorganic & Medicinal Chemistry Letters* (1995), 5, 1903-8.

It will be apparent that some of the radicals (1)-(26) above can exist in tautomeric equilibrium, and that all such tautomers are to be considered included in the formulae (1)-(26). For example, the tautomeric forms of radicals (13) and (9) are as follows:

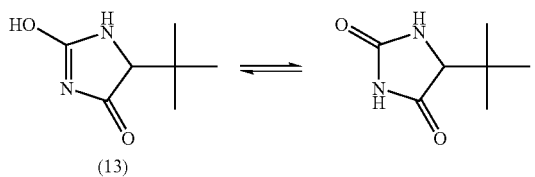

(13)

-continued

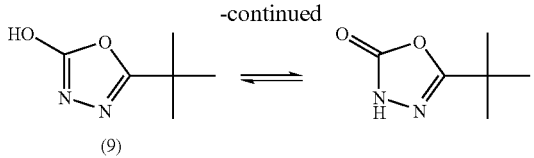

(9)

The Substituent $R_3$ $R_3$ is hydrogen, ($C_1$-$C_3$)alkyl such as methyl or ethyl or ($C_1$-$C_3$)fluoroalkyl such as di- or trifluoromethyl. $R_3$ will often be hydrogen.

The Substituent $R_4$

As will be apparent from its definition above, a great diversity of substituents may be present in compounds of the invention.

$R_4$ has formula -$(Alk_1)_p$-$(Q_1)_r$-$(L)_s$-$Q_2$ wherein p, r and s are 0 or 1 in any compatible combination, provided that at least one of p, r and s is 1. In one particular type of compound of the invention p and s are 0, and r is 1, and in another p and r are 1 and s is 0 or 1.

In $R_4$. $Alk_1$ when present is a divalent ($C_1$-$C_4$)alkylene radical which (a) is optionally substituted on one carbon by $R_{10}$ and/or $R_{11}$ or by one or two optional substituents, and/or (b) optionally contains a —O—, —S—, —CO—, —SO—, —$SO_2$—, or —$NR_9$— link. In this context, $R_{10}$ and $R_{11}$ may be, for example, methyl; or $R_{10}$ and $R_{11}$ taken together with the carbon atom to which they are attached may form, for example, a cyclopropyl or cyclopentyl ring. Optional substituents in this context include fluoro and hydroxyl.

Examples of such radicals include —$CH_2$—, —$CH_2CH_2$— —$CH_2CH_2CH_2$—, —$CH_2CH_2CH_2CH_2$—, —$CH_2T$—, —$CH_2TCH_2$— —$CH_2CH_2TCH_2$—, —$CH_2CH_2TCH(CH_3)$—, —$CH_2TCH_2CH_2$—, and —$CH_2TCH_2CH_2WCH_2$—, where T is —O—, —S—, —NH—, or —N($CH_3$)—, and any of the foregoing wherein one or more hydrogens are exchanged for fluorines, and/or wherein one or two carbons are substituted by methyl or, trifluoromethyl; or wherein one carbon is substituted by a spiro-linked cyclopropyl substituent.

In the compounds of the invention, $Alk_1$, when present will often be simply —$CH_2$—.

In $R_4$, L when present is a divalent radical of formula -$(Alk_2)_n$—$(W)_m$—, in either orientation, wherein n and m are independently 0 or 1; $Alk_2$ is —$C(R_{10})(R_{11})$—; and W is —CO—, —$SO_2$—, —O—, —$NR_9$— or —SO—; provided that when W and/or $Alk_2$ are linked to a heteroatom W is not —O—, —$NR_9$— or —SO—. The latter restriction is in order to avoid unstable or undesirable potential structures. In this context, $R_9$ may be, for example, hydrogen or methyl. Examples of $Alk_2$, when present are —$CH_2$—, —CH($CH_3$)—, a cyclopropyl ring which is linked to each adjacent atom via the same ring carbon, and, in either orientation —$CH_2$O—, —$CH_2NH$—, —CH($CH_3$)O— and —CH($CH_3$)NH—.

In $R_4$, $Q_1$ (when present) and $Q_2$ are each independently a monocyclic carbocyclic radical of 3 to 7 ring atoms, a bicyclic carbocyclic ring system of 7 to 10 ring atoms, a monocyclic heterocyclic ring of 4 to 7 ring atoms or a bicyclic carbocyclic ring system of 8 to 10 ring atoms, any of which rings or ring systems being optionally substituted; $Q_2$ may also be hydrogen when s in -$(L)_s$-$Q_2$ is 0; Examples of $Q_1$, when present, include optionally substituted divalent phenyl, pyridine, piperidine, piperazine or ($C_3$-$C_7$)cycloalkyl, eg cyclohexyl, cyclopentyl or cyclopropyl, radicals. Examples of $Q_2$ include hydrogen, or optionally substituted phenyl or pyridyl. Optional substituents in rings $Q_1$ and $Q_2$ include —F, —Cl, —Br, —CN, —CF$_3$, —CH$_3$, cyclopropyl, and —OCH$_3$, and may be present on, for example 1 or 2 ring atoms.

The Groups R$_3$ and R$_4$ Together

In other types of compound of the invention, R$_3$ and R$_4$ taken together with the nitrogen to which they are attached form a cyclic amino ring of 4 to 7 ring atoms. Examples of such rings include morpholinyl, pyrrolidinyl, piperidinyl, azepanyl and piperazinyl.

The ring formed by R$_3$ and R$_4$ taken together with the nitrogen to which they are attached may be substituted by a radical of formula -(L)$_s$-Q$_2$ wherein s, L and Q$_2$ are as defined and discussed above, or by an optional substituent selected from hydroxy, methoxy, —NH$_2$—, or mono- or di-(C$_1$-C$_3$) alkylamino such as methylamino, ethylamino, dimethylamino and diethylamino.

Specific examples of the radical —C(=O)NR$_3$R$_4$ include those of formulae (A)-(R) and (X1)-(X12):

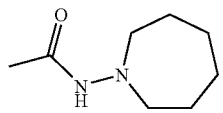 (A)

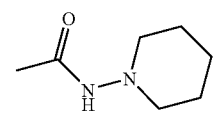 (B)

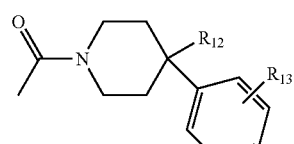 (C)

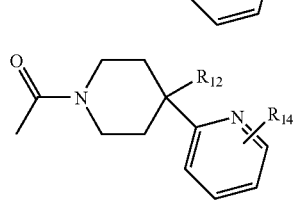 (D)

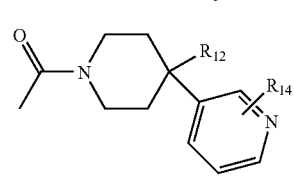 (E)

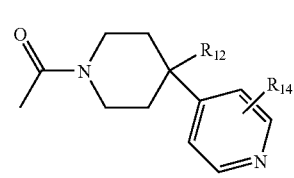 (F)

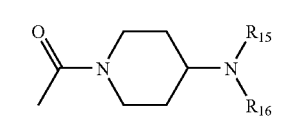 (G)

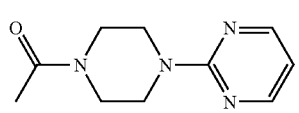 (H)

-continued

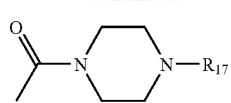 (J)

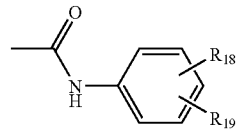 (K)

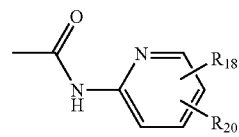 (L)

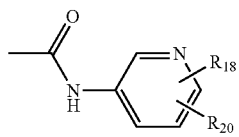 (M)

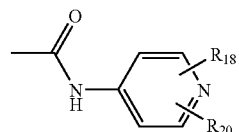 (N)

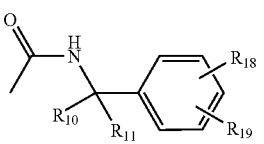 (O)

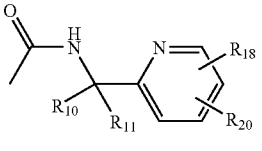 (P)

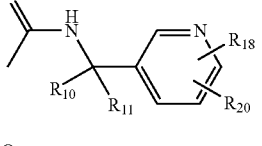 (Q)

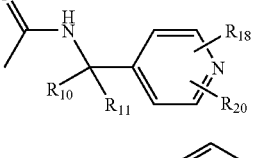 (R)

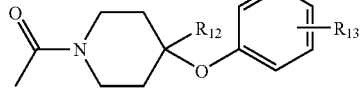 (X1)

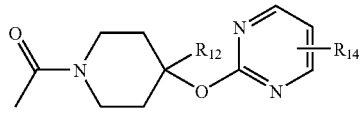 (X2)

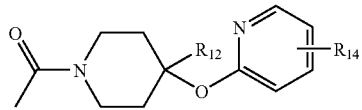 (X3)

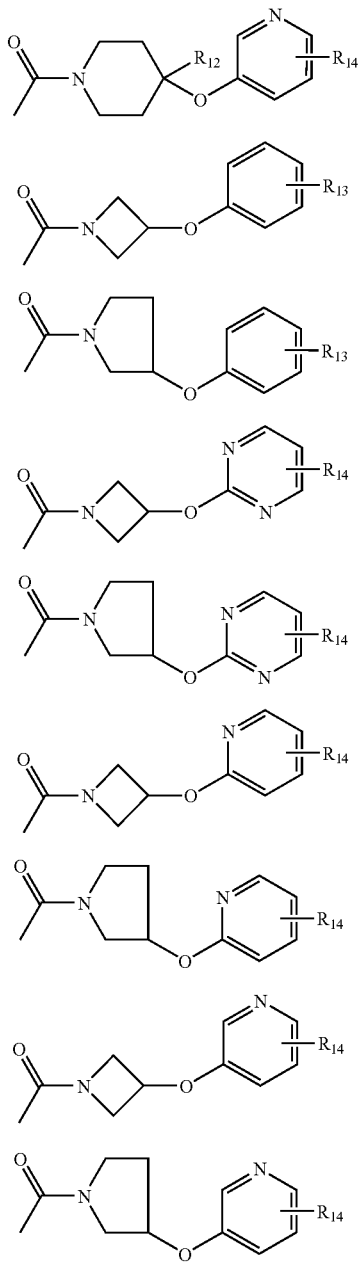

wherein
R$_{10}$ and R$_{11}$ are as defined herein;
R$_{12}$ is selected from hydrogen, —CH$_3$, —OH, —CN and —COOH;
R$_{13}$ is selected from hydrogen, —F, —CF$_3$, —OCF$_3$, —Br, —Cl, —OCH$_3$, —CH$_3$, and —CN;
R$_{14}$ is selected from hydrogen, —F, —CF$_3$, —OCF$_3$, —Br, —Cl, —OCH$_3$, —CH$_3$, —CN, and —OH;
R$_{15}$ and R$_{16}$ are independently selected from hydrogen and (C$_1$-C$_6$)alkyl or R$_{15}$ and R$_{16}$ taken together with the nitrogen to which they are attached form a cyclic amino ring of 4 to 7 ring atoms;
R$_{17}$ is selected from hydrogen, (C$_1$-C$_6$)alkyl, (C$_1$-C$_6$)alkylC(=O)—, (C$_1$-C$_6$)alkylSO$_2$—, benzyloxycarbonyl-, and —C(=O)OCH$_3$;
R$_{18}$ is selected from hydrogen, —F and —CN;

R$_{19}$ is selected from hydrogen, F, —CF$_3$, —OCF$_3$, —Br, —Cl, —OCH$_3$, —CH$_3$, and —CN; and
R$_{20}$ is selected from hydrogen, F, —CF$_3$, —OCF$_3$, —Br, —Cl, —OCH$_3$, —CH$_3$, —CN, and —OH.

With reference to the above formulae (A)-(R) and (X1)-(X12) any substituents in a heteroaromatic ring must of course be consistent with known medicinal chemistry principles. For example, it is unlikely that any substitutent halogen or CN in a nitrogen-containing heteroaromatic ring will be adjacent to the nitrogen atom, since such substituent is expected to behave as a good leaving group, implying that in vivo such compounds would have a strong potential to react with nucleophilic entities, leading to covalent bond formation, generally regarded as undesirable for potential toxicicty reasons. Also for example, it is likely that any OH substituent will be adjacent to the nitrogen atom since again such compounds can lead to potential toxicity.

The Substituents R$_5$, R$_6$, R$_7$ and R$_8$

R$_5$, R$_6$, R$_7$ and R$_8$ are each independently selected from hydrogen —F, —Cl, —Br, —CN, (C$_1$-C$_3$)alkyl such as methyl or ethyl, (C$_1$-C$_3$)fluoroalkyl such as di- or trifluoromethyl, and —OR$_9$ wherein R$_9$ is hydrogen, (C$_1$-C$_3$)alkyl such as methyl or ethyl, (C$_1$-C$_3$)fluoroalkyl such as di- or trifluoromethyl, and cyclopropyl. In many cases, R$_5$, R$_6$, R$_7$ and R$_8$ will be independently selected from hydrogen and —Cl, The Substituents R$_{10}$ and R$_{11}$ R$_{10}$ is hydrogen, (C$_1$-C$_3$)alkyl, hydroxyl or NH$_2$, and R$_{11}$ is hydrogen or (C$_1$-C$_3$)alkyl. In many cases, both R$_{10}$ and R$_{11}$ are hydrogen, or one of R$_{10}$ and R$_{11}$ is hydrogen while the other is methyl.

Specific compounds of the invention include those of the Examples herein.

The compounds of the present invention act on central and peripheral cannabinoid receptor CB1. Some compounds distribute to a lesser extent to the central nervous system, i.e. the compound less readily crosses the blood-brain barrier and will be associated with fewer central nervous system mediated side-effects.

The compounds of the invention modulate the cannabinoid receptor CB1 by suppressing its natural signalling function. The compounds are therefore CB1 receptor antagonists, inverse agonists, or partial agonists.

The term "CB1 antagonist" or "cannabinoid receptor CB1 antagonist" refers to a compound which binds to the receptor, or in its vicinity, and lacks any substantial ability to activate the receptor itself. A CB1 antagonist can thereby prevent or reduce the functional activation or occupation of the receptor by a CB1 agonist such as for example the endogenous agonist N-Arachidonylethanolamine (anandamide). This term is well known in the art.

The term "CB1 inverse agonist" or "cannabinoid receptor CB1 inverse agonist" refers to a compound which binds to the receptor and exerts the opposite pharmacological effect as a CB1 receptor agonist does. Inverse agonists are effective against certain types of receptors which have intrinsic activity without the acting of a ligand upon them (also referred to as 'constitutive activity'). This term is well known in the art. It is also well known in the art that such a CB1 inverse agonist can also be named a CB1 antagonist as the general properties of both types are equivalent. Accordingly, in the context of the present invention the term "CB1 antagonist" in general is understood as including both the "CB1 antagonist" as defined above and the "CB1 inverse agonist".

The term "CB1 partial agonist" or "cannabinoid receptor CB1 partial agonist" refers to a compound which acts upon the same receptor as the full agonist but that produces a weak maximum pharmacological response and has a low level of intrinsic activity. This term is well known in the art.

According to a preferred embodiment of the present invention, the "CB1 modulator" or "cannabinoid receptor CB1 modulator" is a CB1 antagonist or inverse agonist compound.

The compounds of the invention are useful for the treatment of diseases or conditions which are mediated by CB1 receptor signalling activity. Examples of such diseases and conditions and treatments therefor have been listed above. Without limitation, they include obesity and overweight, prevention of weight gain, treatment of diseases and conditions directly or indirectly associated with obesity (e.g. metabolic syndrome, type 2 diabetes, cardiovascular diseases, metabolic dysfunctions in obese, overweight or normoweight individuals, metabolic diseases or disorders, cancers, liver diseases and the other secondary diseases referred to above), and in the treatment of diseases and conditions not necessarily related to obesity (e.g. eating disorders, addictive disorders, mental disorders, neurological disorders, sexual dysfunctions, reproductive dysfunctions, liver diseases, fibrosis-related diseases and other clinical indications referred to above). They are useful for modulating body weight and energy consumption in mammals and for modulating major components involved in the metabolic syndrome such as excess abdominal fat, atherogenic dyslipidemia (abnormal levels of HDL-C, triglycerides, LDL, apolipoprotein B, adiponectin), hypertension, hyperglycaemia, hyperuricaemia, non-alcoholic fatty liver disease/hepatic steatosis, elevated liver transaminases, gamma-glutamyl-transferase and microalbuminuria.

The compounds of the invention display varying physicochemical properties and are useful for modulating peripheral CB1 receptors and to varying degree central CB1 receptors. Those compounds of the invention associated with a lowered central action on CB1 receptors may have a reduced propensity to induce psychiatric and nervous system side-effects.

The compounds of the invention may be combined with another therapeutic agent used in treatment of obesity acting by a different mode of action such as central action on satiety or hunger signals, craving mechanisms, appetite regulation, leptin/insulin/central nervous system pathways, gastrointestinal-neural pathways, metabolic rate, energy expenditure, food intake, fat storage, fat excretion, gastrointestinal motility, lipogenesis, glucose transport, glucogenolysis, glycolysis, lipolysis, etc including modulators (inhibitors, agonists, antagonists, analogues) of monoaminergic (NA (noradrenaline), 5-HT (serotonin), DA (dopamine)) receptors or transporters, neural ion channels, leptin or leptin receptor, neuropeptide Y receptors, PP (pancreatic polypeptide), PYY, Protein YY3-36, ghrelin or ghrelin receptor, motilin or motilin receptor, orexins or orexin receptors, bombesin or bombesin-like peptide receptors, somatostatin or somatostatin receptors, MCHR1 (melanin concentrating hormone receptor 1), CNTF (ciliary neurotrophic factor), AgRP (agouti-related peptide), POMC (proopiomelanocortin), CART (cocaine and amphetamine regulated transcript), alpha-MSH (alpha-melanocyte-stimulating hormone), MC4 (melanocortin-4) or MC3 (melanocortin-3) receptor, galanin receptors, relaxin-3 receptor, GPR7 receptor, GPR119 receptor, GPR10 receptor, neuromedin U receptors, free-fatty-acid receptors, growth hormone, nesfatin-1, opioid receptors, neuropeptide FF receptors, PTP-1B (protein-tyrosine phosphatase), PPAR (peroxisome proliferators activated receptors) receptors, retinoid X receptor heterodimers, adiponectin also known as Acrp30 (adipocyte complement-related protein of 30 kDa), fatty acid metabolism, H (histamine) receptors, CCK-A (Cholecystokinin-A) or CCK-A receptor, GLP-1 (glucagon-like peptide-1) or GLP-1 receptor, oxyntomodulin, adrenomedullin, DPP-IV (dipeptidyl peptidase IV), amylin, beta-3-adrenergic receptor, UCP (uncoupling protein), thyroid receptor, thyroid-stimulating hormone receptor, 11beta-hydroxysteroid dehydrogenase type 1, amylase, DHEAS (dehydroepiandrosterone sulfate), CRH (corticotropin releasing hormone) or CRH receptors, carboxypeptidase, fatty acid synthesis, HMG-CoA reductase, ileal bile acid transport, gastrointestinal lipase, P57, AMP-activated protein kinase (AMPK).

The compounds of the invention may be combined with another therapeutic agent used in treatment of metabolic syndrome or of diseases which may be directly or indirectly associated with obesity such as cardiovascular (hypertension, cardiomyopathy, varicosities, pulmonary embolism, venous thromboembolism, coronary heart disease [CHD], aneurysms, angina, arrhythmia, atherosclerosis, cerebrovascular disease, congenital heart disease, congestive heart failure, myocarditis, valve disease, coronary artery disease, diastolic dysfunction, endocarditis, mitral valve prolapse, myocardial infarction, thrombosis), liver (non-alcoholic fatty liver disease, steatohepatitis, steatosis, hepatic fibrosis, hepatic cirrhosis), neurological (stroke, idiopathic intracranial hypertension, meralgia parethetica, headache, carpal tunnel syndrome, dementia), respiratory (dyspnea, obstructive sleep apnea, hypoventilation syndrome, Pickwickian syndrome, asthma), musculoskeletal (immobility, degenerative osteoarthritis, low back pain, osteoporosis), skin (striae distensae or "stretch marks," venous stasis of the lower extremities, lymphedema, cellulitis, intertrigo, carbuncles, acanthosis nigricans, skin tags), gastrointestinal (gastro-esophageal reflux disorder, nonalcoholic fatty liver/steatohepatitis, cholelithiasis, hernias, colon cancer, colorectal cancer), genitourinary (stress incontinence, obesity-related glomerulopathy, chronic renal failure, stillbirth, breast and uterine cancer), psychological (depression and low self-esteem, impaired quality of life, social stigmatization, body dysmorphic disorder) and endocrine (metabolic syndrome, type 2 diabetes, diabetes mellitus, dyslipidemia, hyperlipidemia, low HDL and/or high LDL cholesterol levels, hypertriglycerideemia, low adiponectin levels, impaired glucose tolerance, insulin resistance, increase in HbA1c levels, reduced metabolic activity, hyperandrogenemia in women, polycystic ovarian syndrome, dysmenorrhea, infertility, pregnancy complications, male hypogonadism, hyperuricemia, menstrual disorders, gallstones, hypogonadism, lymphedema) diseases.

Use of the compounds of the invention may be combined with proper reduction in dietary calorie intake and physical exercise.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. However, for administration to human patients, the total daily dose of the compounds of the invention may typically be in the range 1 mg to 1000 mg depending, of course, on the mode of administration. For example, oral administration may require a total daily dose of from 10 mg to 1000 mg, while an intravenous dose may only require from 1 mg to 500 mg. The total daily dose may be administered in single or divided doses and may, at the physician's discretion, fall outside of the typical range given herein.

These dosages are based on an average human subject having a weight of about 60 kg to 100 kg. The physician will readily be able to determine doses for subjects whose weight falls outside this range, such as infants and the elderly, and especially obese patients.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4*th* Edition (Wiley), J March, "*Comprehensive Organic Transformation*", 2*nd* Edition (Wiley), R. C. Larock, "*Handbook of Heterocyclic Chemistry*", 2*nd* Edition (Pergamon), A. R. Katritzky, P. G. M. Wuts and T. W. Greene "Greene's Protective Groups in Organic Chemistry" 4*th* Edition (Wiley) review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

General Synthetic Routes

Routes outlined below do not constitute an exhaustive list.

Experimental conditions given are generic and can be found in standard literature sources such as those cited above. Specific references are cited for information and conditions may apply to a given substrate with or without modification/optimization.

The compounds of Formula (I) may be obtained by introduction of the —N(R$_3$)R$_4$ moiety to a corresponding carboxylic acid or a protected form of the depicted carboxylic acid as outlined in the following scheme:

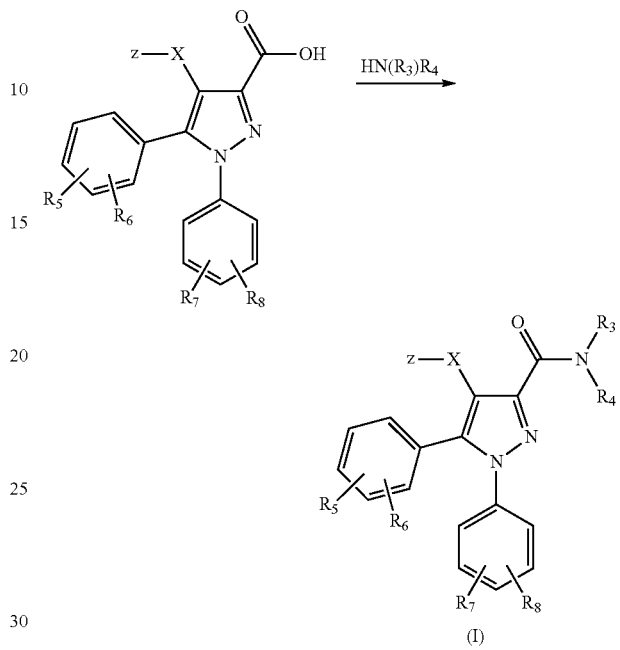

Thus, the HN(R$_3$)R$_4$ moiety contains a nucleophilic nitrogen center and the remaining part could include the final substituent, a protected version of the substituent or a group which can be converted to the final substituent using standard procedures known to those skilled in the art. Thus, compounds of Formula I may either be obtained directly following the procedure in scheme A or after standard conversions such as removal of protecting groups.

The carboxylic acids can be in activated forms (e.g. acid chlorides or active esters) or alternatively the conversion can be made directly from the acid using suitable coupling reagents such as dicyclohexylcarbodiimide (DCC), and promoters such as 1-hydroxybenzotriazole (HOBT).

Compounds of Formula (I) can also be obtained by following a related procedure to that described above whereupon a carboxylic acid derivative (e.g. nitrile, ester or amide), or other suitable precursor is converted into the group Z (in a one or multiple-step synthesis) after the amide formation. For instance as outlined in the following scheme:

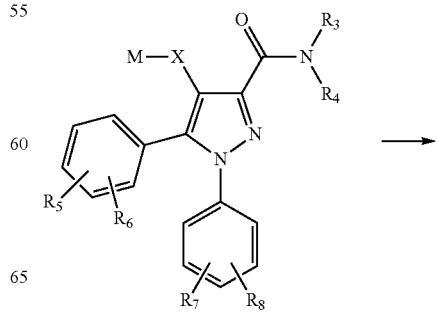

-continued

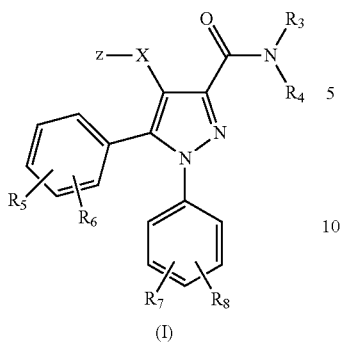

(I)

M = CO₂W, Br, CN wherein W = e.g. H, Methyl, Ethyl, Cl, NH₂, NHOH

-continued

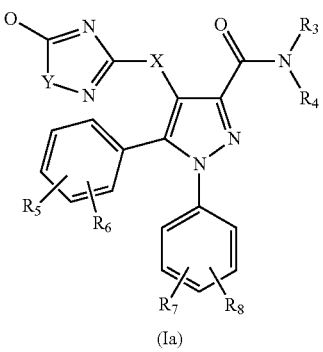

(Ia)

Y = O, NH

Such a procedure may include for instance conversion of a nitrile group to:

a— a [1,2,4]triazol-3-ol (Y=NH) or an [1,2,4]oxadiazol-5-ol (Y=O) to give compounds of general formula (Ia):

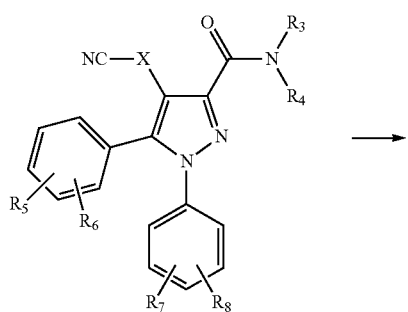

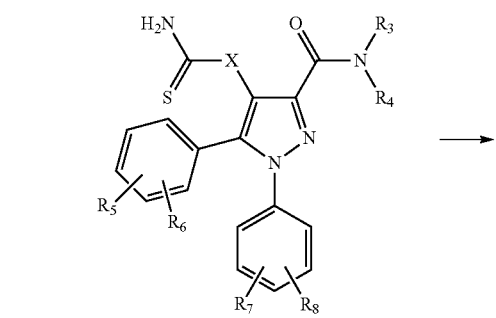

Thus, the nitrile group may first be converted to a thioamide by treatment with hydrogen sulfide and a base such as triethylamine in pyridine. Upon reaction with either hydrazine or hydroxylamine, the thioamide may be respectively converted to amidrazone or amidoxime intermediates. Cyclization of the amidrazone or amidoxime intermediates to respectively give [1,2,4]triazol-3-ols or [1,2,4]oxadiazol-5-ols of formula (Ia) may be achieved by treatment with an appropriate activating agent (e.g. phosgene, triphosgene, carbonyldiimidazole, ethylchloroformate in an aprotic polar solvent such as THF) in the presence or not of a base, at room temperature or under heating conditions. See experimental section for detailed description and *Bioorganic & Medicinal Chemistry*, 14(21), 7324-7332; 2006; *European Journal of Medicinal Chemistry*, 28(6), 513-16; 1993.

b— a hydantoin to give compounds of general formula (Ib):

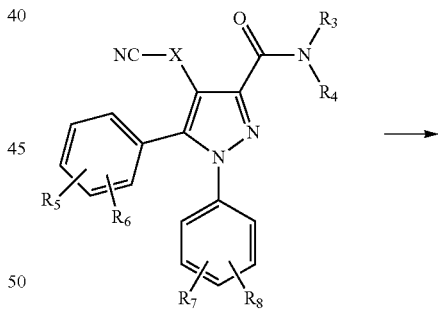

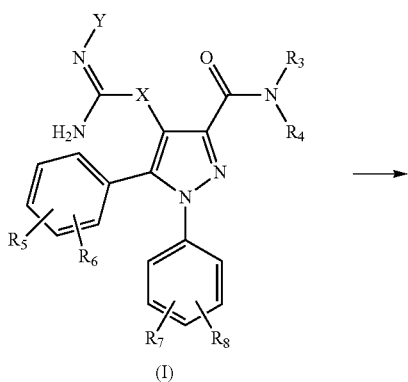

(I)

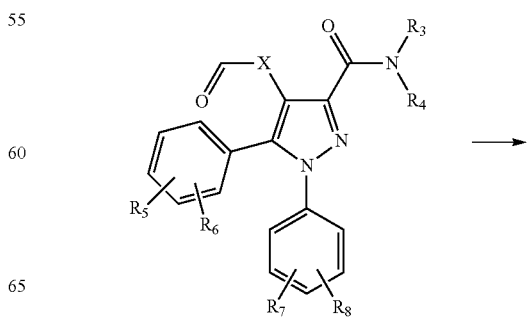

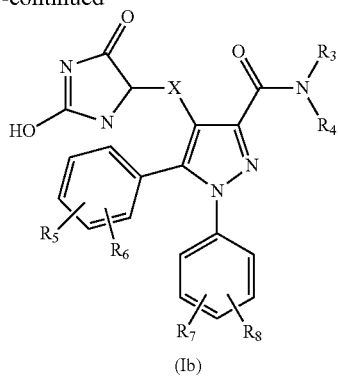

(Ib)

Thus, the nitrile group may first be reduced to an aldehyde by treatment with first a reducing agent such as diisobutyl aluminum hydride and then the ring forming reagents potassium cyanide and ammonium carbonate (e.g. Bucherer-Bergs reaction) to give hydantoins of general formula (Ib).

Alternatively, the nitrile group can be converted to hydantoins of general formula (Ib) in a one-pot procedure by treatment with organometallic reagents (such as RLi or RMgX) followed by potassium cyanide and ammonium carbonate. See *Bioorganic & Medicinal Chemistry Letters*, (2005), 15(22), 5039-5044; *Synlett*, (14), 2203-2206; 2006.

c— a thiazolidine-2,4-dione to give compounds of general formula (Ic):

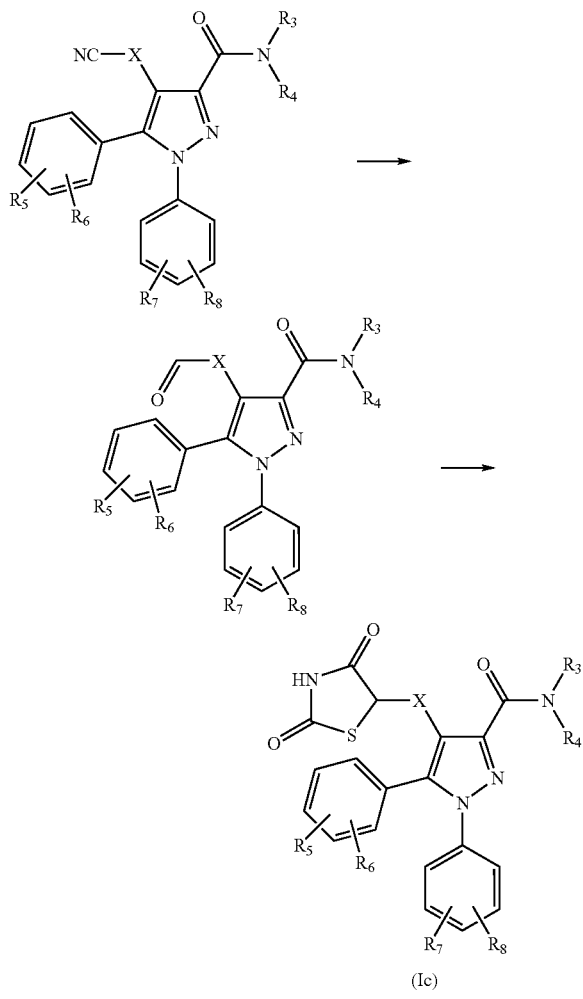

(Ic)

The nitrile group may first be reduced to an aldehyde by treatment of a reducing agent such as diisobutyl aluminum hydride. The aldehyde is then transformed to a hydroxyacetic acid methyl ester using trimethylsilyl cyanide and methanol in acid conditions e.g. HCl. This α-hydroxyl ester is activated by treatment with sulfinyl chloride in the presence of pyridine and reacted with thiourea to give, after hydrolysis, the thiazolidine-2,4-diones of general formula (Ic). See; *Bioorganic & Medicinal Chemistry* (2005), 13(11), 3627-3639.

Such a procedure may also include for instance conversion of a derivative of formula $CO_2W$ to:

d— an acyl sulfonamide (Z=R—SO2-NH—) or acyl cyanamide (Z=CN—NH—) to give compounds of general formula (Id):

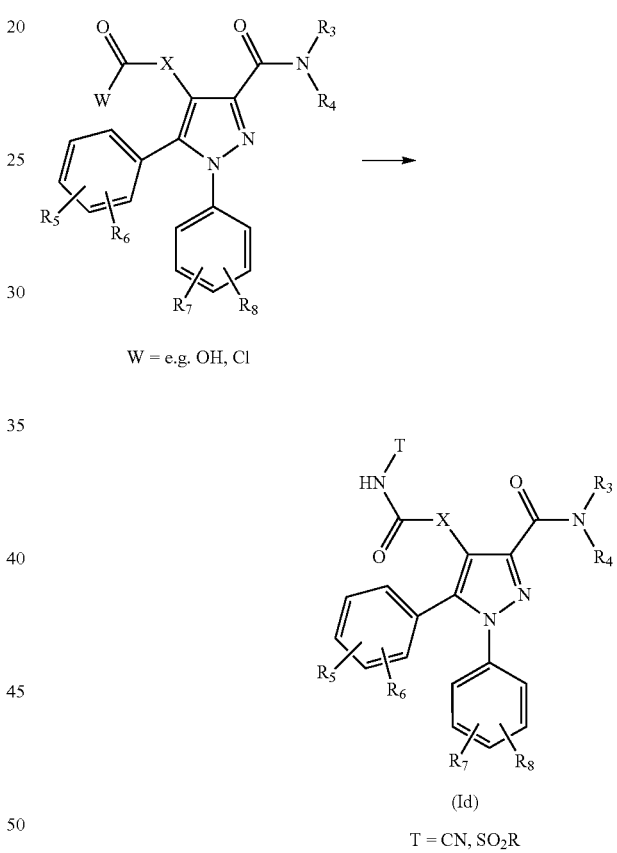

(Id)

T = CN, $SO_2R$

The carboxylic acid group can be in activated forms (e.g. acid chlorides or active esters) or alternatively the conversion can be made directly from the acid using suitable coupling reagents such as dicyclohexylcarbodiimide (DCC), and promoters such as 1-hydroxybenzotriazole (HOBT). Reaction of the activated carboxylic acid group with an alkyl/aryl sulfonamide or cyanamide may be achieved in e.g. dichloromethane in presence of a base e.g. diisopropylethylamine, at room temperature, to respectively give acyl sulfonamides and acyl cyanamides of general formula (Id). See experimental section for detailed description.

e— a 3H-[1,3,4]oxadiazol-2-one to give compounds of general formula (Ie):

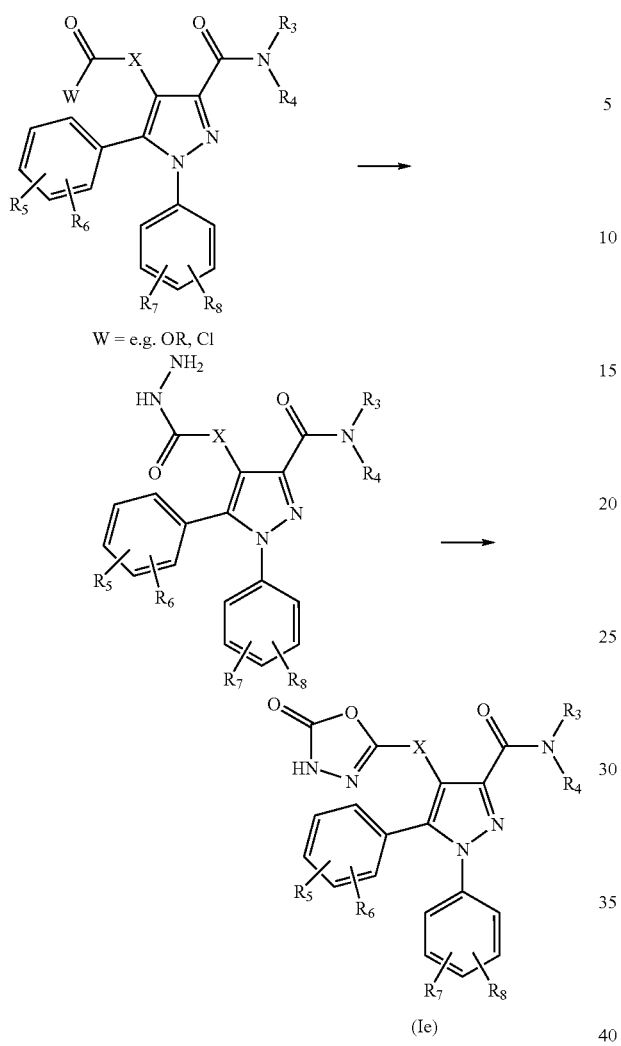

(Ie)

Thus, the ester group may first be converted to an acid hydrazide by treatment with hydrazine under heating conditions. Cyclization of the intermediate to give 3H-[1,3,4]oxadiazol-2-ones of formula (Ie) may be achieved by treatment with an appropriate activating agent (e.g. phosgene, chloroformates, carbonyldiimidazole, Diethyl dicarbonate in an aprotic polar solvent such as THF) in the presence or not of a base, at room temperature or under heating conditions. See experimental section for detailed description.

f— an isoxazol-3-ol to give compounds of general formula (If):

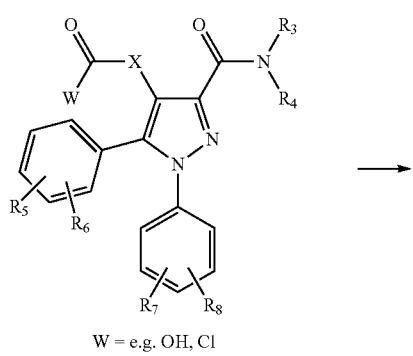

W = e.g. OH, Cl

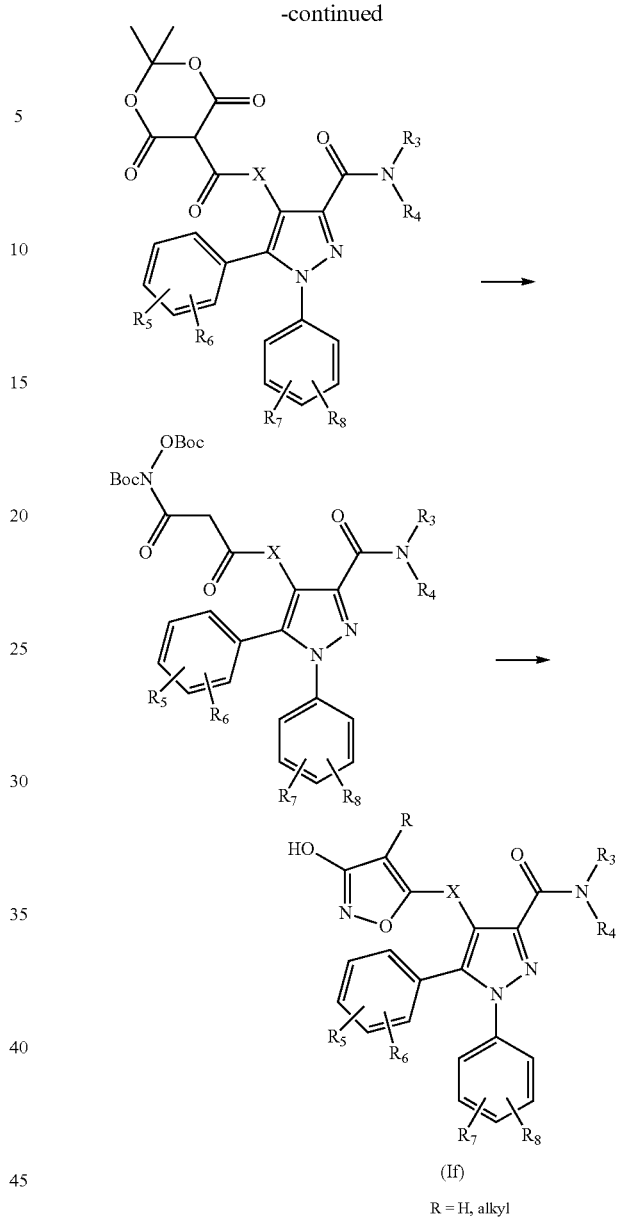

(If)

R = H, alkyl

The carboxylic acid group can be in activated forms (e.g. acid chlorides or active esters) or alternatively the conversion can be made directly from the acid using suitable coupling reagents such as dicyclohexylcarbodiimide (DCC), and promoters such as 1-hydroxybenzotriazole (HOBT).

Thus, the activated carboxylic acid group can be first converted into an acyl Meldrum's acid that upon aminolysis with N,O-bis(tert-butoxycarbonyl)hydroxylamine affords an intermediate which cyclizes in the presence of hydrochloric acid in e.g. methanol to form a 3-isoxazolol (R=H) of general formula (Ie). Alternatively, the intermediate can be treated with a strong base e.g. LDA and an alkylating agent e.g. Alkyl halide in order to introduce chemical diversity at the methylene position. Cyclization of the alkylated intermediate as described above leads to 4-alkyl-isoxazol-3-ols (R=alkyl) of general formula (If). See *Journal of Organic Chemistry* (2000), 65(4), 1003-1007; *Bioorganic & Medicinal Chemistry Letters*, 15(18), 4053-4056; 2005 g— an [1,2,4]oxadiazole-3-ol to give compounds of general formula (Ig):

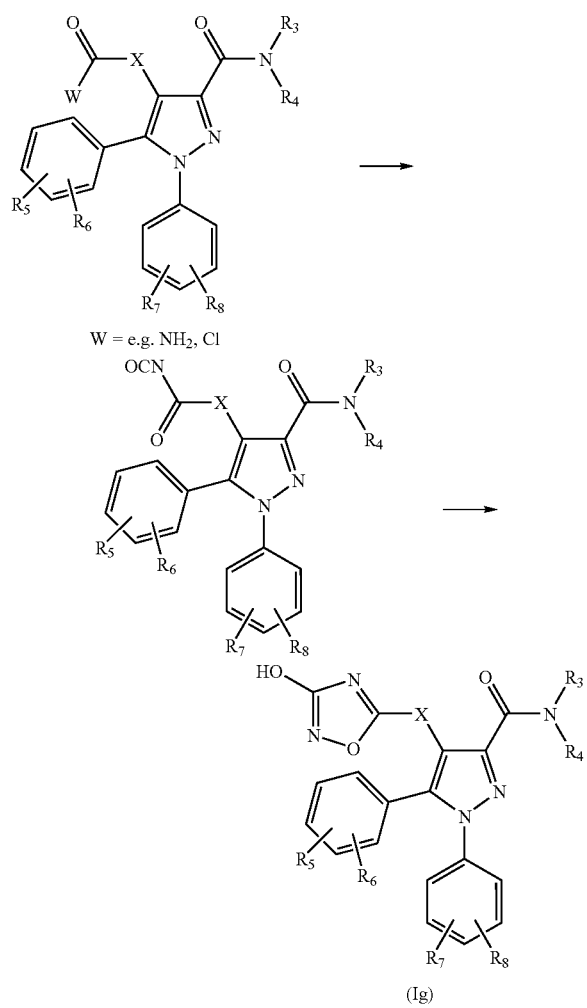

W = e.g. NH₂, Cl (Ig)

Thus, an activated form of the carboxylic acid moiety (e.g. acid chloride) may be converted to an acyl isocyanate by treatment with silver isocyanate in e.g. diethylether.

Alternatively, the acyl isocyanate can be synthesized from a primary amide upon reaction with oxalyl chloride in e.g. dichloromethane or dichloroethane.

The acyl isocyanate intermediate can then be reacted with hydroxylamine hydrochloride in pyridine to give [1,2,4]oxadiazole-3-ols of general formula (Ig). See *Tetrahedron*, 31(17), 2007-14; 1975; *Eur. Pat. Appl.*, 585165, 2 Mar. 1994; *Organic Letters*, 6(15), 2571-2574; 2004.

h— a trifluoromethylsulfonamide to give compounds of general formula (Ih):

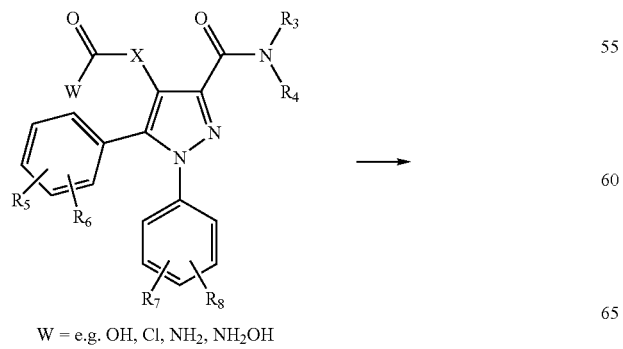

W = e.g. OH, Cl, NH₂, NH₂OH

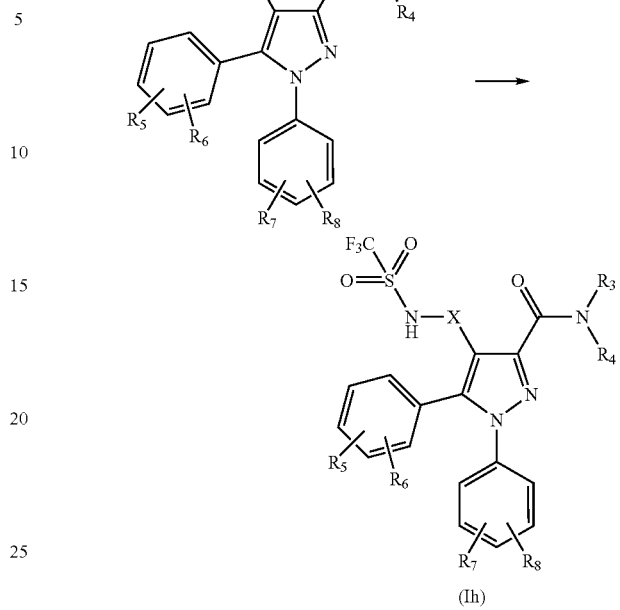

(Ih)

Thus, the carboxylic acid or amide group may be converted to a primary amine intermediate (according to well know procedures e.g. Curtius, Lossen or Hofmann rearrangements) which may then be reacted with trifluoromethanesulfonic anhydride in e.g. dichloromethane in presence of a base e.g. triethylamine, at low temperature, to give trifluoromethanesulfonamides of general formula (Ih). *Angewandte Chemie, International Edition* (2007), 46(11), 1852-1855.

i— a pyrrolidine-2,5-dione to give compounds of general formula (Ii):

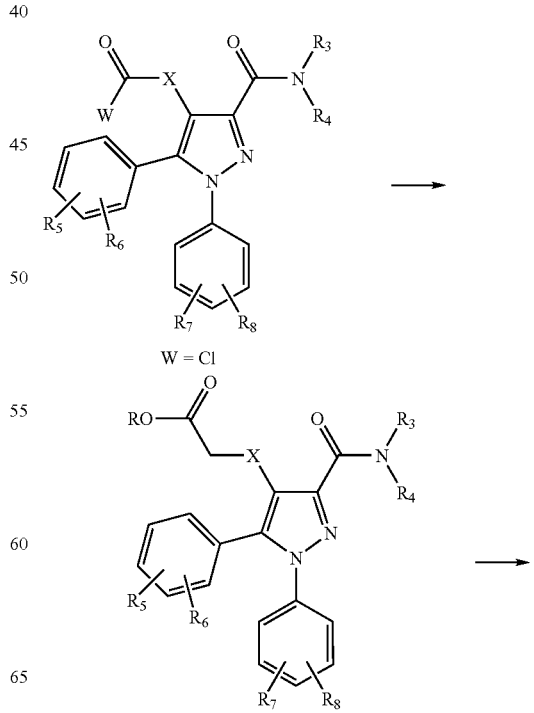

W = Cl

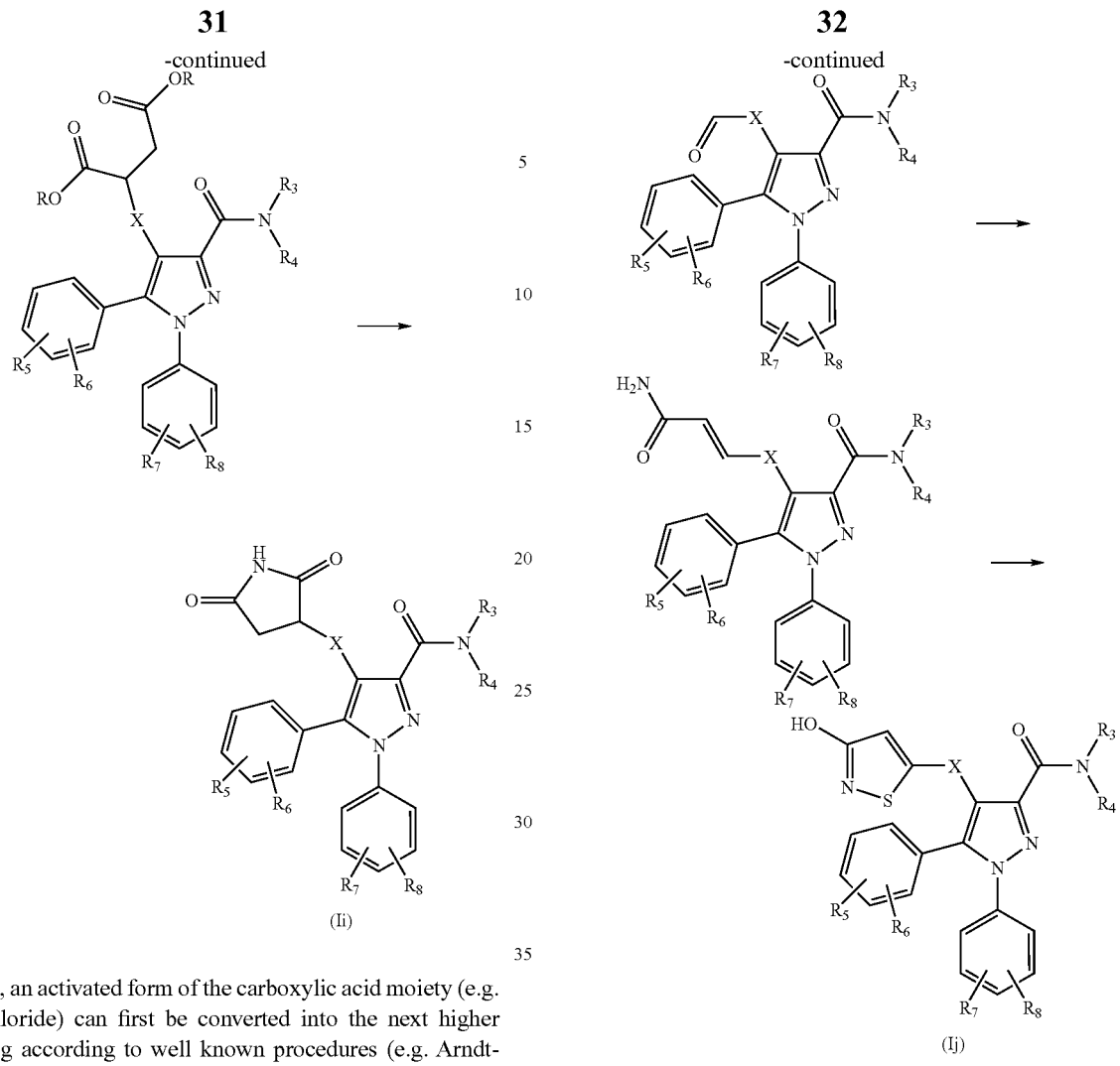

Thus, an activated form of the carboxylic acid moiety (e.g. acid chloride) can first be converted into the next higher homolog according to well known procedures (e.g. Arndt-Eistert synthesis). The homologous ester derivative can then be treated with a strong base e.g. LDA in tetrahydrofuran at low temperature and reacted with an alkylating agent e.g. ethylbromoacetate to give a diester intermediate which, upon hydrolysis in basic conditions, can be converted to pyrrolidine-2,5-diones of general formula (II) by treatment with urea or ammonia in water. See *Heterocycles* (1999), 50(2), 833-841; *Journal of the Chemical Society, Perkin Transactions 1: Organic and Bio-Organic Chemistry* (1972-1999) (1987), (8), 1679-87 j— a isothiazol-3-ol to give compounds of general formula (Ij):

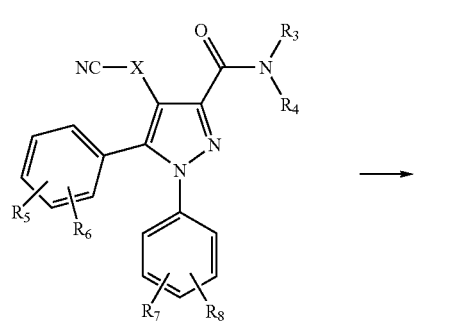

The nitrile group may first be reduced to an aldehyde by treatment of first a reducing agent such as diisobutyl aluminum hydride, thereafter follows an olefination with a phosphonate ester in the presence of a base (e.g. triethylphosphonoacetamide and sodiumhydride in 1,2-dimethoxy ethane) to form the allylic amide intermediate. A 1-4 Michael addition is then performed with thioacetic acid, followed by hydrolysis to the corresponding thiol (using sodium hydroxide) and subsequent oxidation to the disulfide (using oxidation agents such as hydrogen peroxide). Cyclization is then performed with e.g. sulfuryl chloride in dichloroethane to give isothiazol-3-ols of general formula (Ij). See *Journal of Medicinal Chemistry*, 2006, 49(4), 1389-1393.

k— a furazan-3-ol to give compounds of general formula (Ik):

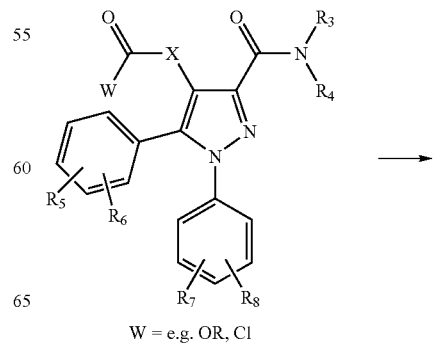

W = e.g. OR, Cl

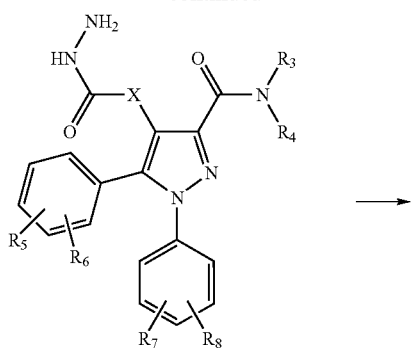

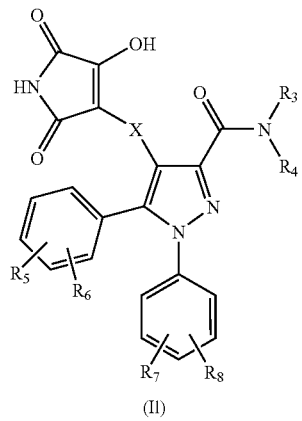

(II)

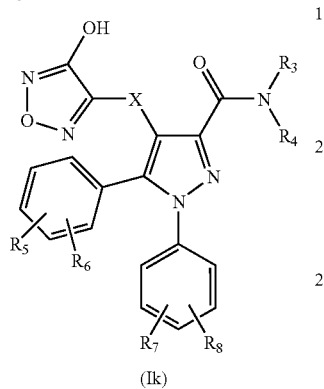

(Ik)

Thus, the ester group or activated acid may first be converted to an acid hydrazide by treatment with hydrazine under heating conditions. The intermediate is then reacted further to give furazan-3-ols of formula (Ik) by treatment with an appropriate activating agent e.g. nitrous acid and acetic anhydride or diazomethane in solvents like ethanol and chloroform. See *Journal of Heterocyclic Chemistry,* 16(4), 689-698, 1979.

l— a 3-Hydroxy-pyrrole-2,5-dione to give compounds of general formula (Il):

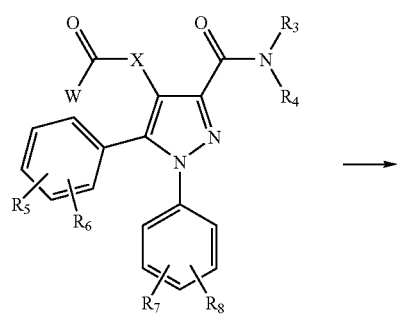

W = Cl

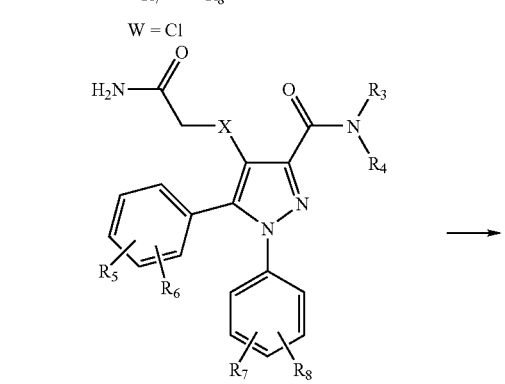

Thus, an activated form of the carboxylic acid moiety (e.g. acid chloride) can first be converted into the next higher amide homolog according to well known procedures (e.g. Arndt-Eistert synthesis). The homologous amide derivative can then be treated with a strong base e.g. potassium tert-butoxide in tetrahydrofuran at low temperature and reacted with dimethyl oxalate to give 3-Hydroxy-pyrrole-2,5-diones of general formula (Il) by treatment with urea or ammonia in water. See *Bioorganic & Medicinal Chemistry* (2006), 14(17), 5781-5794.

m— a N-acyl alkylsulfinamide to give compounds of general formula (Im):

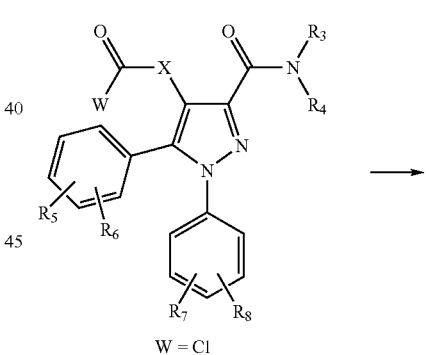

W = Cl

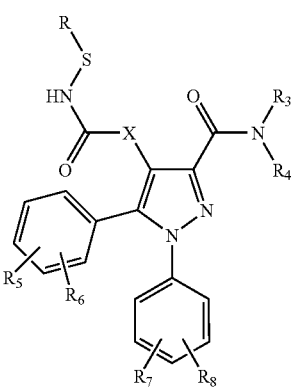

35
-continued

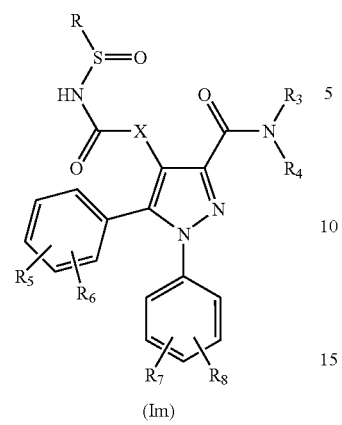

(Im)

Thus, an activated form of the carboxylic acid moiety (e.g. acid chloride) can first be reacted with an alkylsulfenamide (R—S—NH$_2$) in e.g. dichloromethane in presence of a base e.g. triethylamine to give a N-acyl alkylsulfenamide intermediate. This intermediate can then be converted to N-acyl alkylsulfinamides of general formula (Im) by treatment with an oxidative agent e.g. MCPBA in dichloromethane or NaIO$_4$ in water/methanol mixture or H$_2$O$_2$ in water/acetic acid mixture. See *Journal of Organic Chemistry*, 71(4), 1380-1389; 2006; *Tetrahedron*, 60(52), 12147-12152; 2004; *Bioorganic & Medicinal Chemistry*, 14(11), 3775-3784; 2006; *Monatshefte fuer Chemie*, 121(6-7), 539-47; 1990.

Such a procedure may include for instance the conversion of bromine to:

n— an isoxazol-3-ol to give compounds of general formula (In):

36
-continued

R = alkyl (In)

The bromo derivative can be synthesized by treatment with N-bromosuccinimide and 1,1'-azobis(isobutyronitrile) in carbon tetrachloride as described in US 2004/0192667. Thus, the bromine atom can be displaced by a keto ester in a presence of a base e.g. sodium ethoxide in e.g. ethanol to give an intermediate which can cyclise upon reaction with hydroxylamine hydrochloride in e.g. water/ethanol mixture in the presence of a base e.g sodium hydroxide to give isoxazol-3-ols of general formula (In). See *Journal of Medicinal Chemistry*, 45(12), 2454-2468; 2002.

o— a N-alkylsulfonamide (R=alkyl) or N-acylsulfonamide (R=—C(=O)-alkyl) to give compounds of general formula (Io):

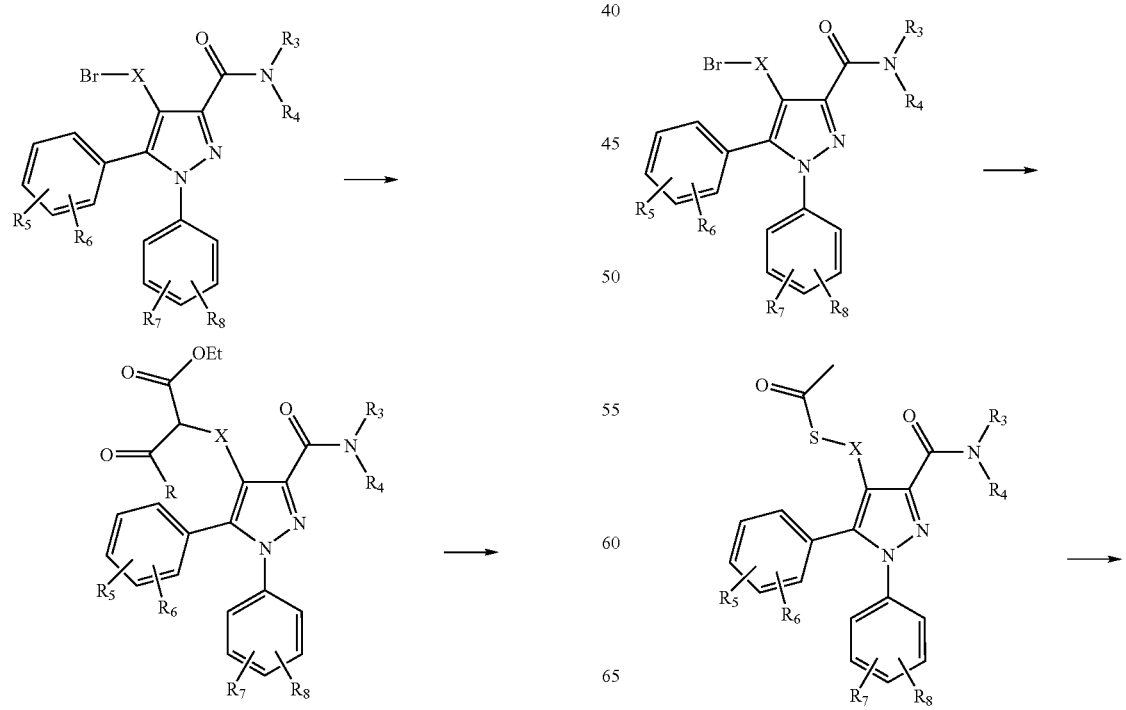

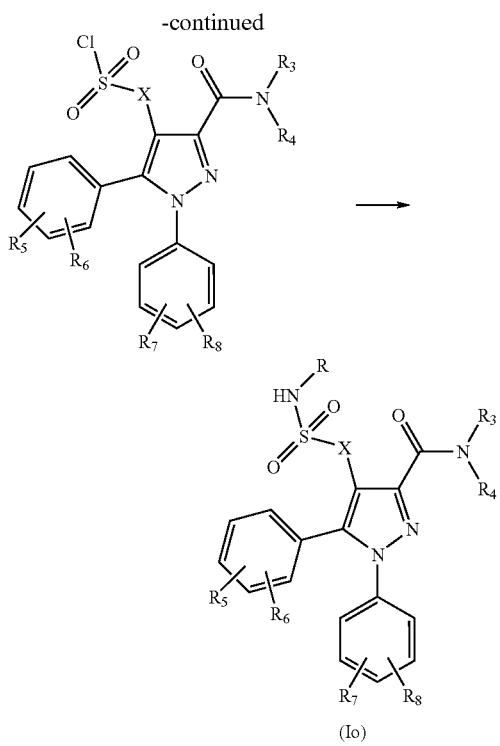

R = alkyl, —C(=O)-alkyl

The bromo derivative can be synthesized by treatment with N-bromosuccinimide and 1,1'-azobis(isobutyronitrile) in carbon tetrachloride as described in US 2004/0192667. Thus, the bromine atom can be displaced by potassium thioacetate in e.g. tetrahydrofuran and then treated with chlorine in e.g. ethanol/dichloromethane mixture to give a sulfonyl chloride intermediate, which, upon reaction with an alkylamine or alkylamide gives N-alkylsulfonamides or N-acyl sulfonamides of general formula (Io). See *Bioorganic & Medicinal Chemistry Letters*, 17(1), 73-77; 2007; *Bioorganic & Medicinal Chemistry Letters*, 17(7), 1991-1995; 2007.

The following examples of compounds of the invention, their preparation and properties are presented by way of illustration only:

General Comments

Microwave reactions were performed in a Personal Chemistry Emrys Optimizer. NMR spectra were obtained on a Bruker Avance AMX 300 MHz instrument. LC/MS was performed on an Agilent 1100-series instrument. UPLC/MS was performed on a Waters Acquity-series instrument. LC/MS (A-E) and HPLC/MS (F) methods are as follows:

(A) tfa20p5: Column: Gemini C18, 5 μm, 2.0×50 mm. Flow: 1.2 ml/min. Gradient: $0-3^{1/2}$ min: 10-95% acetonitrile in water, $3^{1/2}-4^{1/2}$ min: 95% acetonitrile. Modifier: 0.1% TFA. MS-ionisation mode: API-ES (pos.)

(B) tfa20n5: Column: Gemini C18, 5 μm, 2.0×50 mm. Flow: 1.2 ml/min. Gradient: $0-3^{1/2}$ min: 10-95% acetonitrile in water, $3^{1/2}-4^{1/2}$ min: 95% acetonitrile. Modifier: 0.1% TFA. MS-ionisation mode: API-ES (neg.)

(C) HCO$_3$20p5: Column: Gemini C18, 5 μm, 2.0×50 mm. Flow: 1.2 ml/min. Gradient: 0-4 min: 33-90% acetonitrile in water, $4-4^{1/2}$ min: 95% acetonitrile. Modifier: 5 mM NH$_4$HCO$_3$. MS-ionisation mode: API-ES (pos.)

(D) HCO$_3$20p5: Column: Gemini C18, 5 μm, 2.0×50 mm. Flow: 1.2 ml/min. Gradient: 0-4 min: 33-90% acetonitrile in water, $4-4^{1/2}$ min: 95% acetonitrile. Modifier: 5 mM NH$_4$HCO$_3$. MS-ionisation mode: API-ES (neg.)

(E) Preparative Method: Column: YMC 19×100 mm; Flow: 20 mL/min. Gradient: 0-8 min: 10-70% MeCN in water, 8-9 min: 70-95% MeCN in water, 9-12 min: 95% MeCN. Modifier: 0.1% TEA; MS-ionisation mode: API-ES (pos.)

(F) HCO$_2$H20t9850V: Column: ACQUITY HPLC BEH C18, 1.7 μm, 2.1×50 mm. Flow: 0.5 ml/min. Gradient: 0.1-1.0 min: 24-94% acetonitrile in water, 1-1.8 min: 94% acetonitrile. Modifier: 0.1% HCOOH. MS-ionisation mode: API-ES (pos. and neg. ionization)

Data is quoted for all compounds as molecular ion and retention time (RT) using method (A) unless otherwise stated.

Compounds of General Formula [1]

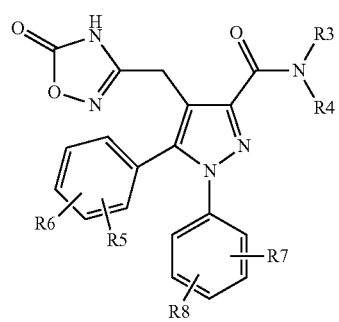

[1]

wherein $R_5$ and $R_8$ are hydrogen.

| Cpd No. | Compound Name | $R_3$—N—$R_4$ | $R_6$ | $R_7$ | Analysis HPLC RT MS (API-ES+) |
|---|---|---|---|---|---|
| 1.01 | 5-(4-Chloro-phenyl)-1-(2-chloro-phenyl)-4-(5-oxo-4,5-dihydro-[1,2,4]oxadiazol-3-ylmethyl)-1H-pyrazole-3-carboxylic acid [(R)-1-(4-trifluoromethyl-phenyl)-ethyl]-amide | ![NH-CH(CH3)-C6H4-CF3] | Para Cl | Ortho Cl | 3.34 min. 602.0 (M + H)+ |

Synthesis

Scheme 1

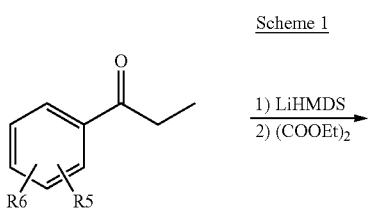

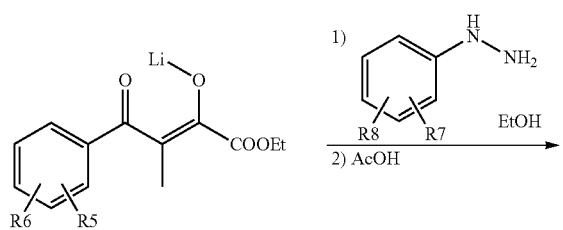

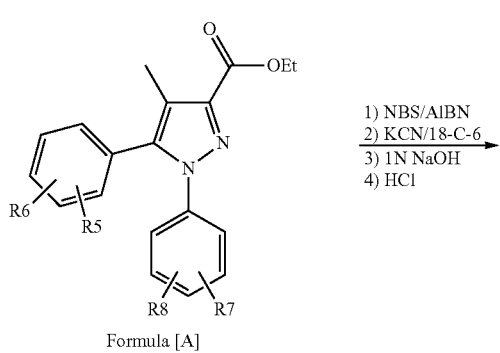

Formula [A]

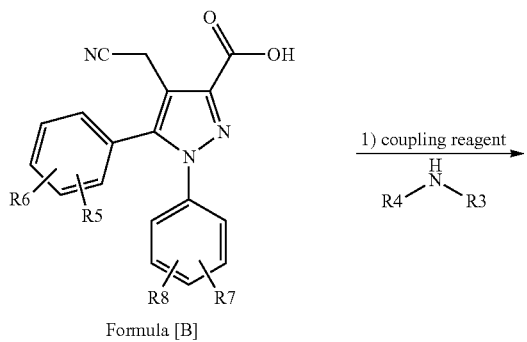

Formula [B]

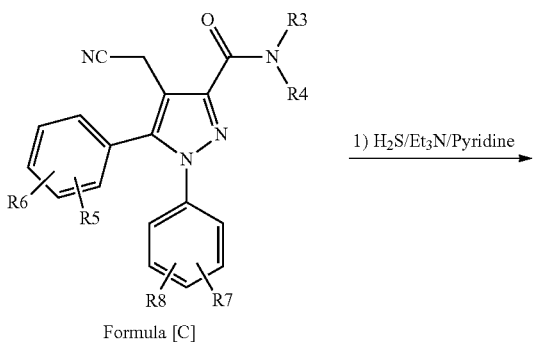

Formula [C]

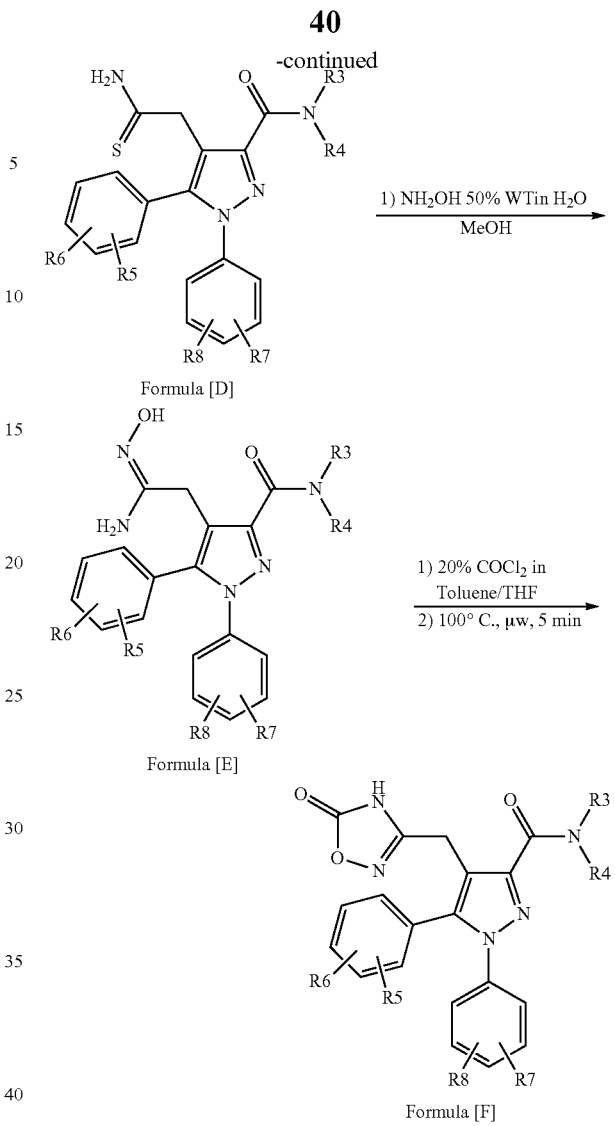

Compounds of formula [F] were prepared as described in scheme 1 above. Esters of formula [A] were obtained by well known methods (Ruoxi et al., J. Med. Chem, 1999, 42, 769-776). Esters of formula [A] were brominated by treatment with N-bromosuccinimide (1.1 eq.) and 1,1'-azobis(isobutyronitrile) (0.01 eq.) in carbon tetrachloride as described in US 2004/0192667. The resulting bromo compounds were not purified but treated directly with potassium cyanide (2 eq.) and 18-crown-6 ether (0.4 eq.) in acetonitrile at reflux for 15 hours. The reaction mixtures were partitioned between 1M sodium hydroxide solution and ethyl acetate. The organic phases were dried over sodium sulphate, filtered and evaporated. The residues were purified by chromatography over silica, eluting with ethyl acetate/cyclohexane mixtures to give ethyl ester derivatives of compounds of formula [B]. The esters were converted to their corresponding acids of formula [B] by treatment with sodium hydroxide under conditions familiar to those skilled in the art.

Alternatively, the bromo compounds could be treated with sodium cyanide in a mixture of ethanol and water at reflux, which gave directly the acids of formula [B].

Compounds of formula [B] were converted to compounds of formula [C] by well known methods using the appropriate amine $R_3NHR_4$ and coupling reagents. Nitriles of formula

[C] were treated with a saturated solution of hydrogen sulfide in triethylamine (2 eq.) and pyridine (solvent) to give, after stirring at room temperature, thioamides of formula [D]. Compounds of formula [D] were converted to amidoximes of formula [E] by reaction with hydroxylamine (50% WT in water; 2 eq.) in methanol.

Compounds of formula [F] were prepared by reacting compounds of formula [E] with 20% phosgene/toluene (leg.) in Tetrahydrofuran at 0° C. for 5 minutes, then at room temperature until a white precipitate was formed (~15 minutes) indicating the formation of the non cyclized intermediate. The heterogeneous mixture was then heated to 100° C. for 5 minutes in a microwave oven to give compounds of formula [F] after purification by preparative LCMS or silica gel chromatography.

Compound 1.01

Prepared according to the procedure outlined in scheme 2:

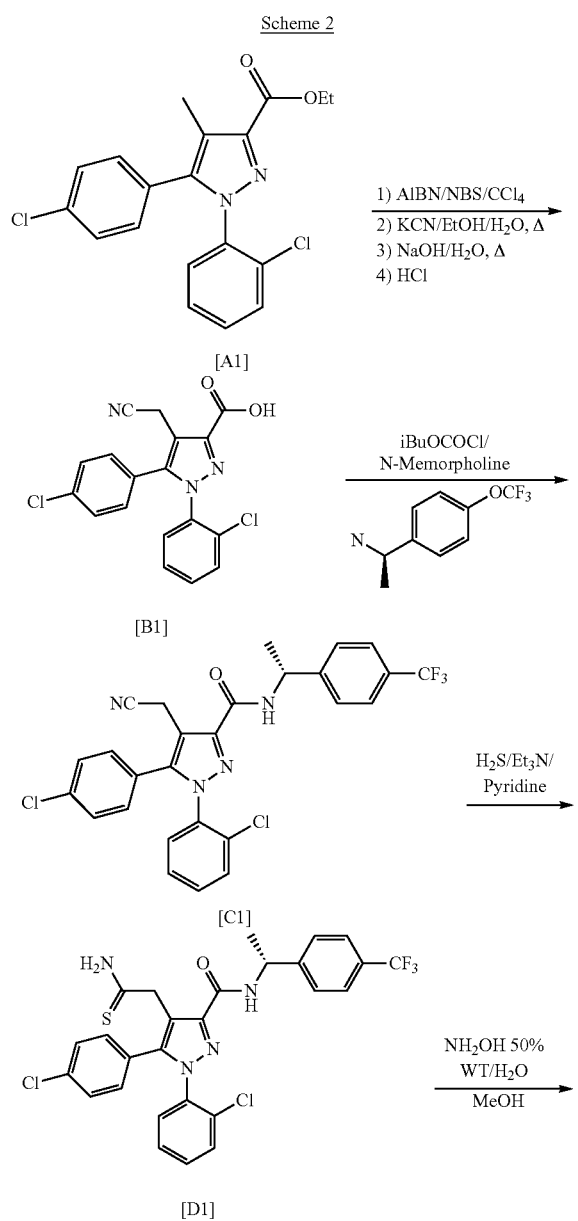

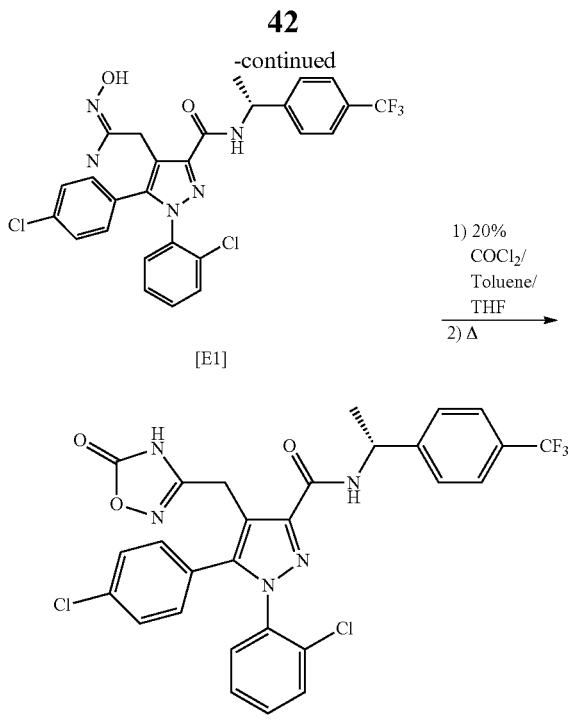

2,2'-Azobisisobutyronitrile (0.35 g, 2.13 mmol) was added to a stirred solution of [A1] (16 g, 42.6 mmol) and N-bromosuccinimide (8.35 g, 46.9 mmol) in tetrachloromethane (160 ml) and the mixture heated to reflux for 2 hours then cooled to room temperature. Saturated aqueous sodium metabisulphite solution (30 ml) was added and the mixture stirred for 24 hours then diluted with water (160 ml) plus brine (40 ml) and extracted with ethyl acetate (240 ml). The organic extracts were extracted with 1M sodium hydroxide solution (100 ml), dried over anhydrous magnesium sulphate and evaporated in vacuo.

The residue was dissolved in ethanol (100 ml) and a solution of potassium cyanide (8.33 g, 127.8 mmol) in water (25 ml) added. The mixture heated at reflux for 16 hours. 2M Sodium hydroxide solution (20 ml) was added and reflux continued for 30 minutes.

The mixture was diluted with water (300 ml), acidified with 2M hydrochloric acid and extracted with ethyl acetate (2×300 ml). Combined organic extracts were dried over magnesium sulphate and filtered through a silica pad, washing initially with ethyl acetate then 1% acetic acid in ethyl acetate. The filtrate was evaporated in vacuo then the residue co-evaporated with toluene to remove acetic acid and give 5-(4-Chloro-phenyl)-1-(2-chloro-phenyl)-4-cyanomethyl-1H-pyrazole-3-carboxylic acid [B1] (14.7 g, 93%) as a foam. $^1$H NMR (DMSO-D$_6$): δ 3.91 (2H, s), 7.10 (2H, d), 7.23-7.37 (6H, m). LCMS (method A): RT=2.476 min, (M+H)$^+$=372.

Isobutylchloroformate (1.15 ml; 8.87 mmol) was added to a stirred solution of [B1] (3 g; 8.06 mmol) and N-Methyl morpholine (0.97 ml; 8.87 mmol) in anhydrous THF (30 ml) at 0° C. under argon. The reaction mixture was allowed to reach room temperature and stirring was continued for 18 h upon which (R)-1-[4-(trifluoromethyl)phenyl]ethylamine (1.52 g; 8.06 mmol) was added dropwise. The reaction mixture was stirred until gas evolution had ceased (~5 min). LCMS indicated complete conversion of acid to form the expected product. The mixture was diluted with ethyl acetate (60 ml), washed with 1N aq. HCl solution then water then 1N aq. NaOH solution then brine, dried over MgSO$_4$ and concentrated in vacuo to give a pale yellow foam (4.5 g) which was purified by Combiflash (Silica: 40g; Loading: CH$_2$Cl$_2$ solution (20 ml); Elution: Hept./EtOAc gradient: 1/9 to 1/1 in 30 min; Flow: 38 ml); Fraction size: 100 ml) to give 5-(4-Chloro-phenyl)-1-(2-chloro-phenyl)-4-cyanomethyl-1H-pyrazole-3-carboxylic acid [(R)-1-(4-trifluoromethyl-phenyl)-ethyl]-amide [C1] as a white foam (1.6 g; 2.95 mmol; 37%). LCMS (method A): RT=3.42 min API-ES, Pos, 543.0 (M+H)$^+$ To a solution of [C1] (0.93 g; 1.71 mmol) in anhydrous pyridine (2 ml) was added triethylamine (0.48 ml; 3.42 mmol). Hydrogen sulphide (H$_2$S) was bubbled through the reaction mixture for ~5 min. The sealed microwave vial (20 ml) was placed under a positive pressure of H$_2$S (a 20 ml syringue was filled 3 times with H$_2$S then H$_2$S was "injected" (3×) in the vial through the spectum) and stirred for 1 day whereupon LCMS showed no SM [C1] left and formation of required product. The reaction mixture was quenched with 1N aq.HCl and extracted with CH$_2$Cl$_2$. The organic phase was washed with 1N aq. HCl, brine and dried through a "phase separation" column (biotage). Argon was bubbled through the organic solution to remove residual H2S. The organic phase was concentrated in vacuo to give 5-(4-Chloro-phenyl)-1-(2-chloro-phenyl)-4-thiocarbamoylmethyl-1H-pyrazole-3-carboxylic acid [(R)-1-(4-trifluoromethyl-phenyl)-ethyl]-amide [D1] as a white foam (0.84 g; 1.46 mmol; 85.4%). LCMS showed pure required compound. Used without further purification. LCMS (method A): RT=3.365 min API-ES, Pos, 577.0 (M+H)$^+$ To a solution of [D1] (60 mg; 0.1 mmol) in methanol (1 ml) was added hydroxylamine 50% WT in water (7.42 µl; 0.1 mmol). The reaction mixture was stirred for 18 hours at room temperature where upon LCMS showed mainly required product+small amounts of SM [D1]. A further equivalent of hydroxylamine 50% WT in water (7.42 µl; 0.1 mmol) was added and the reaction mixture was heated at 40° C. for 10 min. LCMS showed completion of the reaction. Solvent was removed in vacuo. The residue was partitioned between dichloromethane and water. The organic phase was dried through a "phase separation" column (Biotage) and concentrated in vacuo to give 5-(4-Chloro-phenyl)-1-(2-chloro-phenyl)-4-(N-hydroxycarbamimidoyl methyl)-1H-pyrazole-3-carboxylic acid [(R)-1-(4-trifluoromethyl-phenyl)-ethyl]-amide [E1] as a white foam (53 mg; 0.088 mmol; 88.5%). Used without any further purification. HPLC/MS (method F): RT=1.10 min; ES+=576.4 (M+H)$^+$ To a cooled (0° C.) solution of [E1] (53 mg; 0.088 mmol) in anhydrous tetrahydrofuran (1 ml) was added 20% WT phosgene in toluene (45.97 µl; 0.088 mmol). The reaction mixture was stirred for 5 min at 0° C. and 15 min at room temperature whereupon a white precipitate was formed. LCMS showed ~50% conversion of SM [E1] to an activated intermediate. The reaction mixture was then heated at 100° C. in a microwave for 5 min whereupon LCMS indicated full conversion of the intermediate to required product. The reaction mixture was cooled to room temperature and left for 2 days upon which a white precipitate was formed. The precipitate was filtered off and the filtrate concentrated in vacuo. LCMS of the precipitate showed mainly SM [E1]. The filtrate was purified by prepLCMS (method E) to give title compound [1.01] as a white solid (6 mg; 0.0095 mmol; 10.8%). $^1$H NMR (300 MHz., DMSO): 1.49 (d, 3H); 3.94 (q, 2H); 5.22 (quint., 1H); 7.25 (d, 2H); 7.42 (d, 2H); 7.48-7.72 (m, 8H); 8.95 (d, 1H); 12.12 (s, 1H). LCMS (method A): RT=3.34 min API-ES, Pos, 602.0 (M+H)$^+$. UPLC/MS (method F): RT=1.41 min; ES+=602.0 (M+H)$^+$ Compounds of General Formula [2]

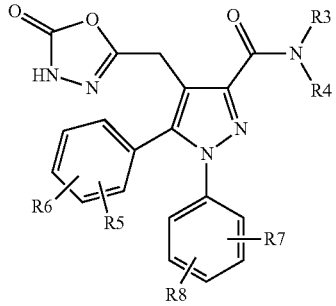

[2]

Wherein R$_5$ and R$_8$ are hydrogen.

| Cpd No. | Compound Name | R$_3$—N—R$_4$ | R$_6$ | R$_7$ | Analysis HPLC RT MS (API-ES+) |
|---|---|---|---|---|---|
| 2.01 | 5-{5-(4-Chloro-phenyl)-1-(2-chloro-phenyl)-3-[4-(2-fluoro-phenyl)-piperidine-1-carbonyl]-1H-pyrazol-4-ylmethyl}-3H-[1,3,4]oxadiazol-2-one | 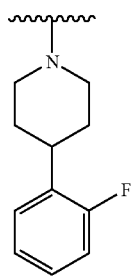 | Para Cl | Ortho Cl | 3.1 min. 592.0 (M + H)$^+$ |

| Cpd No. | Compound Name | R₃—N—R₄ | R₆ | R₇ | Analysis HPLC RT MS (API-ES+) |
|---|---|---|---|---|---|
| 2.02 | 1-(2-Chloro-phenyl)-5-(4-chloro-phenyl)-4-(5-oxo-4,5-dihydro-[1,3,4]oxadiazol-2-ylmethyl)-1H-pyrazole-3-carboxylic acid ((R)-1-p-tolyl-ethyl)-amide | HN with (R)-CH(CH₃)-C₆H₄-CF₃ | Para Cl | Ortho Cl | 1.36 min. Method F 602.0 (M + H)⁺ |

Synthesis

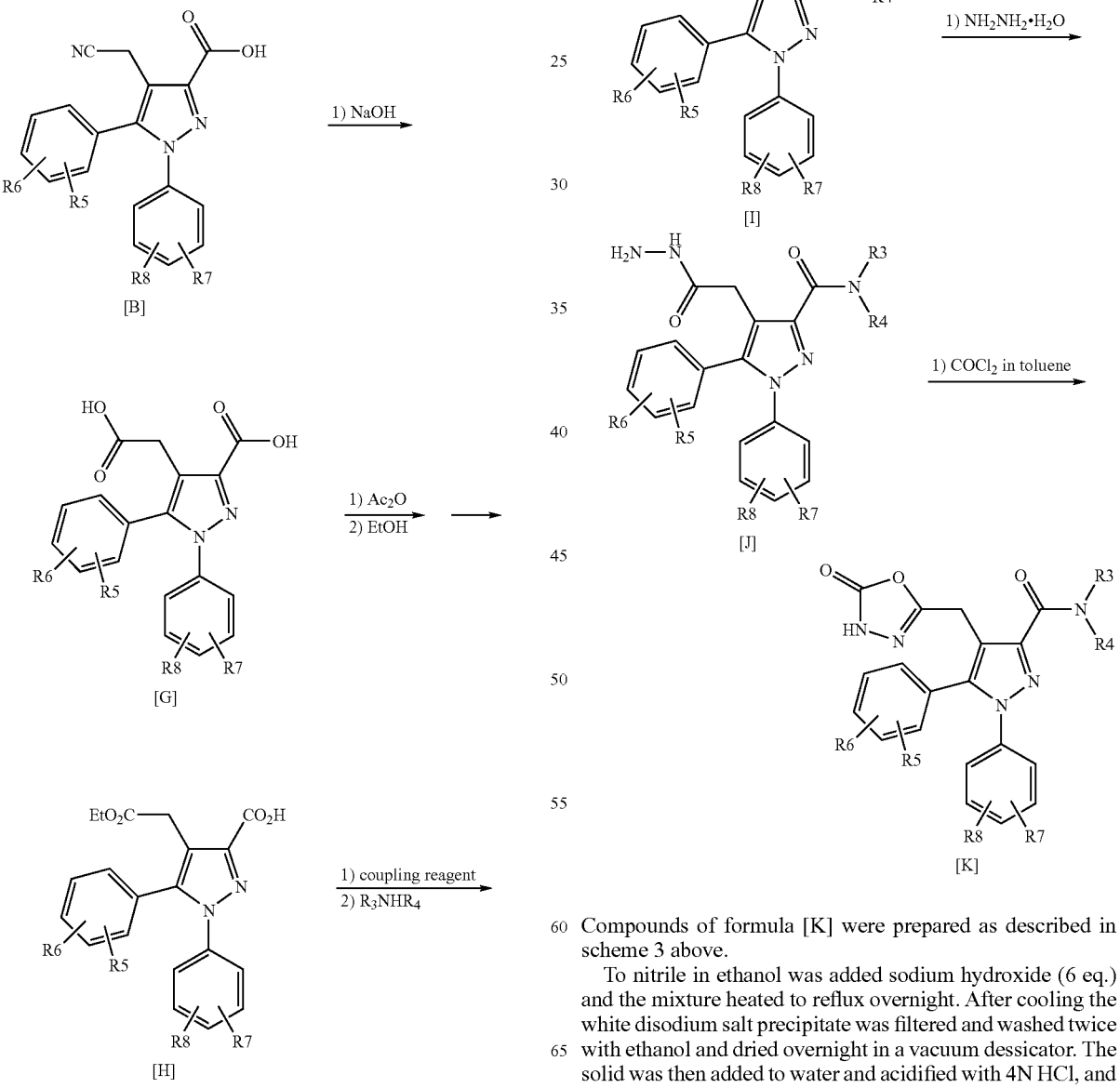

Compounds of formula [K] were prepared as described in scheme 3 above.

To nitrile in ethanol was added sodium hydroxide (6 eq.) and the mixture heated to reflux overnight. After cooling the white disodium salt precipitate was filtered and washed twice with ethanol and dried overnight in a vacuum dessicator. The solid was then added to water and acidified with 4N HCl, and the solid product was filtered off and dried for 72 h in a vacuum dessicator to give the diacid [G]. To this product in toluene was added pyridine (0.05 eq.) and acetic anhydride (1.1 eq.) and the reaction stirred overnight at room temperature. Further amounts of pyridine (0.025 eq.) and acetic anhydride (0.5 eq.) were added and the reaction stirred 2 h at room temperature followed by 45 min at 50° C. Ethanol was then added and the reaction stirred 48 h at room temperature, concentrated in vacuo and the residue was purified by recrystallisation from ethanol to give monoester [H]. Compounds of formula [H] were converted to compounds of formula [I] by well known methods using the appropriate amine $R_3NHR_4$ and coupling reagents. Compounds of formula [I] were treated with hydrazine monohydrate (2 eq.) in refluxing ethanol. The mixture was extracted (3×) with dichloromethane. The organic phases were combined, dried and concentrated in vacuo to give compounds of formula [J].

Compounds of formula [K] were synthesized by reacting compounds of formula [J] with 20% phosgene/toluene (1 eq.) in tetrahydrofuran, at 0° C. for 15 minutes, then at room temperature for 1 hour. Solvent was removed in vacuo and the residue was extracted with dichloromethane (2×). The organic phases were combined, dried and concentrated in vacuo to give formula [K] after purification by preparative LCMS or silica gel chromatography.

Compound 2.01

Prepared according to the procedure outlined in scheme 4:

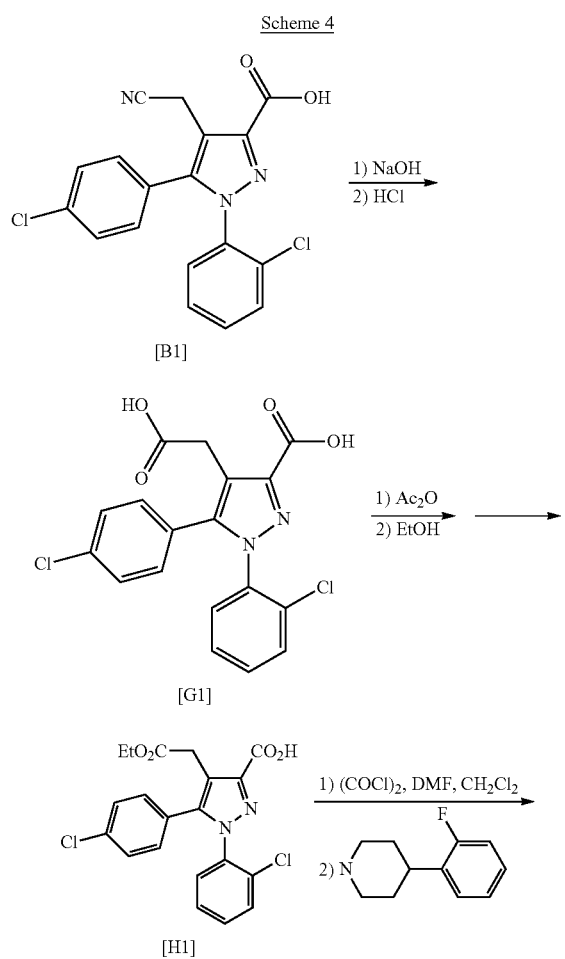

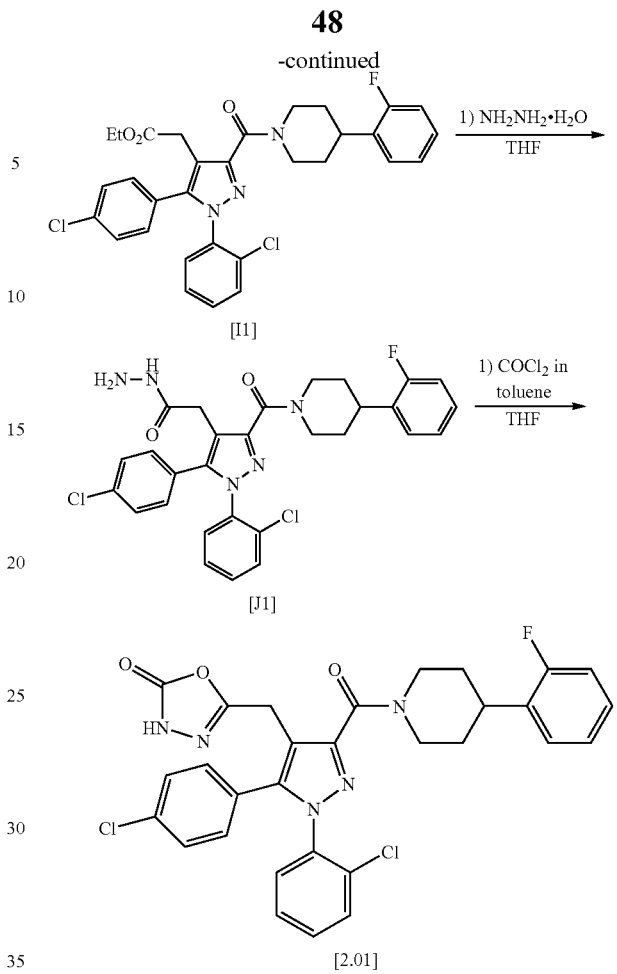

Compound of formula [B1] was prepared as described in scheme 2 above.

To 1-(2-Chloro-phenyl)-5-(4-chloro-phenyl)-4-cyanomethyl-1H-pyrazole-3-carboxylic acid [B1] (30 g, 0.8 mol) were added sodium hydroxide (19 g, 4.8 mol), ethanol (250 ml) and water (150 ml). The reaction mixture was heated to reflux over night. The heating was removed and the reaction mixture was allowed to reach room temperature. The formed precipitate was collected and washed with ethanol and dried in an exicator over night. The sodium salt was dissolved in water (400 ml) and HCl (4N) was added during extensively stirring, to avoid forming a gum, and the precipitate is collected and dried in a vacuum oven, yielding 27 g (0.7 mol, 86%) of 4-Carboxymethyl-1-(2-chloro-phenyl)-5-(4-chloro-phenyl)-1H-pyrazole-3-carboxylic acid [G1]. LCMS (method A): RT=2.1 min; ES+=390.9 (M+H)$^+$.

[G1] (19 g, 49 mmol) was dissolved in toluene (80 ml) under N$_2$-atm. and during stirring was pyridine (0.39 mL, 4.9 mmol) added and thereafter acetic anhydride (5.05 ml, 53 mmol) drop wise. The reaction was left stirring over night at room temperature. The reaction was not complete according to LCMS so the reaction was heated to 35° C. for 3 h. Since reaction was still not complete, the heating was removed and an additional portion of acetic anhydride (0.5 eq) and pyridine (0.05 eq). The reaction mixture was left stirring over night. Ethanol (100 ml) was added and the reaction was stirred at room temperature for three days. The solvent was removed in vacuo and the residue was recrystallized from ethanol (75 ml) and hot water (35 ml) yielding approximately 20 g. Since these crystals were not pure the product was recrystallized twice more yielding 11.37 g (56%) of 1-(2-Chloro-phenyl)-5-(4-chloro-phenyl)-4-ethoxycarbonylmethyl-1H-pyrazole-3-carboxylic acid [H1]. UPLC/MS (method F): RT=1.10 min; ES+=576.4 (M+H)+. $^1$H NMR (300 MHz., CDCl$_3$): 1.27 (t, 3H); 3.80 (s, 2H); 4.19 (q, 2H); 7.16 (d, 2H), 7.27-7.47 (m, 8H).

The ester [H1] (12 g, 29 mmol) was dissolved in dichloromethane (120 ml) and cooled to 0° C. To this suspension were oxalyl chloride (5 ml, 57 mmol) and dimethylformamide (0.05 ml) added and the cooling bath was removed. The suspension became more and more soluble and after 3 h a solid became visible again. Since some starting material was visible on LCMS was some more oxalyl chloride (0.5 ml, 0.2 eq.) added. This addition made the reaction complete and the solvent was removed in vacuo. In a flask containing some molecular sieves were 4-(2-fluorophenyl)piperidine hydrochloride (7.4 g, 34 mmol), DIPEA (6 ml), and dichloromethane (60 ml) added. This mixture was cooled to 0° C. whereupon the acid chloride dissolved in dichloromethane (60 ml) was added from a dropping funnel. The reaction mixture was stirred over night. The molecular sieves were filtered off and the reaction mixture was extracted with dichloromethane (3×). The combined organic phases were extracted with NaHCO$_3$ (sat.), washed with brine, dried over Na$_2$SO$_4$, filtered and evaporated yielded 15 g of the crude ester. The crude product was purified on a short silica colon (EtOAc/Heptane, 1:4 followed by 1:1) the fractions containing product was pooled and recrystallized with EtOAc (45 ml) and Heptane (80 ml) yielding 9.1 g of {1-(2-Chlorophenyl)-5-(4-chloro-phenyl)-3-[4-(2-fluoro-phenyl)-piperidine-1-carbonyl]-1H-pyrazol-4-yl}-acetic acid ethyl ester [I1]. The mother liquid was concentrated in vacuo and purified by recrystallization with EtOAC and Heptane yielding 1.7 g more of [I1]. LCMS (method A): RT=3.6 min. ES$^+$=580.1 (M+1)$^+$. $^1$H NMR (300 MHz., CDCl$_3$): 1.28 (t, 3H); 1.72-2.04 (m, 4H); 2.91 (t, 1H); 3.21 (tt, 1H); 3.31 (t, 1H); 3.72 (AB-q, 2H); 4.18 (q, 2H); 4.78 (d, 1H); 4.91 (d, 1H); 7.00-7.44 (m, 8H).

The compound [I1] (105 mg, 0.18 mmol) was dissolved in ethanol (1.2 ml) and hydrazine (10 µl, 0.18 mmol) was added. The flask was sealed and heated to reflux over night. LCMS only showed the starting material so a second equivalent of the hydrazine (10 µl, 0.18 mmol) was added and the reaction was refluxed over weekend. Water was added to the reaction followed by extraction with dichloromethane (2×). The combined organic phases were dried over Na$_2$SO$_4$, filtered and evaporated yielding 108 mg of crude product [J1] which was used without further purification. UPLC/MS (method F): RT=1.27 min. ES$^+$=566.4 (M+1)$^+$.

The crude [J1] was dissolved in THF (1 ml) and cooled to 0° C. Phosgene (20% in toluene, 20 µL) was added and the reaction was stirred 15 min at 0° C. and thereafter at r.t. for 1 h. Extracted the crude product with CH$_2$Cl$_2$/water, dried the combined organic phases with Na$_2$SO$_4$, filtered and evaporated giving the crude product. Some of the crude product (25 mg) was purified by prepLCMS (method E) to give title compound [2.01] as a white solid (5.88 mg; 0.0099 mmol; 5.5%). HPLC/MS (method F): RT=1.34 min; ES+=592.4 (M+H)$^+$. $^1$H NMR (300 MHz., DMSO-d$_6$): 1.52-1.92 (m, 4H); 2.88 (t, 1H); 3.08-3.34 (m, 2H) obscured by water signal); 3.89 (AB-q, 2H); 4.46 (d, 1H); 4.67 (d, 1H); 7.10-7.15 (m, 1H); 7.16 (d, 1H); 7.21-7.31 (m, 3H); 7.35 (t, 1H); 7.40-7.53 (m, 4H); 7.58 (dd, 1H); 7.66 (dd, 1H); 12.07 (br s, 1H).

Compound 2.02

Prepared according to the procedure outlined in scheme 4 identical to the one described for the preparation of compound 2.01:

Scheme 4a

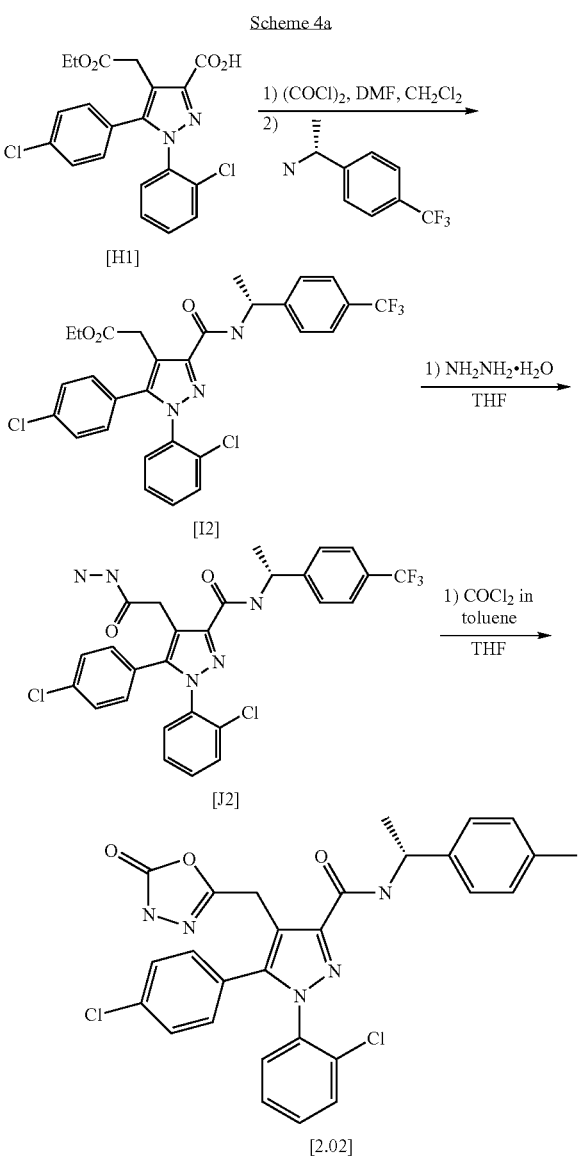

Compound of formula [I2] was prepared as described in scheme 4, using [H1] and (R)-1-(4-trifluoromethyl-phenyl)-ethylamine.

Compounds of General Formula [3]

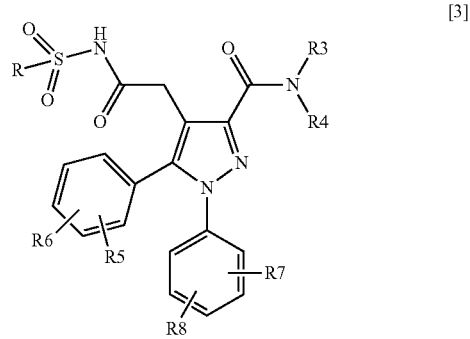

Wherein R$_5$ and R$_8$ are hydrogen.

| Cpd No. | Compound Name | R₃—N—R₄ | R | R₆ | R₇ | Analysis HPLC RT MS (API-ES+) |
|---|---|---|---|---|---|---|
| 3.01 | N-(2-{1-(2-Chloro-phenyl)-5-(4-chloro-phenyl)-3-[4-(2-fluoro-phenyl)-piperidine-1-carbonyl]-1H-pyrazol-4-yl}-acetyl)-methanesulfonamide | 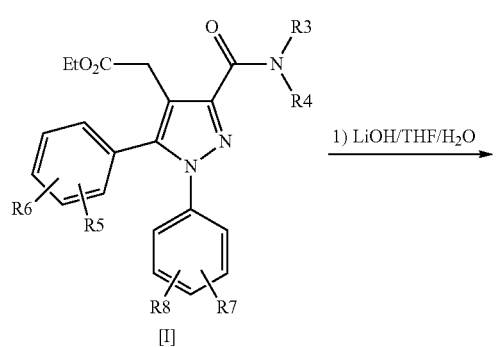 | CH₃— | Para Cl | Ortho Cl | 3.39 min. 629 (M + H)⁺ |
| 3.02 | 1-(2-Chloro-phenyl)-5-(4-chloro-phenyl)-4-(2-methanesulfonylamino-2-oxo-ethyl)-1H-pyrazole-3-carboxylic acid methyl-[(R)-1-(4-trifluoromethyl-phenyl)-ethyl]-amide | 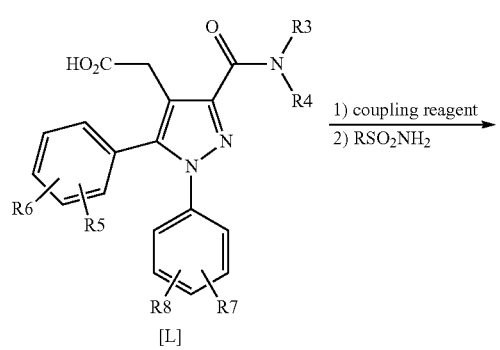 | CH₃— | Para Cl | Ortho Cl | 3.54 min. 653 (M + H)⁺ |

Synthesis

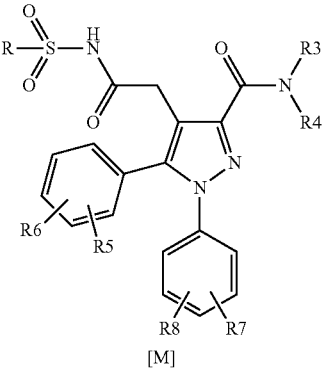

Compounds of formula [M] were prepared as described in scheme 5 above.

Compounds of formula [L] were isolated upon hydrolysis of compounds of formula [I] in basic medium according to well know procedures. Acids of formula [L] were converted to reactive intermediates upon treatment with e.g. 4-(dimethylamino)pyridine (1.7 eq.), 1-ethyl-3 (3-dimethylaminopropyl)carbodiimid hydrochloride (2 eq.) and diisopropylethylamine (3 eq.) and reacted with an appropriate alkyl sulphonamide (2 eq.) in dichloromethane to give compounds of formula [M] after purification on SAX column (Biotage).

Compound 3.01
Prepared according to the procedure outlined in scheme 6:

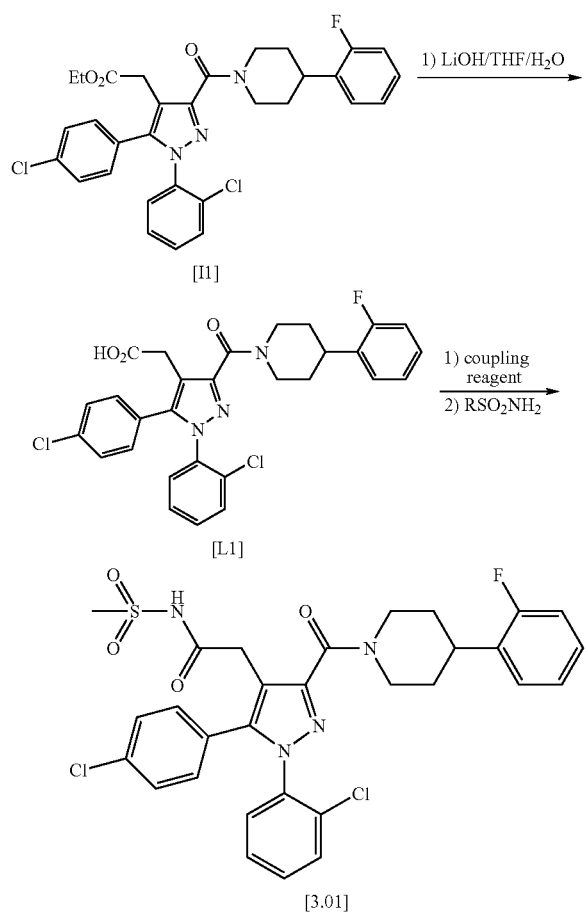

[I1]

[L1]

[3.01]

Compound of formula [I1] was prepared as described in scheme 4 above.

To the ester {1-(2-Chloro-phenyl)-5-(4-chloro-phenyl)-3-[4-(2-fluoro-phenyl)-piperidine-1-carbonyl]-1H-pyrazol-4-yl}-acetic acid ethyl ester [I1] (12.3 g, 21.2 mmol) described in example 2.01 were THF (100 ml), water (100 ml), and lithium hydroxide (9 g, 214 mmol) added. The reaction was stirred over night. The organic solvent was removed in vacuo and the remaining water phase was acidified with 2 M HCl and thereafter extracted with EtOAc (2×). The combined organic phases were washed with water and brine, dried over $Na_2SO_4$, filtered and evaporated yielding 11.5 g of crude product. Repeatedly recrystallisation from EtOAc and Heptane yielded 7.8 g of pure {1-(2-Chloro-phenyl)-5-(4-chloro-phenyl)-3-[4-(2-fluoro-phenyl)-piperidine-1-carbonyl]-1H-pyrazol-4-yl}-acetic acid [L1]. LCMS (method A): RT=3.5 min. $ES^+$=552.1 $(M+1)^+$. 300 MHz ($CDCl_3$): 1.80-2.12 (4H, m), 3.02 (1H, dt), 3.20-3.43 (2H, m), 3.60 (2H, q), 5.01 (1H, d), 5.20 (1H, d), 7.01-7.54 (12H, m), and 14.48 (1H, br s).

To a mixture of [L1] (100 mg; 0.18 mmol), 4-(dimethylamino)pyridine (37.6 mg; 0.31 mmol), 1-ethyl-3(3-dimethylaminopropyl)carbodiimid hydrochloride (69.4 mg; 0.36 mmol) and methanesulfonamide (34.44 mg; 0.36 mmol) in dichloromethane (0.5 ml) was added diisopropylethylamine (90 μl; 0.54 mmol). The reaction mixture was stirred overnight at room temperature whereupon LCMS showed full conversion of [L1] to required product.

The mixture was washed with 1N aq. HCl, the organic phase was dried and evaporated in vacuo to give 110 mg of crude material which was purified on a SAX column using dichloromethane as the eluent to give title compound [3.01] (54 mg; 0.085 mmol; 47.4%). LCMS (method A): RT=3.39 min API-ES, Pos, 629.0 $(M+H)^+$.

Compound 3.02
Prepared according to the procedure outlined in scheme 6a identical to the one described for the preparation of compound 3.01:

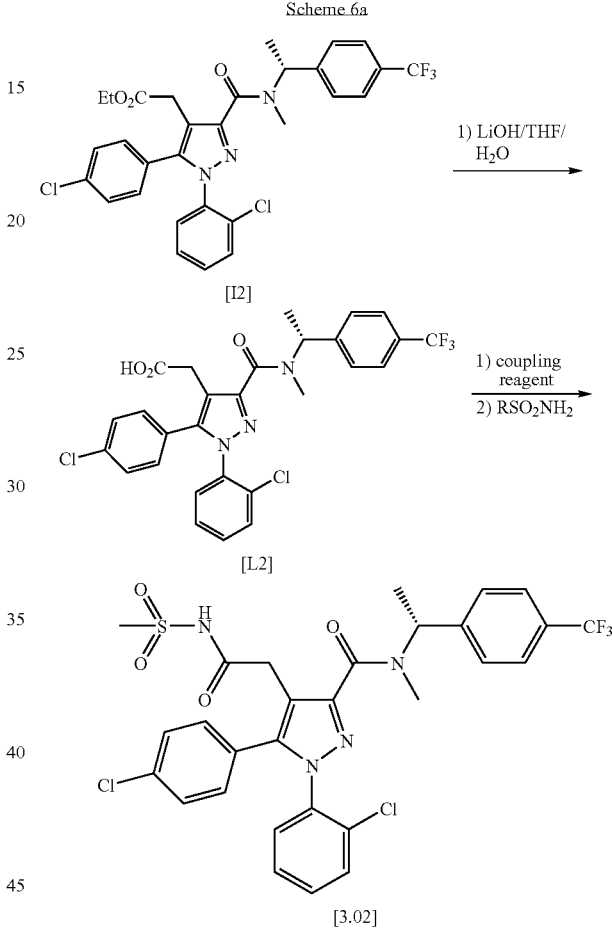

[I2]

[L2]

[3.02]

Compound of formula [I2] was prepared as described in scheme 4, using [H1] and Methyl-[(R)-1-(4-trifluoromethyl-phenyl)-ethyl]-amine Compounds of General Formula [4]

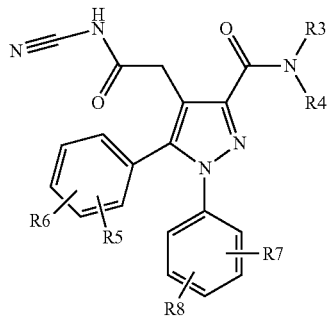

[4]

Wherein $R_5$ and $R_8$ are hydrogen.

| Cpd No. | Compound Name | R₃—N—R₄ | R₆ | R₇ | Analysis HPLC RT MS (API-ES+) |
|---|---|---|---|---|---|
| 4.01 | 2-{1-(2-Chloro-phenyl)-5-(4-chloro-phenyl)-3-[4-(2-fluoro-phenyl)-piperidine-1-carbonyl]-1H-pyrazol-4-yl}-N-cyano-acetamide | piperidine with 2-fluorophenyl | Para Cl | Ortho Cl | 3.4 min. 576.0 (M + H)⁺ |
| 4.02 | (1-(2-Chloro-phenyl)-5-(4-chloro-phenyl)-3-{methyl-[(R)-1-(4-trifluoromethyl-phenyl)-ethyl]-carbamoyl}-1H-pyrazol-4-yl)-N-cyano-acetamide | N-methyl-(R)-1-(4-CF₃-phenyl)ethyl | Para Cl | Ortho Cl | 3.42 min. 600 (M + H)⁺ |
| 4.03 | {1-(2-Chloro-phenyl)-5-(4-chloro-phenyl)-3-[4-(3,5-difluoro-phenoxy)-piperidine-1-carbonyl]-1H-pyrazol-4-yl}-N-cyano-acetamide | piperidine with 3,5-difluorophenoxy | Para Cl | Ortho Cl | 3.49 min. 610 (M + H)⁺ |

Synthesis

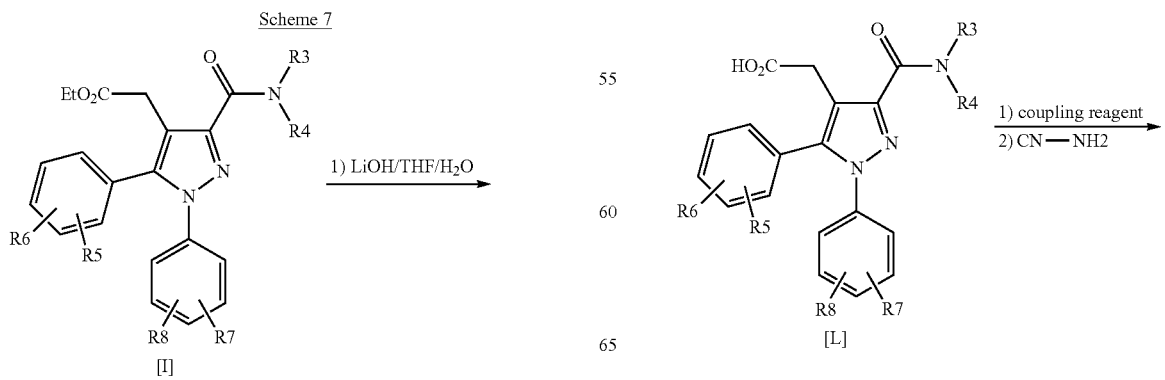

Scheme 7

[I] →(1) LiOH/THF/H₂O)→ [L] →(1) coupling reagent; 2) CN—NH2)→

-continued

-continued

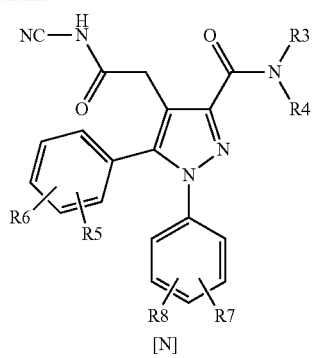

[N]

Compounds of formula [N] were prepared as described in scheme 7 above according to a procedure identical to the one described for the synthesis of compounds of formula [M], using cyanamide (CN—NH2) instead of an alkylsulfonamide.

Compound 4.01

Prepared according to the procedure outlined in scheme 8:

Scheme 8

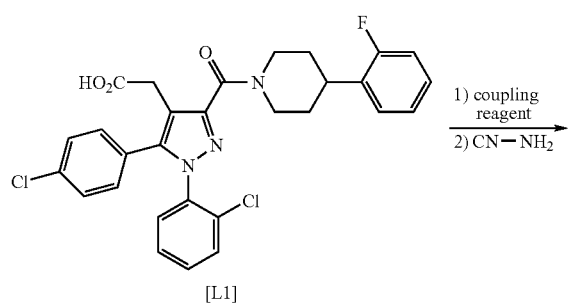

[L1]

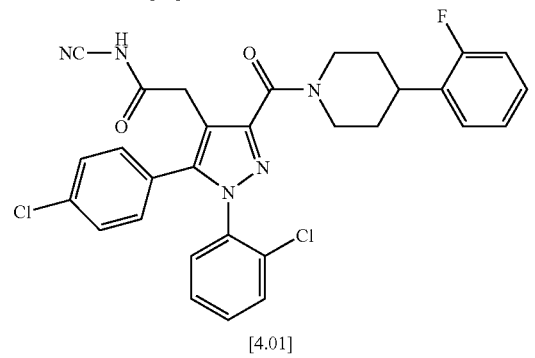

[4.01]

Compound of formula [L1] was prepared as described in scheme 6 above.

To a mixture of [L1] (100 mg; 0.18 mmol), 4-(dimethylamino)pyridine (26.54 mg; 0.22 mmol), 1-ethyl-3(3-dimethylaminopropyl)carbodiimid hydrochloride (48.58 mg; 0.25 mmol) and cyanamide (15.22 mg; 0.36 mmol) in dichloromethane (0.5 ml) was added diisopropylethylamine (60 µl; 0.36 mmol). The reaction mixture was stirred overnight at room temperature whereupon LCMS showed full conversion of [L1] to required product. The mixture was washed with 1N aq. HCl, the organic phase was dried and evaporated in vacuo to give 110 mg of crude material which was purified on a SAX column using dichloromethane as the eluent to give title compound [4.01] (43 mg; 0.114 mmol; 63.2%). LCMS (method A): RT=3.3 min API-ES, Pos, 576.0 (M+H)+.

Compound 4.02

Prepared according to the procedure outlined in scheme 8a identical to the one described for the preparation of compound 4.01:

Scheme 8a

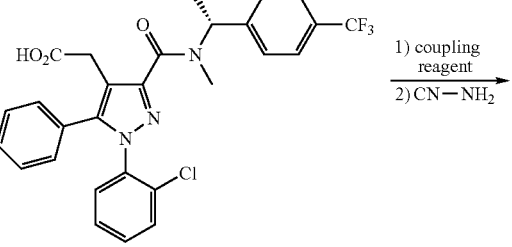

[L2]

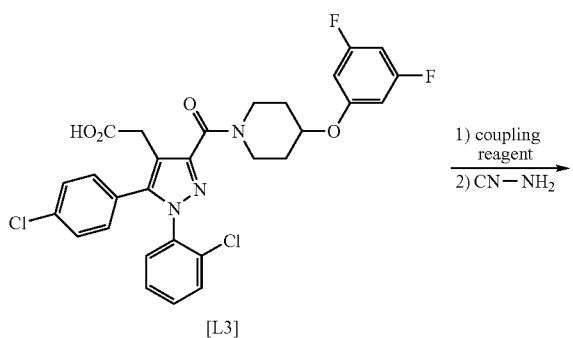

[4.02]

Compound of formula [L2] was prepared as described in scheme 6a.

Compound 4.03

Prepared according to the procedure outlined in scheme 8b identical to the one described for the preparation of compound 4.01:

Scheme 8b

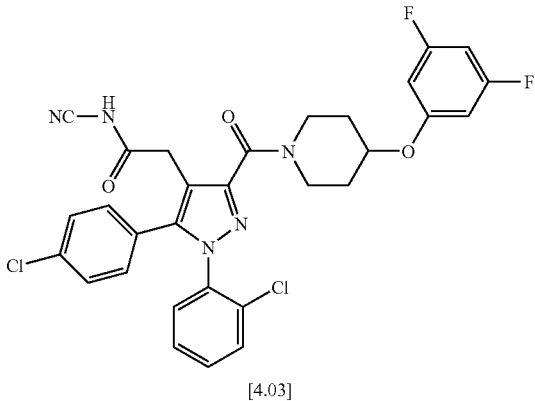

[L3]

[4.03]

Compound of formula [L3] was prepared from [I3] as described in scheme 7.

Compound of formula [I3] was prepared as described in scheme 4, using [H1] and 4-(3,5-Difluoro-phenoxy)-piperidine.

Compounds of General Formula [5]

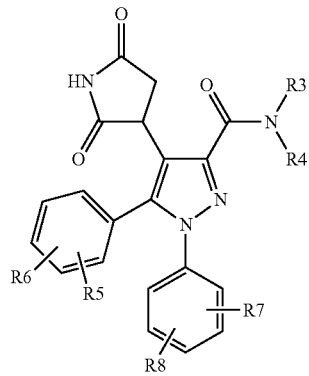

[5]

Wherein $R_5$ and $R_8$ are hydrogen.

| Cpd No. | Compound Name | $R_3$—N—$R_4$ | $R_6$ | $R_7$ | Analysis HPLC RT MS (API-ES+) Method (F) |
|---|---|---|---|---|---|
| 5.01 | 1-(2-Chloro-phenyl)-5-(4-chloro-phenyl)-4-(2,5-dioxo-pyrrolidin-3-yl)-1H-pyrazole-3-carboxylic acid methyl-[(R)-1-(4-trifluoromethyl-phenyl)-ethyl]-amide | 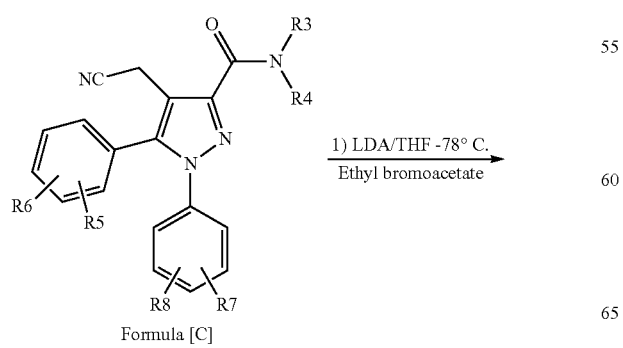 | Para Cl | Ortho Cl | 1.38 min. 615.0 (M + H)+ |

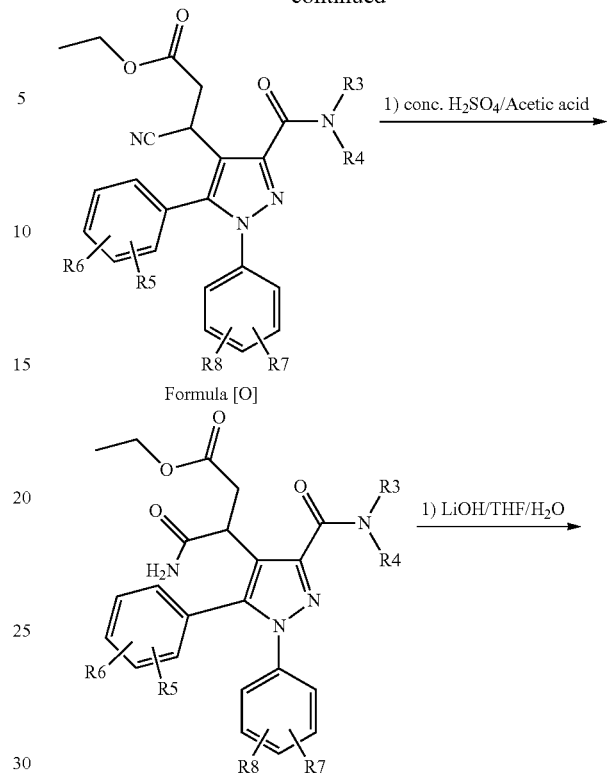

Formula [O]

Formula [P]

Synthesis

Scheme 9

Formula [C]

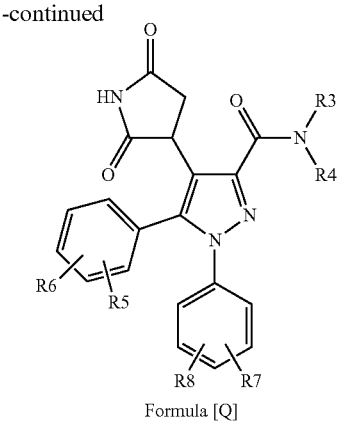

Formula [Q]

Compounds of formula [Q] were prepared as described in scheme 9 above.

Compounds of formula [C] were prepared as described in scheme 1. Compounds of formula [O] were synthesized by treatment of [C] with one eq. of LDA, followed by alkylation with 1.5 eq. of ethyl bromoacetate, in anhydrous THF, at −78° C.

The alkylated compounds of formula [O] were converted to the amides of formula [P] by a short (10 min.) reaction with a hot (80° C.) conc.$H_2SO_4$/Acetic acid mixture.

Reaction of amides of formula [P] with LiOH in THF/water mixture, at room temperature, led to full conversion to the cyclic compounds of formula [Q].

Compound 5.01

Prepared according to the procedure outlined in scheme 10:

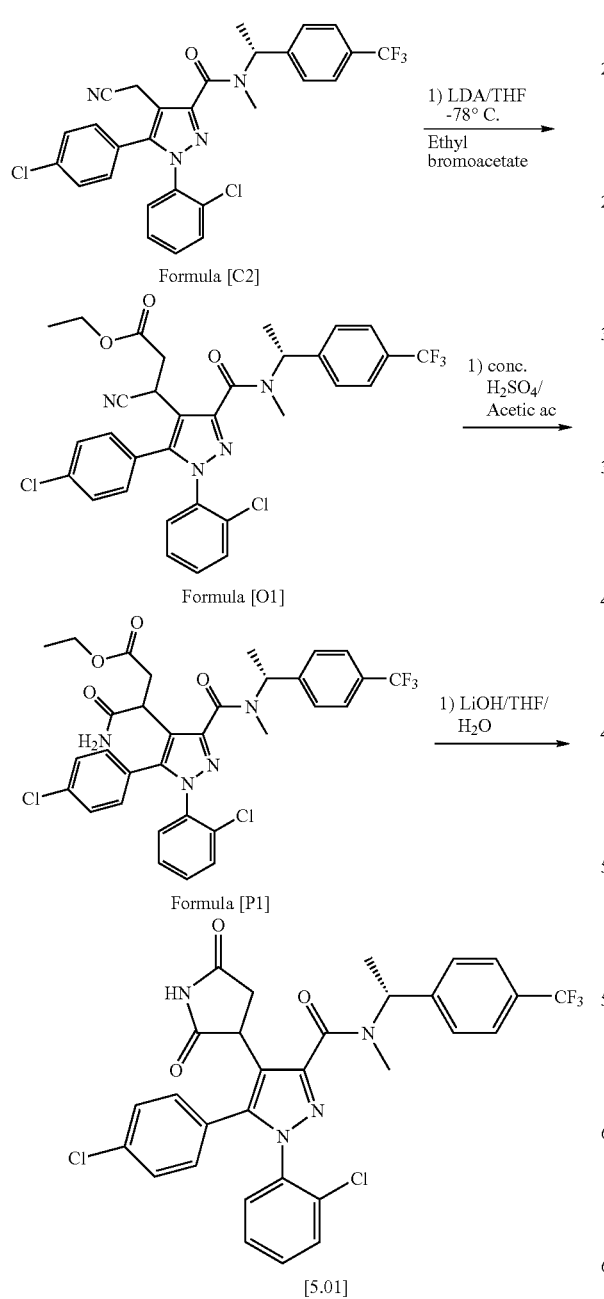

Compound of formula [C2] was prepared as described in scheme 1 using [B1] and Methyl-[(R)-1-(4-trifluoromethyl-phenyl)-ethyl]-amine.

LDA was prepared by addition of 2.5M Buthyl lithium in hexanes (230 ul, 0.57 mmol) to a cooled (−20° C.) solution of diisopropylamine (97 ul, 0.69 mmol) in dry THF (3 ml), under an argon atmosphere. After stirring for 20 minutes, this mixture was added to a cooled (−78° C.) solution of [C2] (320 mg, 0.57 mmol) in dry THF (2 ml), under an argon atmosphere. The reaction mixture was stirred for 30 minutes at −78° C. Ethyl bromoacetate (95.5 ul, 0.86 mmol) was added and the reaction mixture was stirred at −78° C. for 1 hour. The reaction mixture was then allowed to slowly warm-up to 5° C. over 14 hours and worked-up. Sat.aq. $NH_4Cl$ was added and the reaction mixture was extracted with diethyl ether. The organic phase was dried over $MgSO_4$ and concentrated in vacuo to give a brown oil (350 mg). The crude compound of formula [O1] was purified by silica gel chromatography (Silica: 12 g; Loading: $CH_2Cl_2$ solution (5 ml); Elution: Hept./EtOAc isocratic: 1/1); Fraction size: 10 ml) to give a pale-yellow oil (239 mg). TLC showed only one UV active spot but UPLC/MS (method F) 2 peaks at Rt=1.47 and 1.51 min (~40/60) respectively corresponding to a non identified impurity and [O1]. The contaminated compound of formula [O1] was used without further purification.

A solution of [O1] (239 mg, 0.37 mmol) in acetic acid (0.5 ml) was heated to 60° C. Concentrated sulfuric acid (0.3 ml) was added and the reaction mixture was heated to 80° C. for 10 minutes. After cooling, the reaction mixture was worked-up. The reaction mixture was poured onto ice and extracted with dichloromethane. The organic phase was dried over $MgSO_4$ and concentrated in vacuo to give a pale-yellow oil (100 mg). The crude compound of formula [P1] was purified by silica gel chromatography (Silica: 4 g; Loading: $CH_2Cl_2$ solution (2 ml); Elution: Hept./EtOAc isocratic: 1/1, then 4/1); Fraction size: 3 ml) to give compound of formula [P1] (37 mg, 15%). [P1] was contaminated with non identified impurities and was used without further purification.

To a slurry of [P1] (37 mg, 0.06 mmol) in a THF/H2O (1 ml, 1/1) mixture was added lithium hydroxide monohydrate (9.39 mg, 0.22 mmol). The reaction mixture was stirred for 1 hour at room temperature whereupon LCMS showed full conversion to succinimide [5.01]. The reaction mixture was concentrated in vacuo to remove THF. The aqueous phase was acidified with 1N aq. HCl to pH=1-2 and extracted with dichloromethane. The organic phase was dried through a phase separation column (Biotage) and concentrated in vacuo to give crude [5.01] which was purified by preparative LCMS (method E) to give purified [5.01] as a white solid (23 mg, 67%).

Compounds of General Formula [6]

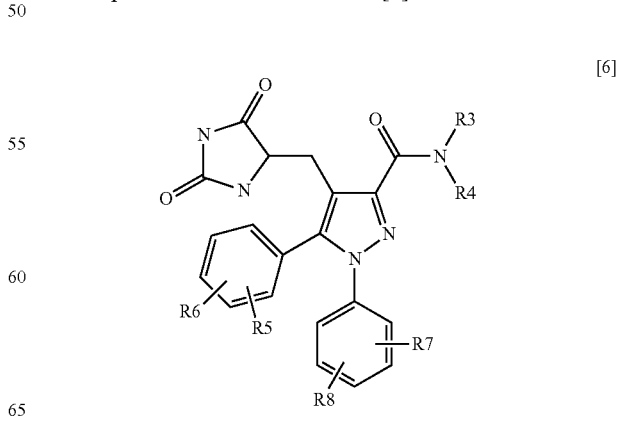

Wherein $R_5$ and $R_8$ are hydrogen.

| Cpd No. | Compound Name | R₃—N—R₄ | R₆ | R₇ | Analysis HPLC RT MS (API-ES+) Method F |
|---|---|---|---|---|---|
| 6.01 | 5-{1-(2-Chloro-phenyl)-5-(4-chloro-phenyl)-3-[4-(2-fluoro-phenyl)-piperidine-1-carbonyl]-1H-pyrazol-4-ylmethyl}-imidazolidine-2,4-dione |  | Para Cl | Ortho Cl | 1.26 min. 606.0 (M + H)⁺ |
| 6.02 | 1-(2-Chloro-phenyl)-5-(4-chloro-phenyl)-4-(2,5-dioxo-imidazolidin-4-ylmethyl)-1H-pyrazole-3-carboxylic acid ((R)-1-p-tolyl-ethyl)-amide | 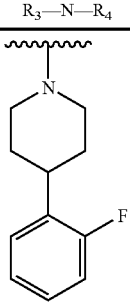 | Para Cl | Ortho Cl | 1.29 min. 616.0 (M + H)⁺ |

Synthesis

Scheme 11

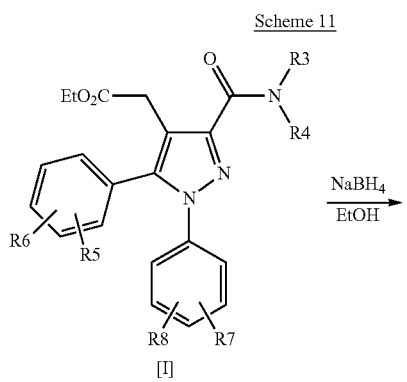

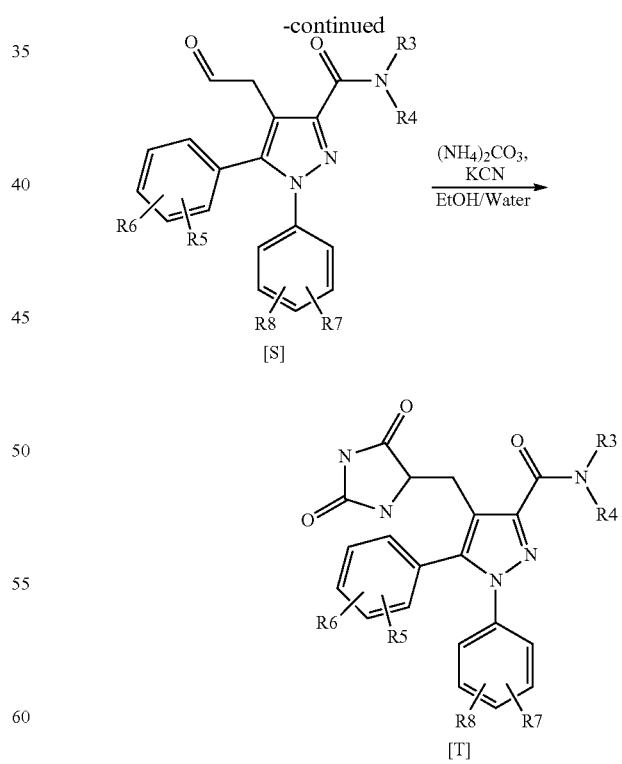

Compounds of formula [I] were prepared as described in scheme 3 above. The ester was reduced by sodium borohydride (16 eq.) in ethanol to the primary alcohol of formula [R], thereafter was the alcohol oxidized with Dess-Martin reagent (2 eq) giving the aldehyde of formula [S]. The aldehyde was then transformed to the hydantoin with ammonium carbonate (9 eq.) and potassium cyanide (5 eq.) in ethanol and water giving the final product [T].

Compound 6.01

Prepared according to the procedure outlined in scheme 12:

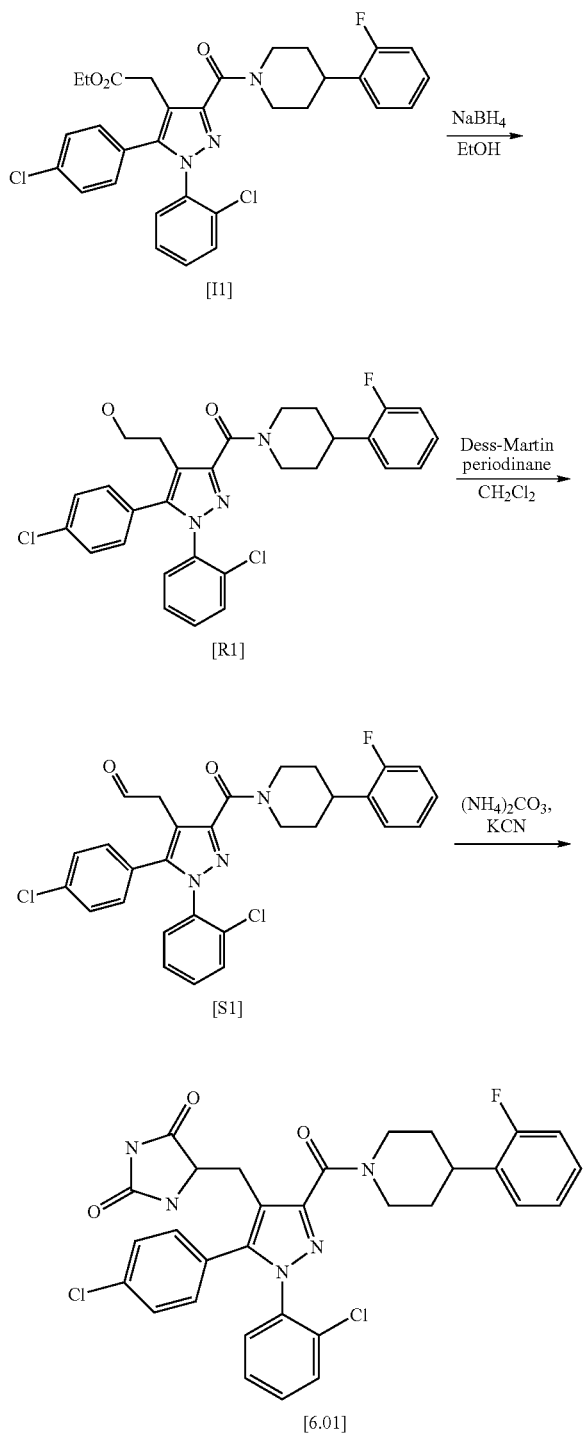

Compound of formula [I1] was prepared as described in scheme 4 above.

To a solution of [I1] (307 mg, 0.53 mmol) in ethanol (12 ml) was sodium borohydride (320 mg, 8.5 mmol) added and the suspension was stirred at room temperature. The reaction was followed by UPLC but after 2 days there were still some starting material left so some more ethanol and sodium borohydride was added at two occasions while continuing stirring the reaction. The reaction went never to completion and after stirring for a week, the reaction mixture was quenched by addition of water followed by $NH_4Cl$ (aq.). The reaction mixture was extracted with dichloromethane (2×30 ml) and washed with brine (20 ml). The combined organic phases were dried over $MgSO_4$, filtered, and evaporated yielding 310 mg of crude product [R1]. The crude product was purified by chromatography (silica, EtOAc:Heptane, 1:1) giving 50 mg of [1-(2-Chloro-phenyl)-5-(4-chloro-phenyl)-4-(2-hydroxy-ethyl)-1H-pyrazol-3-yl]-[4-(2-fluoro-phenyl)-piperidin-1-yl]-methanone [R1] and 180 mg of product [R1] and starting material [L1] 180 mg. UPLC/MS (Method F): $R_t$=1.35 min (M+1)+=538.1.

[R1] (50 mg, 0.09 mmol) was placed in a dry flask under nitrogen and dissolved in dry dichloromethane (1 ml) whereupon Dess-Martin periodinane (79 mg, 0.19 mmol) was added. After stirring for 15 min at room temperature a product peak was visible on the UPLCMS but the reaction did not go to completion even though some more of the Dess-Martin reagents was added. The reaction mixture was extracted with dichloromethane (10 ml) and washed with 1:1 10% $Na_2S_2O_3$: sat. $NaHCO_3$ (10 ml), followed by water and brine. The organic phase was dried through a phase separation column (Biotage) and concentrated in vacuo to give crude {1-(2-Chloro-phenyl)-5-(4-chloro-phenyl)-3-[4-(2-fluoro-phenyl)-piperidine-1-carbonyl]-1H-pyrazol-4-yl}-acetaldehyde [S1]. UPLC/MS (Method F): $R_t$=1.44 min (M+1)+=536.0. The crude material was immediately used in next step.

The intermediate formed [S1], ammonium carbonate (80 mg, 0.84 mmol), and potassium cyanide (30 mg, 0.46 mmol) were mixed in ethanol (1 ml) and water (1 ml). The flask was sealed and heated at 75° C. over night. The reaction mixture was poured into water and extracted with EtOAc (2×10 ml) after adjusting the pH=5 with 1 M HCl. The combined organic phases were dried over $MgSO_4$, filtered and evaporated yielded 169 mg of crude hydantoin. 30 mg of the crude product was purified by preparative LCMS (method E) to give purified 5-{1-(2-Chloro-phenyl)-5-(4-chloro-phenyl)-3-[4-(2-fluoro-phenyl)-piperidine-1-carbonyl]-1H-pyrazol-4-yl-methyl}-imidazolidine-2,4-dione [6.01]. UPLC/MS (Method F): $R_t$=1.26 min (M+1)+=606.0

Compound 6.02

Prepared according to the procedure outlined in scheme 12 identical to the one described for the preparation of compound 6.01:

Scheme 12a

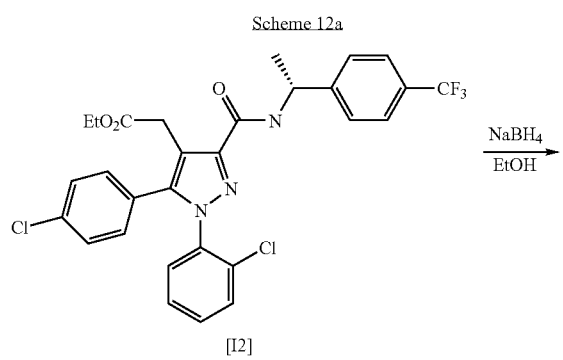

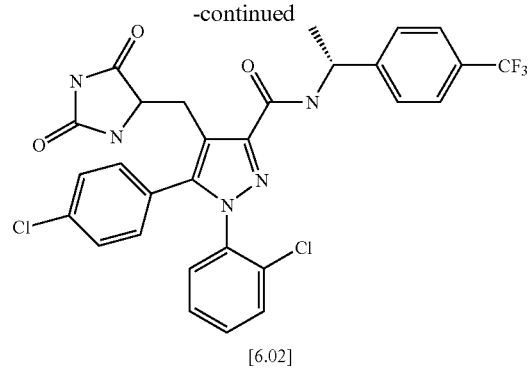

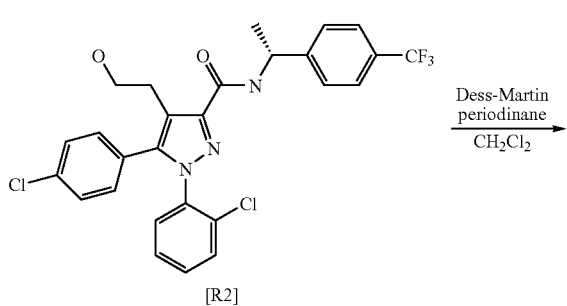

Compound of formula [I2] was prepared as described in scheme 4a.

Compounds of General Formula [7]

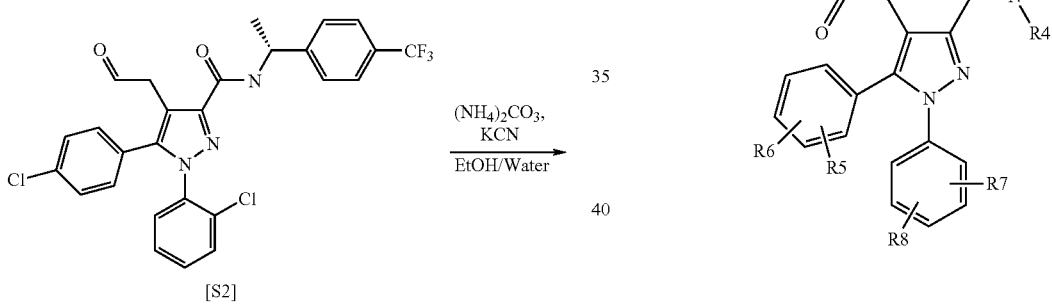

Wherein $R_5$ and $R_8$ are hydrogen.

| Cpd No. | Compound Name | $R_3$—N—$R_4$ | $R_6$ | $R_7$ | Analysis HPLC RT MS (API-ES+) Method F |
|---|---|---|---|---|---|
| 7.01 | 5-(4-Chloro-phenyl)-4-(2,5-dioxo-imidazolidin-4-yl)-1-(2-fluoro-phenyl)-1H-pyrazole-3-carboxylic acid [(R)-1-(4-trifluoromethyl-phenyl)-ethyl]-amide | (piperidine with 2-fluorophenyl) | Para Cl | Ortho Fl | 1.21 min. 586.0 (M + H)+ |

Synthesis

Scheme 13

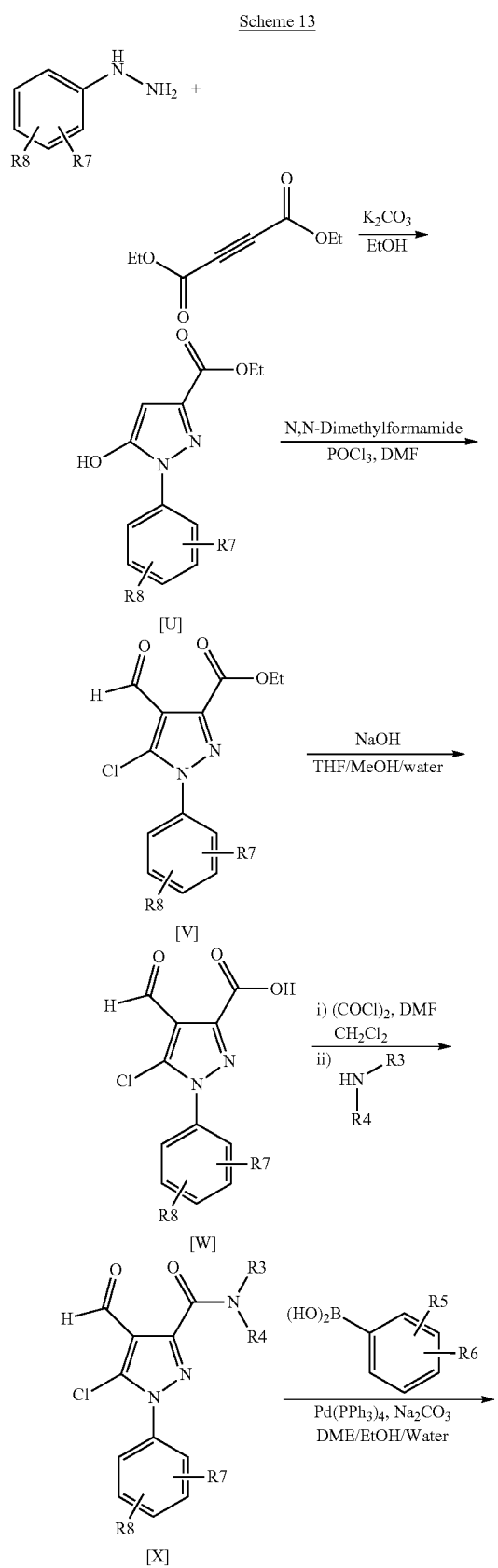

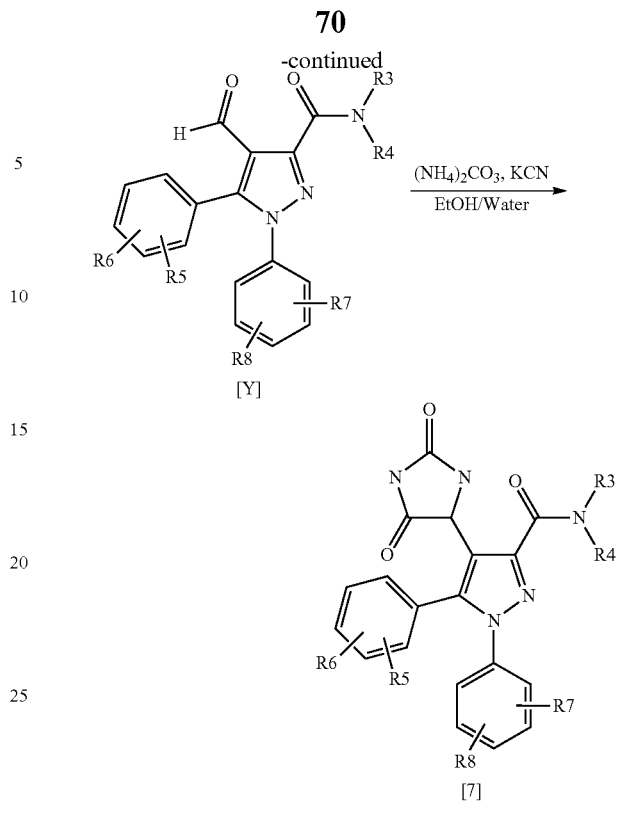

Compounds of formula [Z] were prepared according to the procedure outlined in scheme 13. Substituted phenyl hydrazine was reacted with diethylacetylene dicarboxylate in the presence of base, eg. potassium carbonate (2 eq.) in ethanol and heated for reflux forming the pyrazole [U]. The pyrazole [U] was reacted with N,N-dimethyl formamide (1.2 eq.) and phosphorous oxychloride (12 eq.) during reflux giving the compound of formula [V]. The ester functionality was hydrolysed with sodium hydroxide and the resulting carboxylic acid [W] was subjected to an amide coupling by first forming the acid chloride with oxalyl chloride before adding the amine and a non-nucleophilic base yielding [X]. Thereafter was a Suzuki reaction taking place using a catalytic amount of palladium tetrakis and a substituted boronic acid giving the intermediate [Y]. The final products [Z] were synthesised by transforming the aldehyde to an hydantoin by reflux with ammonium carbonate (6 eq.) and potassium carbonate (3 eq.) in ethanol/water.

Compound 7.01

Prepared according to the procedure outlined in scheme 14:

Scheme 14.

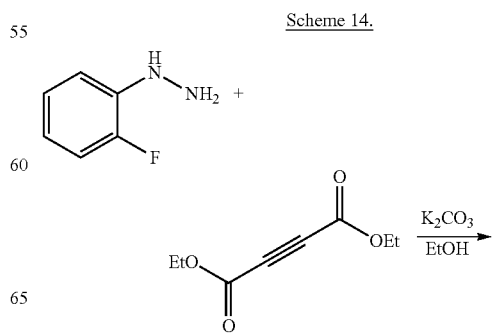

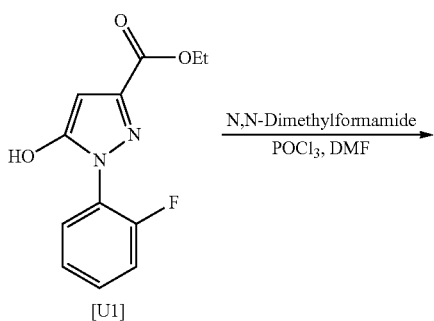

[U1]

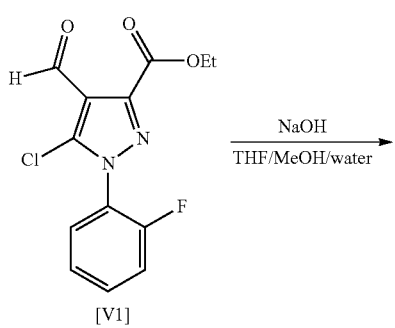

[V1]

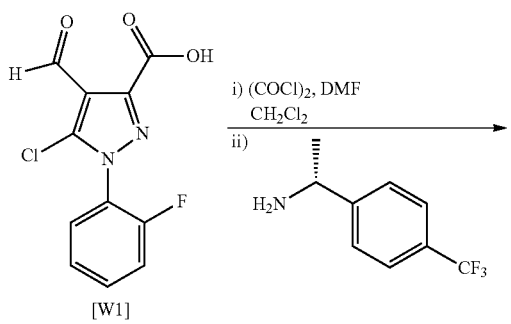

[W1]

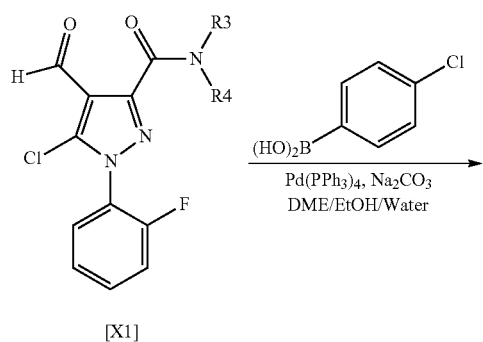

[X1]

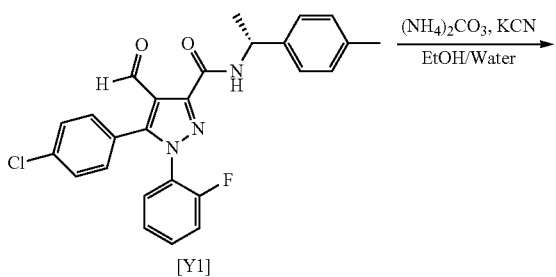

[Y1]

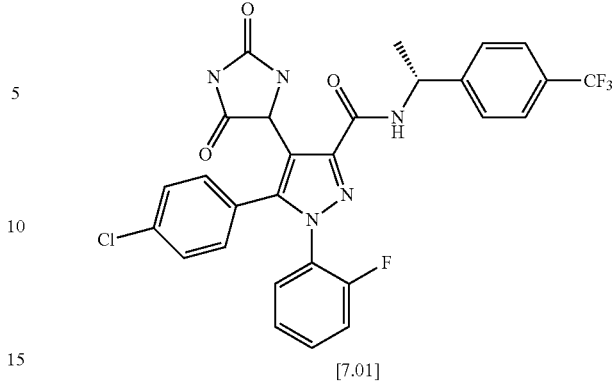

[7.01]

In a flask were 2-fluorophenylhydrazine hydrochloride (12.2 g, 75 mmol), diethylacetylene dicarboxylate (12.8 g, 75 mmol), potassium carbonate (20.7 g, 150 mmol), and ethanol (200 ml) placed and the resulting slurry heated at reflux for 5 hours. The mixture was cooled to room temp, diluted with water (400 ml) and acidified carefully with 2M hydrochloric acid. The mixture was stirred for 2 h then the resulting suspended solid collected by filtration, washed with water (3×50 ml) and dried in vacuo giving 11.4 g of 5-Chloro-1-(2-fluorophenyl)-1H-pyrazole-3-carboxylic acid ethyl ester [U1]. $^1$H NMR (300 MHz., DMSO): δ 1.29 (3H,t), 4.25 (2H,q), 5.92 (1H,s), 7.34-7.60 84H,m), 11.90 (1H,s,br). LCMS (Method A): RT=1.75 min, (M+H)$^+$=251.

N,N-dimethylformamide (4.6 ml, 59 mmol) was added drop wise to a stirred solution of [U1] (12.4 g, 50 mmol) in POCl$_3$ (55 ml) at room temperature. The mixture was heated to reflux for 4 h whereupon LCMS indicated complete conversion. The mixture was cooled to room temperature and the resulting syrup added drop wise to ice/water (ca. 1 l). The mixture was stirred for 2 h whereupon a free-flowing suspension was obtained. The resulting solid was collected by filtration, washed with water and dried in vacuo to give 5-Chloro-1-(2-fluoro-phenyl)-4-formyl-1H-pyrazole-3-carboxylic acid ethyl ester [V1] (15.01 g, 102%). $^1$H NMR (300 MHz., CDCl$_3$): δ 1.44 (3H,t), 4.50 (2H,q), 7.28-7.38 (2H,m), 7.50 (1H,t), 7.55-7.63 (1H,m), 10.55 (1H,s). LCMS (Method A): RT=2.43 min (M+H)$^+$297. 2M Sodium hydroxide solution (50 ml) was added to a stirred solution of [V1] dissolved in THF (250 ml). Methanol (30 ml) was added to give a homogeneous solution. After 2 h, LCMS indicated completion of reaction. The mixture was diluted with water (250 ml) and extracted with ethyl acetate (250 ml). The organic phase was extracted with 1M sodium hydroxide solution (100 ml). Combined aqueous extracts were acidified with 4M hydrochloric acid and extracted with ethyl acetate (2×250 ml). The organic extracts were dried with MgSO$_4$ and the solvent was removed in vacuo yielding 10.15 g of 5-Chloro-1-(2-fluorophenyl)-4-formyl-1H-pyrazole-3-carboxylic acid [W1]. $^1$H NMR (300 MHz., DMSO): δ 7.49 (1H,t), 7.61 (1H,t), 7.71-7.79 (2H,m), 10.36 (1H,s). LCMS (Method A): RT=1.73 min, (M+H)$^+$ 269/271.

Oxalyl chloride (0.19 ml, 2.2 mmol) was added to a stirred solution of [W1] (300 mg, 1.1 mmol) in dichloromethane (3 ml) containing a few drops of DMF and after 2.5 h was the solvent removed in vacuo. The residue was dissolved in dichloromethane (3 ml) and was added drop wise to a stirred solution of (R)-1-(4-trifluoromethyl-phenyl)-ethylamine (250 mg, 1.3 mmol) and triethylamine (0.5 ml) in dichloromethane (3 ml). The reaction mixture was stirred over night whereupon NH$_4$Cl (aq.) (10 ml) and dichloromethane (10 ml) were added. The organic layer was the phases separated and evaporation yielded 540 mg of crude product. The product was purified by chromatography (prepacked silica colon, 10 g, EtOAc:Heptane, 1:3) yielding 250 mg of 5-Chloro-1-(2-fluoro-phenyl)-4-formyl-1H-pyrazole-3-carboxylic acid [(R)-1-(4-trifluoromethyl-phenyl)ethyl]-amide [Y1].

1H-NMR (DMSO): δ 1.51 (3H, d), 5.25 (1H, q), 7.45-7.84 (8H, m), 9.35 (1H, d), 10.35 (1H,s) ppm. UPLCMS (Method F) RT=1.32, (M+1)+=440.0

[Y1] (50 mg, 0.11 mmol), 4-chlorophenylboronic acid (23 mg, 0.15 mmol), Pd(PPh$_3$)$_4$ (10 mg), 2M sodium carbonate solution (0.1 ml), ethanol (0.23 ml), and DME (0.6 ml) were mixed and the flask was flushed with argon. The reaction was heated in m.v. at 150° C. for 10 minutes. To the reaction was 1M NaOH (aq.) (10 ml) added followed by extraction with dichloromethane (2×10 ml). The combined organic phases were dried over MgSO$_4$, filtered, and the solvent was removed in vacuo yielding the crude [Y1]. The product was purified by chromatography (silica, EtOAc:Heptane, 4:1 to 1:1) yielding 34 mg not completely pure material that was used without further purification. UPLC/MS (Method F): R$_t$=1.42 min, (M+1)+=516.0.

[Y1] (34 mg, 0.07 mmol), ammonium carbonate (57 mg, 0.6 mmol), and potassium cyanide (21 mg, 0.33 mmol) were mixed in ethanol (1 ml) and water (1 ml) and heated to reflux over night. The reaction mixture was poured into water (10 ml) and extracted with EtOAc (2×10 ml) after the pH was adjusted to pH=5 with 1M HCl. The organic phases were combined and dried over MgSO$_4$, filtered, and evaporated yielded 34.6 mg of crude product. The crude material was purified by preperative LCMS (Method E) yielding 2.79 mg pure [7.01].

$^1$H NMR (DMSO)): δ 1.50 (3H, d), 5.23 (1H, q), 5.29 (1H, d), 7.20-7.39 (4H, m), 7.43-7.58 (3H, m), 7.60-7.74 (5H, m), 8.03 (1H, d), 8.95 (1H, d), 10.49 (1H, s). UPLCMS (Method F) RT=1.21, (M+1)+=586.0.

Biological Data

Compounds were tested in the functional Cannabinoid Receptor-1 assay described below, and their IC$_{50}$ values for antagonizing a CB1 receptor agonist were assessed. The compounds are grouped in three classes:

A: IC$_{50}$ value lower than 0.5 μM
B: IC$_{50}$ value between 0.5 μM and 5 μM
C: IC$_{50}$ value higher than 5 μM Tables 1, 2, 3 and 4 Show Results for Compounds of the Invention, Synthesised as Above.

TABLE 1

Compounds of general formula [1]

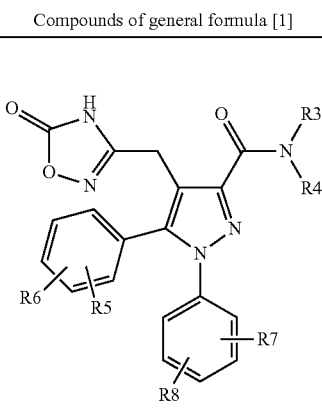

wherein R$_5$ and R$_6$ are hydrogen.

| Compound Number | R$_3$—N—R$_4$ | R$_6$ | R$_7$ | Antagonism IC50 |
|---|---|---|---|---|
| 1.01 | 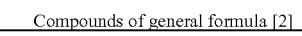 | Para Cl | Ortho Cl | A |

TABLE 2

Compounds of general formula [2]

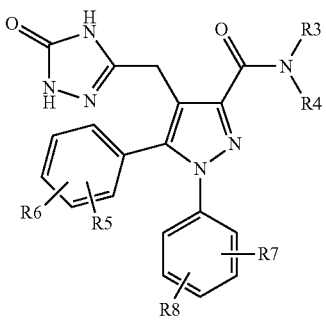

wherein R$_5$ and R$_6$ are hydrogen.

| Compound Number | R$_3$—N—R$_4$ | R$_6$ | R$_7$ | Antagonism IC50 |
|---|---|---|---|---|
| 2.01 | | Para Cl | Ortho Cl | A |

TABLE 2-continued

Compounds of general formula [2]

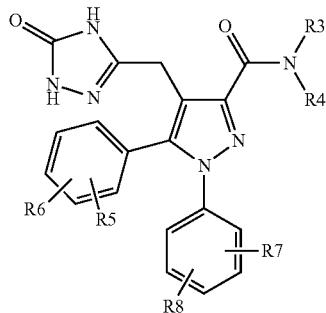

[2]

wherein R₅ and R₆ are hydrogen.

| Compound Number | R₃—N—R₄ | R₆ | R₇ | Antagonism IC50 |
|---|---|---|---|---|
| 2.02 | HN-CH(CH₃)-C₆H₄-CF₃ | Para Cl | Ortho Cl | A |

TABLE 3

Compounds of general formula [3]

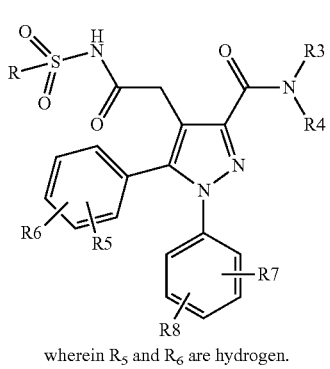

[3]

wherein R₅ and R₆ are hydrogen.

| Compound Number | R₃—N—R₄ | R | R₆ | R₇ | Antagonism IC50 |
|---|---|---|---|---|---|
| 3.01 | 4-(2-fluorophenyl)piperidin-1-yl | Methyl | Para Cl | Ortho Cl | A |

TABLE 3-continued

Compounds of general formula [3]

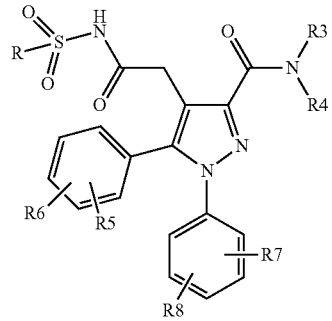

[3]

wherein R₅ and R₆ are hydrogen.

| Compound Number | R₃—N—R₄ | R | R₆ | R₇ | Antagonism IC50 |
|---|---|---|---|---|---|
| 3.02 | N(CH₃)-CH(CH₃)-C₆H₄-CF₃ | Methyl | Para Cl | Ortho Cl | A |

TABLE 4

Compounds of general formula [4]

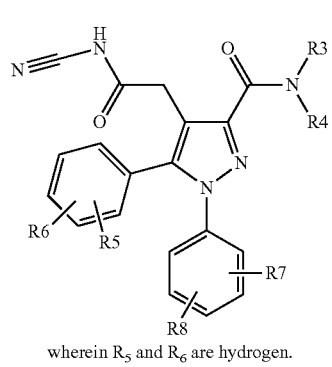

[4]

wherein R₅ and R₆ are hydrogen.

| Compound Number | R₃—N—R₄ | R | R₆ | R₇ | Antagonism IC50 |
|---|---|---|---|---|---|
| 4.01 | 4-(2-fluorophenyl)piperidin-1-yl | Methyl | Para Cl | Ortho Cl | A |

TABLE 4-continued

Compounds of general formula [4]

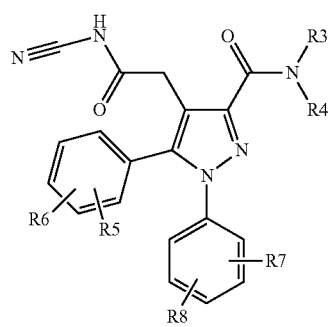

wherein R$_5$ and R$_6$ are hydrogen.

| Compound Number | R$_3$—N—R$_4$ | R | R$_6$ | R$_7$ | Antagonism IC50 |
|---|---|---|---|---|---|
| 4.02 | (1-(4-trifluoromethylphenyl)ethyl)methylamino | Methyl | Para Cl | Ortho Cl | A |
| 4.03 | 4-(3,5-difluorophenoxy)piperidin-1-yl | Methyl | Para Cl | Ortho Cl | A |

TABLE 5

Compounds of general formula [5]

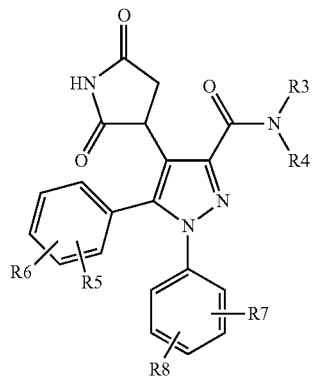

Wherein R$_5$ and R$_6$ are hydrogen.

| Compound Number | R$_3$—N—R$_4$ | R$_6$ | R$_7$ | Antagonism IC50 |
|---|---|---|---|---|
| 5.01 | (1-(4-trifluoromethylphenyl)ethyl)methylamino | Para Cl | Ortho Cl | A |

TABLE 6

Compounds of general formula [6]

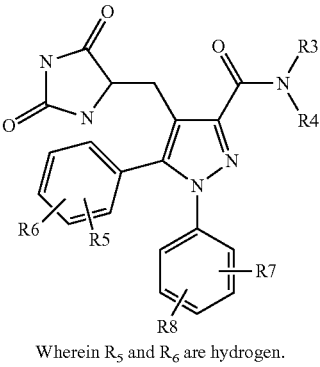

Wherein R$_5$ and R$_6$ are hydrogen.

| Compound Number | R$_3$—N—R$_4$ | R$_6$ | R$_7$ | Antagonism IC50 |
|---|---|---|---|---|
| 6.01 | 4-(2-fluorophenyl)piperidin-1-yl | Para Cl | Ortho Cl | A |

TABLE 6-continued

Compounds of general formula [6]

[6]

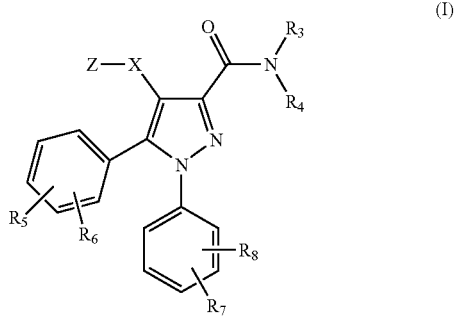

Wherein R$_5$ and R$_6$ are hydrogen.

| Compound Number | R$_3$—N—R$_4$ | R$_6$ | R$_7$ | Antagonism IC50 |
|---|---|---|---|---|
| 6.02 | ![NH-CH(CH3)-C6H4-CF3] | Para Cl | Ortho Cl | A |

Biological Evaluation

Transfection and Cell Culture—The cDNA encoding the human CB1 (Cannabinoid Receptor-1) receptor (GenBank accession number NM_016083) was cloned from a human adipose tissue cDNA library and cloned into the eukaryotic expression vector pcDNA3.1 (Invitrogen).

Chinese Hamster Ovary cells (CHO-K1) stably expressing recombinant human CB1 receptors were generated by transfecting the plasmid containing the coding sequence of the human CB1 receptor in CHO-K1 cells, using lipofectamine, according to the manufacturers instructions. Resistant clones were selected in the presence of 600 µg/ml G418 (Life technology). Stably transfected CHO-K1 cells were maintained in Ham's F-12 culture medium (Invitrogen), supplemented with 10% fetal calf serum (Invitrogen), 100 U/ml penicillin, 100 µg/ml streptomycin (Life Technology), and 600 µg/ml G418.

Cannabinoid Receptor-1 Functional Assay.

Functional activities of the above examples of compounds of the invention were assessed in vitro by measuring their ability to inhibit CP55940-induced [$^{35}$S]GTPγS binding to membranes prepared from CHO-K1 cells expressing the human CB1 receptor (described in Transfection and Cell Culture). CP55940 is a well known non-selective CB1 and CB2 receptor agonist (e.g Felder et al., 1995, Molecular Pharmacology, (48) 443-50). Membranes were prepared by a standard procedure. Briefly, cells were harvested using 10 mM EDTA and collected by centrifugation. Pelleted cells were homogenized in ice-cold 20 mM Hepes (pH 7.4), 10 mM EDTA and protease inhibitors (Complete protease inhibitor cocktail tablet, Roche) using an Ultra Turrax Homogenizer. The homogenate was centrifuged at 14 000 rpm for 45 min. at 4° C. The resultant pellet was resuspended in the same buffer but with only 0.1 mM EDTA and was again centrifuged at 14 000 rpm for 45 min. at 4° C. The resulting pellet (membranes) was resuspended in 20 mM Hepes (pH 7.4), 0.1 mM EDTA, 2 mM MgCl$_2$ and protease inhibitors and protein concentration was determined by Micro BCA Protein Assay Reagent Kit (Pierce Biotechnology) according to the manufacturers instructions. The [$^{35}$S]GTPγS SPA (Scintillation Proximity Assay) binding assay was performed by incubating 5 µg/well membranes prepared from CHO-K1 cells expressing the human CB1 receptor with 1 nM [$^{35}$S]GTPγS (Perkin Elmer—NEG 030H) in the presence of 3 nM of CP55940 and various concentrations of the test compounds at room temperature for 1 hr in 96-well microtiter plates. 0.4 mg/well SPA beads (PVT-WGA; RPNQ0001 Amersham Pharmacia Biotech) were then added and the incubation continued for further 30 min. on an orbital shaker. The assay buffer contained 50 mM HEPES (pH 7.5), 50 mM NaCl, 2.5 mM MgCl$_2$, 0.1% BSA, 1 µM GDP and 100 µg/ml Saponin. Microtiter plates were centrifuged at 1500 rpm for 5 min. and radioactivity was read immediately using a Topcounter (PerkinElmer Life Sciences). Data were analyzed and IC50 values determined by non-linear regression analysis using the Prism software (GraphPad Software, San Diego).

The invention claimed is:

1. A compound of formula (I) or a salt or N-oxide thereof:

(I)

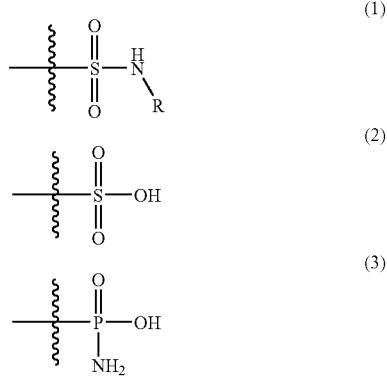

wherein:
X is a bond, or a divalent radical selected from —C(R$_{10}$)(R$_{11}$)—*, —C(R$_{10}$)(R$_{11}$)—O—*, —C(R$_{10}$)(R$_{11}$)CH$_2$—*, —C(R$_{10}$)(R$_{11}$)CH$_2$—O—*, —CH$_2$C(R$_{10}$)(R$_{11}$)—*, —CH$_2$C(R$_{10}$)(R$_{11}$)—O—*, and —CH$_2$—O—C(R$_{10}$)(R$_{11}$)—*, wherein the bond indicated by an asterisk is attached to the pyrazole ring;

Z is a radical selected from the group consisting of those of formulae (1)-(26) as follows:

(1)

$$\begin{array}{c} O \\ \| \\ -S-N \\ \| \quad \backslash R \\ O \quad H \end{array}$$

(2)

$$\begin{array}{c} O \\ \| \\ -S-OH \\ \| \\ O \end{array}$$

(3)

$$\begin{array}{c} O \\ \| \\ -P-OH \\ | \\ NH_2 \end{array}$$

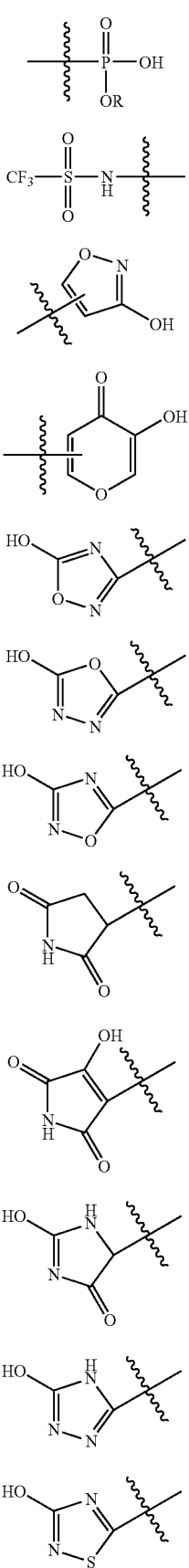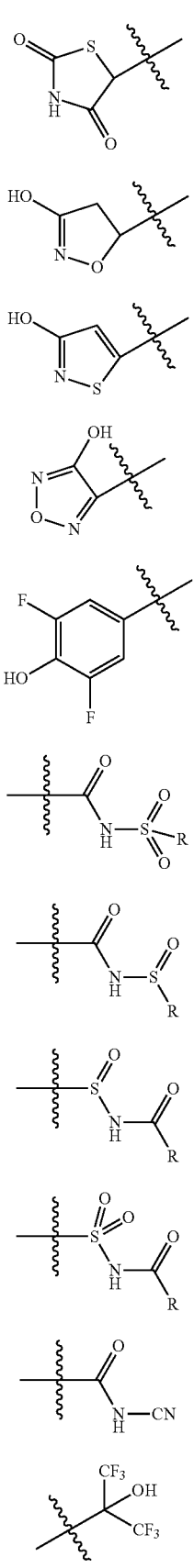

wherein R is $C_1$-$C_6$ alkyl; phenyl or benzyl optionally ring-substituted by $R_5$; or a monocyclic non-aromatic carbocyclic ring of 3 to 6 ring atoms;

$R_3$ is hydrogen, $(C_1$-$C_3)$alkyl or $(C_1$-$C_3)$fluoroalkyl;

$R_4$ is a radical of formula -$(Alk_1)_p$-$(Q_1)_r$-$(L)_s$-$Q_2$ wherein
  p, r and s are independently 0 or 1, provided that at least one of p, r and s is 1;
  $Alk_1$ is a divalent $(C_1$-$C_4)$alkylene radical which (a) is optionally substituted on one carbon by $R_{10}$ and/or $R_{11}$ or by one or two optional substituents, and/or (b) optionally contains a —O—, —S—, —CO—, —SO—, —SO$_2$—, or —NR$_9$— link;
  L is a divalent radical of formula -$(Alk_2)_n$-$(W)_m$—, in either orientation, wherein
    n and m are independently 0 or 1;
    $Alk_2$ is —C($R_{10}$)($R_{11}$)—; and
    W is —CO—, —SO$_2$—, —O—, —NR$_9$— or —SO—; provided that when W and/or $Alk_2$ are linked to a heteroatom W is not —O—, —NR$_9$— or —SO—;
  $Q_1$ is a monocyclic carbocyclic ring of 3 to 6 ring atoms, a bicyclic carbocyclic ring system of 7 to 10 ring atoms, a monocyclic heterocyclic ring of 4 to 6 ring atoms or a bicyclic carbocyclic ring system of 8 to 10 ring atoms, any of which rings or ring systems being optionally substituted;
  $Q_2$ is (a) in the case where s in -$(L)_s$-$Q_2$ is 0 or 1, a monocyclic carbocyclic ring of 3 to 6 ring atoms, a bicyclic carbocyclic ring system of 7 to 10 ring atoms, a monocyclic heterocyclic ring of 4 to 6 ring atoms or a bicyclic carbocyclic ring system of 8 to 10 ring atoms, any of which rings or ring systems being optionally substituted; or (b) only in the case where s in -$(L)_s$-$Q_2$ is 0, hydrogen;
or $R_3$ and $R_4$ taken together with the nitrogen to which they are attached form a cyclic amino ring of 4 to 7 ring atoms which is optionally substituted by a radical of formula -$(L)_s$-$Q_2$ wherein s, L and $Q_2$ are as defined above, or by an optional substituent selected from hydroxy, methoxy, —NH$_2$—, or mono- or di-$(C_1$-$C_3)$alkylamino;
$R_5$, $R_6$, $R_7$ and $R_8$ are each independently selected from hydrogen —F, —Cl, —Br, —CN, $(C_1$-$C_3)$alkyl, $(C_1$-$C_3)$fluoroalkyl, cyclopropyl, and —OR$_9$;
$R_9$ is hydrogen, $(C_1$-$C_3)$alkyl, $(C_1$-$C_3)$fluoroalkyl, or $(C_3$-$C_6)$cycloalkyl; and
$R_{10}$ is hydrogen, $(C_1$-$C_3)$alkyl, hydroxyl or NH$_2$, and $R_{11}$ is hydrogen or $(C_1$-$C_3)$alkyl; or $R_{10}$ and $R_{11}$ taken together with the carbon atom to which they are attached form a $(C_3$-$C_5)$cycloalkyl ring.

2. A compound as claimed in claim 1 wherein —X— is —CH$_2$—, —CH$_2$O—*, or —CH$_2$OCH$_2$—*, wherein the bond indicated by an asterisk is attached to the pyrazole ring.

3. A compound as claimed in claim 1 wherein $R_5$, $R_6$, $R_7$ and $R_8$ are independently selected from hydrogen, —F and —Cl.

4. A compound as claimed in claim 1 wherein $R_3$ is hydrogen and, in the radical $R_4$, p and s are 0, and r is 1.

5. A compound as claimed in claim 1 wherein $R_3$ is hydrogen and, in the radical $R_4$, p and r are 1.

6. A compound as claimed in claim 5 wherein, in $R_4$, $Alk_1$ is —CH$_2$—.

7. A compound as claimed in claim 1 wherein, in $R_4$, $Q_1$ is an optionally substituted divalent phenyl radical.

8. A compound as claimed in claim 1 wherein, in $R_4$, $Q_2$ is hydrogen, or optionally substituted phenyl.

9. A compound as claimed in claim 4 wherein one or two optional ring substituents in are present in ring $Q_1$ and/or ring $Q_2$, said substituents being selected from —F, —Cl, —Br, —CN, —CF$_3$, —CH$_3$, cyclopropyl, and —OCH$_3$.

10. A compound as claimed in claim 4 wherein one or both of rings $Q_1$ and $Q_2$ are unsubstituted.

11. A compound as claimed in claim 1 wherein the radical —C(=O)NR$_3$R$_4$ in formula (I) is selected from the group consisting of (A)-(R) and (X1)-(X12):

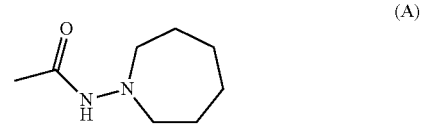
(A)

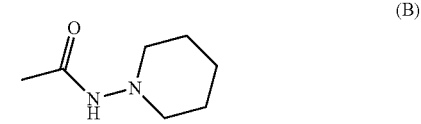
(B)

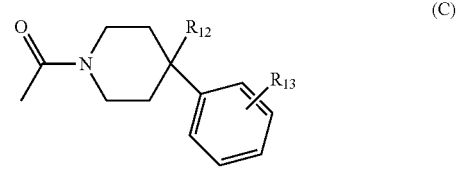
(C)

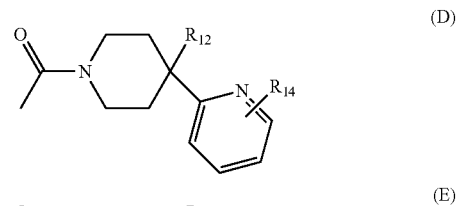
(D)

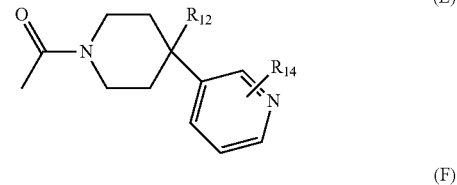
(E)

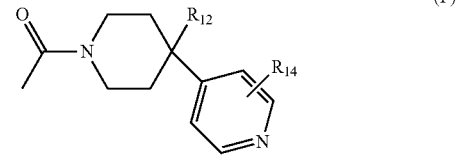
(F)

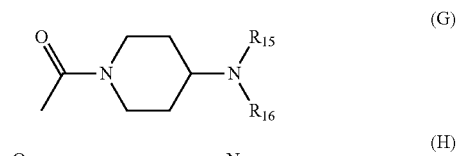
(G)

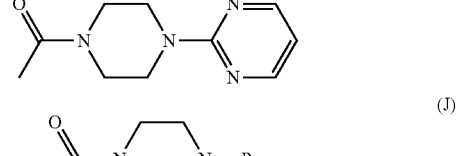
(H)

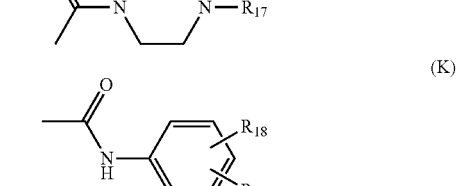
(J)

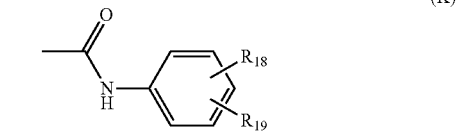
(K)

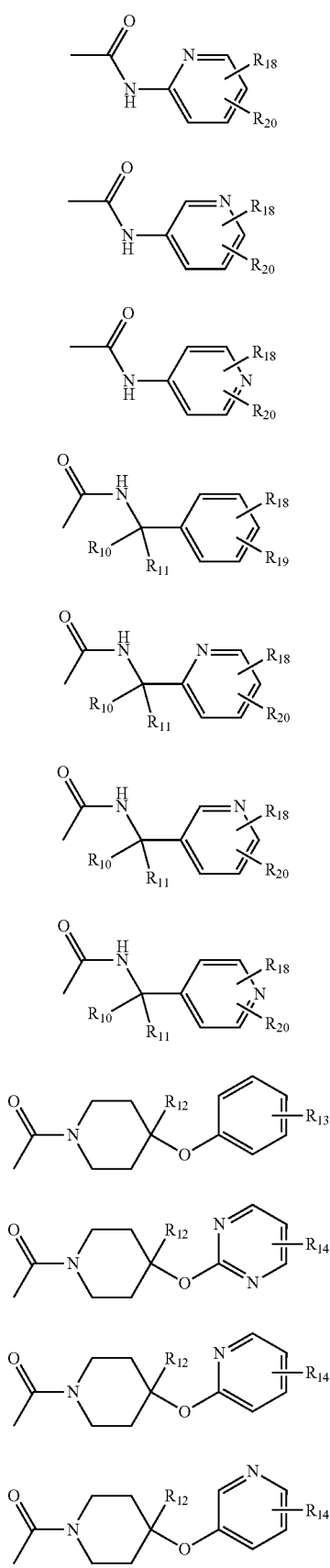
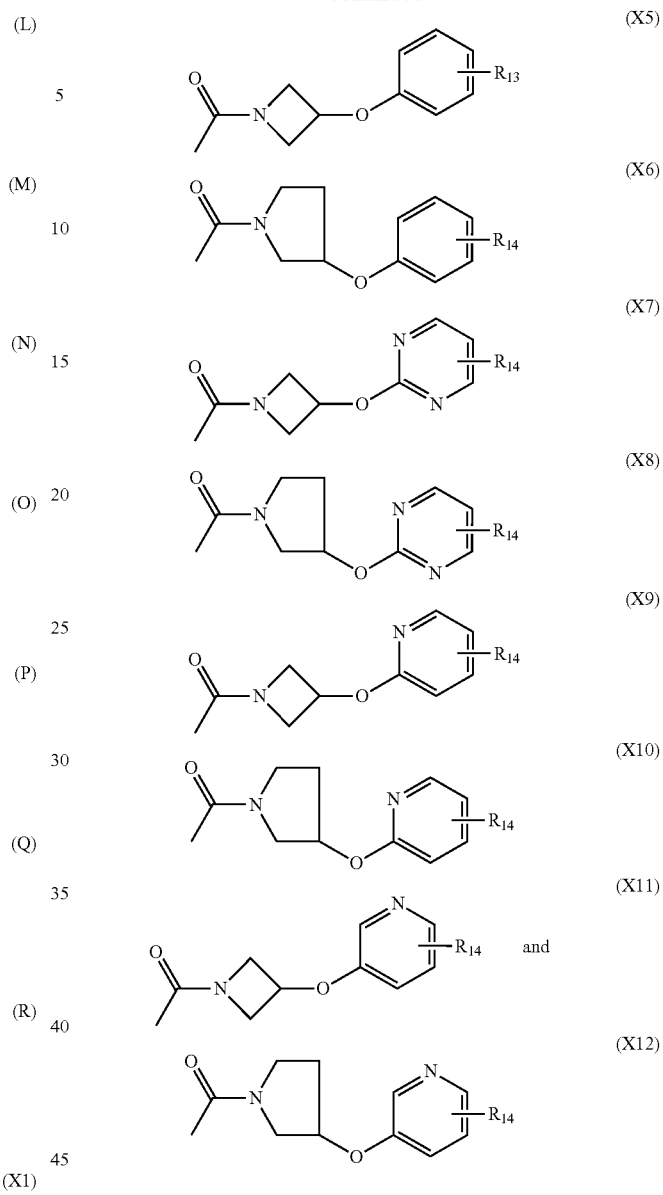

wherein
R$_{10}$ and R$_{11}$ are as defined in claim 1
R$_{12}$ is selected from hydrogen, —CH$_3$, —OH, —CN and —COOH;
R$_{13}$ is selected from hydrogen, —F, —CF$_3$, —OCF$_3$, —Br, —Cl, —OCH$_3$, —CH$_3$, and —CN;
R$_{14}$ is selected from hydrogen, —F, —CF$_3$, —OCF$_3$, —Br, —Cl, —OCH$_3$, —CH$_3$, —CN, and —OH;
R$_{15}$ and R$_{16}$ are independently selected from hydrogen and (C$_1$-C$_6$)alkyl or R$_{15}$ and R$_{16}$ taken together with the nitrogen to which they are attached form a cyclic amino ring of 4 to 7 ring atoms;
R$_{17}$ is selected from hydrogen, (C$_1$-C$_6$)alkyl, (C$_1$-C$_6$)alkylC(=O)—, (C$_1$-C$_6$)alkylSO$_2$—, benzyloxycarbonyl-, and —C(=O)OCH$_3$;
R$_{18}$ is selected from hydrogen, —F and —CN;
R$_{19}$ is selected from hydrogen, F, —CF$_3$, —OCF$_3$, —Br, —Cl, —OCH$_3$, —CH$_3$, and —CN; and
R$_{20}$ is selected from hydrogen, F, —CF$_3$, —OCF$_3$, —Br, —Cl, —OCH$_3$, —CH$_3$, —CN, and —OH.

12. A pharmaceutical composition comprising a compound as claimed in claim 1, together with one or more pharmaceutically acceptable carriers or excipients.

13. The composition as claimed in claim 12 for the treatment of diseases or conditions which are mediated by CB1 receptor signalling activity, the disease or conditions being selected from obesity, type 2 diabetes, non-alcholic fatty liver disease, steatohepatitis, steatosis, hepatic fibrosis, hepatic cirrhosis, atherosclerosis, dyslipidemia, hyperlipidemia, impaired glucose tolerance, or insulin resistance.

14. A method for the treatment of diseases or conditions which are mediated by CB1 receptor signaling activity, which method comprises administering to a subject suffering such disease or condition an effective amount of a compound as claimed in claim 1, the diseases or conditions being selected from obesity, type 2 diabetes, non-alcoholic fatty liver disease, steatohepatitis, steatosis, hepatic fibrosis, hepatic cirrhosis, atherosclerosis, dyslipidemia, hyperlipidemia, impaired glucose tolerance, or insulin resistance.

* * * * *